(12) United States Patent
Harris et al.

(10) Patent No.: US 7,981,655 B2
(45) Date of Patent: Jul. 19, 2011

(54) MODIFIED CYTOSINE DEAMINASES

(75) Inventors: Reuben S Harris, St. Paul, MN (US);
Hiroshi Matsuo, St. Paul, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 0 days.

(21) Appl. No.: 12/322,868

(22) Filed: Feb. 6, 2009

(65) Prior Publication Data
US 2009/0269831 A1 Oct. 29, 2009

Related U.S. Application Data

(60) Provisional application No. 61/085,225, filed on Jul. 31, 2008, provisional application No. 61/063,926, filed on Feb. 7, 2008.

(51) Int. Cl.
| C12N 9/78 | (2006.01) |
| C12N 9/80 | (2006.01) |
| C12N 5/02 | (2006.01) |
| C12N 5/07 | (2010.01) |
| C12P 21/06 | (2006.01) |
| C07H 21/04 | (2006.01) |

(52) U.S. Cl. ....... 435/227; 435/69.1; 435/228; 435/350; 435/440; 536/23.2

(58) Field of Classification Search .................. None
See application file for complete search history.

(56) References Cited

U.S. PATENT DOCUMENTS
4,683,195 A   7/1987  Mullis et al.
6,815,194 B2 * 11/2004 Honjo et al. .................. 435/227

OTHER PUBLICATIONS

Sawyer et al. Ancient adaptive evolution of the primate antiviral DNA-editing enzyme APOBEC3G, PLoS Biol. Sep. 2004;2(9):E275. Epub Jul. 20, 2004.*
UniProt Accession No. Q694B7, DNA dC->dU editing enzyme APOBEC-3G, publication Oct. 11, 2004.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
GenBank Accession No. AAH38808.1, dated Jan. 30, 2008, 3 pages.
GenBank Accession No. NM_001077845.1, dated Dec. 30, 2008, 2 pages.
GenBank Accession No. NM_001093784.1, dated May 23, 2007, 2 pages.
GenBank Accession No. NM_001097446.1, dated Feb. 19, 2009, 2 pages.
GenBank Accession No. NM_020661, dated Aug. 16, 2009, 4 pages.
GenBank Accession No. NM_021822, dated Jul. 26, 2009, 4 pages.
GenBank Accession No. NM_145298, dated Jul. 26, 2009, 5 pages.
GenBank Accession No. NP_004891.3, dated Aug. 3, 2008, 3 pages.
GenBank Accession No. NP_006780.1, dated Apr. 3, 2009, 2 pages.
GenBank Accession No. NP_055323.2, dated Mar. 15, 2009, 3 pages.
GenBank Accession No. $NP_{13}$ 065712, dated Aug. 16, 2009, 3 pages.
GenBank Accession No. NP_065712.1, dated Aug. 16, 2009, 3 pages.
GenBank Accession No. NP_068594.1, dated Jul. 26, 2009, 3 pages.
GenBank Accession No. NP_084531.1, dated Dec. 11, 2005, 2 pages.
GenBank Accession No. NP_660341, dated Jul. 26, 2009, 3 pages.
GenBank Accession No. NP_663745.1, dated Jul. 26, 2009, 3 pages.
Betts et al., "Cytidine Deaminase. The 2·3 Å Crystal Structure of an Enzyme: Transition-state Analog Complex," *J Mol Biol.*, 1994, 235(2):635-656.
Chelico et al., "APOBEC3G DNA deaminase acts processively 3' --> 5' on single-stranded DNA," *Nat Struct Mol Biol.*, 2006, 13(5):392-399.
Chen et al., "Extensive mutagenesis experiments corroborate a structural model for the DNA deaminase domain of APOBEC3G," *FEBS Letters*, 2007, 581:4761-4766.
Chen et al., "Structure of the DNA deaminase domain of the HIV-1 restriction factor APOBEC3G," *Nature*, 2008, 452:116-121.
Clore et al., "Assignment of the Side-Chain $^1$H and $^{13}$C Resonances of Interleukin-1β Using Double- and Triple-Resonance Heteronuclear Three-Dimensional NMR Spectroscopy," *Biochemistry*, 1990, 29(35):8172-8184.
Clubb et al., "A Constant-Time Three-Dimensional Triple-Resonance Pulse Scheme to Correlate Intraresidue $^1$H$^N$, $^{15}$N, and $^{13}$C' Chemical Shifts in $^{15}$N-$^{13}$C-Labeled Proteins," *J Magn Reson.*, 1992, 97:213-217.
Combet et al., "Geno3D: automatic comparative molecular modelling of protein," *Bioinformatics*, 2002, 18(1):213-214.
Conticello et al., "DNA Deamination in Immunity: AID in the Context of Its APOBEC Relatives," *Adv Immunol.*, 2007, 94:37-73.
Cornilescu et al., "Protein backbone angle restraints from searching a database for chemical shift and sequence homology," *J Biomol NMR*, 1999, 13:289-302.
Delaglio et al., "NMRPipe: A multidimensional spectral processing system based on UNIX pipes," *J Biomol NMR.*, 1995, 6(3):277-293.
Desmet et al., "The dead-end elimination theorem and its use in protein side-chain positioning," *Nature*, 1992, 356:539-542.
Devany et al., "Solution NMR structure of the C-terminal domain of the human protein DEK," *Protein Sci.*, 2004, 13(8):2252-2259.
Goldstein, "Efficient Rotamer Elimination Applied to Protein Side-Chains and Related Spin Glasses," *Biophys J.*, 1994, 66:1335-1340.
Grzesiek et al., "Correlation of Backbone Amide and Aliphatic Side-Chain Resonances in $^{13}$C/$^{15}$N-Enriched Proteins by Isotopic Mixing of $^{13}$C Magnetization," *J Magn Reson Series B*, 1993, B101:114-119.
Guermeur et al., "Improved performance in protein secondary structure prediction by inhomogeneous score combination," *Bioinformatics*, 1999, 15(5):413-421.
Haché et al., "The Retroviral Hypermutation Specificity of APOBEC3F and APOBEC3G Is Governed by the C-terminal DNA Cytosine 280(12): 10920-10924 Deaminase Domain," *J Biol Chem.*, 2005, 280(12):10920-10924.

(Continued)

Primary Examiner — Anand U Desai
Assistant Examiner — Iqbal H Chowdhury
(74) *Attorney, Agent, or Firm* — Fish & Richardson P.C.

(57) ABSTRACT

The document provides modified cytosine deaminases with increased solubility and high levels of DNA cytosine deaminase activity.

15 Claims, 28 Drawing Sheets
(9 of 28 Drawing Sheet(s) Filed in Color)

OTHER PUBLICATIONS

Harjes et al., "An Extended Structure of the APOBEC3G Catalytic Domain suggests a Unique Holoenzyme Model," *J Mol Biol.*, 2009, 389:819-832.

Harris et al., "RNA editing enzyme APOBEC1 and some of its homologs can act as DNA mutators," *Mol Cell*, 2002, 10(5):1247-1253.

Herrmann et al., "Protein NMR structure determination with automated NOE-identification in the NOESY spectra using the new software ATNOS," *J Biomol NMR*, 2002, 24:171-189.

Herrmann et al., "Protein NMR Structure Determination with Automated NOE Assignment Using the New Software CANDID and the Torsion Angle Dynamics Algorithm DYANA," *J Mol. Biol.*, 2002, 319(1):209-227.

Huthoff and Malim, "Cytidine deamination and resistance to retroviral infection: Towards a structural understanding of the APOBEC proteins," *Virology*, 2005, 334(2):147-153.

Ikura et al., "A Novel Approach for Sequential Assignment of $^1$H, $^{13}$C, and $^{15}$N Spectra of Larger Proteins: Heteronuclear Triple-Resonance Three-Dimensional NMR Spectroscopy. Application to Calmodulin," *Biochemistry*, 1990, 29:4659-4667.

Iwatani et al., "Biochemical Activities of Highly Purified, Catalytically Active Human APOBEC3G: Correlation with Antiviral Effect," *J Virol.*, 2006, 80(12):5992-6002.

Jarmuz et al., "An anthropoid-specific locus of orphan C to U RNA-editing enzymes on chromosome 22," *Genomics*, 2002, 79(3):285-296.

Johansson et al., "Crystal structure of the tetrameric cytidine deaminase from *Bacillus subtilis* at 2.0 A resolution," *Biochemistry*, 2002, 41:2563-2570.

Jónsson et al., "Evolutionarily conserved and non-conserved retrovirus restriction activities of artiodactyl APOBEC3F proteins," *Nucl Acids Res.*, 2006, 34(19):5683-5694.

Kay et al., "Three-dimensional triple-resonance NMR spectroscopy of isotopically enriched proteins," *J Magn Reson.*, 1990, 89(3):496-514.

Ko et al., "Crystal Structure of Yeast Cytosine Deaminase," *J Biol Chem.*, 2003, 278(21):19111-19117.

Larue et al., "The artiodactyl *APOBEC3* innate immune repertoire shows evidence for a multi-functional domain organization that existed in the ancestor of placental mammals," *BMC Mol Biol.*, 2008, 9(104):1-20.

Larue et al., "Guidelines for Naming Nonprimate APOBEC3 Genes and Proteins," *J Virol*, 2009, 83(2):494-497.

Li et al., "Functional domains of APOBEC3G required for antiviral activity," *J Cell Biochem.*, 2004, 92(3):560-572.

Liddament et al., "APOBEC3F Properties and Hypermutation Preferences Indicate Activity against HIV-1 in Vivo," *Curr Biol.*, 2004, 14(15):1385-1391.

Losey et al., "Crystal structure of *Staphylococcus aureus* tRNA adenosine deaminase TadA in complex with RNA," *Nat Struct Mol Biol.*, 2006, 13(2):153-159.

Matsuo et al., "A Sensitive HN(CA)CO Experiment for Deuterated Proteins," *J Magn Reson.*, 1996, B 110:112-115.

Matsuo et al., "Increased Sensitivity in HNCA and HN(CO)CA Experiments by Selective $C^\beta$ Decoupling," *J Magn Reson.*, 1996, B 113:91-96.

Matsuo et al., "Use of Selective $C^\alpha$ Pulses for Improvement of HN(CA)CO-D and HN(COCA)NH-D Experiments," *J Magn Reson.*, 1996, B111:194-198.

Navarro et al., "Complementary function of the two catalytic domains of APOBEC3G," *Virology*, 2005, 333(2):374-386.

Newman et al., "Antiviral function of APOBEC3G can be dissociated from cytidine deaminase activity," *Curr Biol.*, 2005, 15(2):166-170.

Nowarski et al., "Hypermutation by intersegmental transfer of APOBEC3G cytidine deaminase," *Nat Struct Mol Biol.*, 2008, 15(10):1059-1066.

Opi et al., "Monomeric APOBEC3G Is Catalytically Active and Has Antiviral Activity," *J Virol.*, 2006, 80:4673-4682.

Philo, "A Method for Directly Fitting the Time Derivative of Sedimentation Velocity Data and an Alternative Algorithm for Calculating Sedimentation Coefficient Distribution Functions," *Anal Biochem.*, 2000, 279:151-163.

Philo, "Improved methods for fitting sedimentation coefficient distributions derived by time-derivative techniques," *Anal Biochem.*, 2006, 354:238-246.

Prochnow et al., "The APOBEC-2 crystal structure and functional implications for the deaminase AID," *Nature*, 2007, 445:447-451.

Schuck, "On the analysis of protein self-association by sedimentation velocity analytical ultracentrifugation," *Anal Biochem.*, 2003, 320(1):104-124.

Shindo et al., "The Enzymatic Activity of CEM15/Apobec-3G Is Essential for the Regulation of the Infectivity of HIV-1 Virion but Not a Sole Determinant of Its Antiviral Activity," *J Biol Chem.*, 2003, 278(45):44412-44416.

Simon et al., "The Vif and Gag Proteins of Human Immunodeficiency Virus Type 1 Colocalize in Infected Human T Cells," *J Virol.*, 1997, 71(7):5259-5267.

Stafford and Sherwood, "Analysis of heterologous interacting systems by sedimentation velocity: curve fitting algorithms for estimation of sedimentation coefficients, equilibrium and kinetic constants," *Biophys Chem.*, 2004, 108:231-243.

Stenglein et al., "Two Regions within the Aminp-Terminal Half of APOBEC3G Cooperate of Determine Cytoplasmic Localization," *J Virol*, 2009, 82(19):9591-9599.

Teh et al., "The 1.48 Å Resolution Crystal Structure of the Homotetrameric Cytidine Deaminase from Mouse," *Biochemistry*, 2006, 45:7825-7833.

Wittekind and Mueller, "HNCACB, a High-Sensitivity 3D NMR Experiment to Correlate Amide-Proton and Nitrogen Resonances with the Alpha- and Beta-Carbon Resonances in Proteins," *J Magn Reson.*, 1993, B101:201-205.

Xiang et al., "The Structure of the Cytidine Deaminase-Product Complex Provides Evidence for Efficient Proton Transfer and Ground-State Destabilization," *Biochemistry*, 1997, 36:4768-4774.

Xie et al., "The structure of a yeast RNA-editing deaminase provides insight into the fold and function of activation-induced deaminase and APOBEC-1," *Proc Natl Acad Sci USA*, 2004, 101(21):8114-8119.

Zhang et al., "Backbone $^1$H and $^{15}$N resonance assignments of the N-terminal SH3 domain of drk in folded and unfolded states using enhanced-sensitivity pulsed field gradient NMR techniques," *J Biomol NMR*, 1994, 4(6):845-858.

Zhang et al., "Model Structure of Human APOBEC3G," *PLoS ONE*, 2007, 2(4):e378.

* cited by examiner

FIG 1

```
A3G  DPP TFTFNFNNEP WVRGRHETYL CYEVERMHND TWVLLNQRRG FLCNQAPHKH GFLEGRHAEL  260
A2   PAN FFKFQFRNVE YSSGRNKTFL CYVVEAQGK- GGQVQASRGY IEDEH---- ---AAAHAEE  102

A3G  CFLDVIPFWK LDLQDYRVT CFTSWSPCFS CAQEMAKFIS KNKHVSLCIF TARIYD-DQGR  320
A2   AFFNTILPAF D-PALRYNVT WYVSSSPCAA CADRIIKTLS KTKNLRLLIL VGRLFMWEEPE  161

A3G  CQEGLRTLAE AGAKISIMTY SEFKHCWDTF VDHQ---SCPFQP WDGLDEHSQD LSGRLRAIL  380
A2   IQAALKKLKE AGCKLRIMKP QDFEYVWQNF VQOEEGESKAFQP WEDIQENFLY YEEKLADIL  221
```

FIG 4
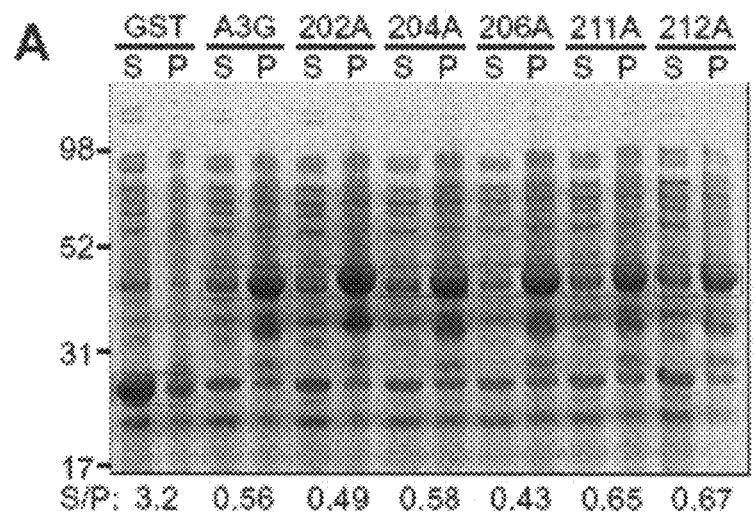
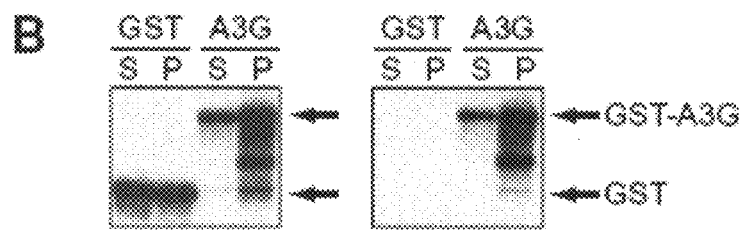
C    S/P relative to A3G198-384
| | |
|---|---|
| > 2 SD higher | 234A, 235A, 241A, 253A, 371A |
| ≤ 2 SD | 202A, 204A, 206A, 211A, 212A, 221A, 227A, 232A, 233A, 243A, 252A, 259A, 265A, 268A, 273A, 289A, 291A, 299A, 310A, 321A, 337A, 340A, 346A, 356A |
| > 2 SD lower | 260A, 261A, 269A, 281A, 288A, 308A |

FIG 10

```
human_A3A              ------------------------------------DPH
human_A3B_ctd          ------------------------------------DPD
human_AID              ---------------------------MDSLLMNRR
human_A3C              ------------------------------------YPG
human_A3F_ctd          ------------------------------------YPH
cow_A3F_ntd            ------------------------------------DPE
sheep_A3F_ntd          ------------------------------------DPE
pig_A3F_ntd            ------------------------------------SPR
mouse_A3_ntd           ------------------------------------SQE
human_APOBEC2          MAQKEEAAVATEAASQNGEDLENLDDPEKLKELIELPPFEIVTGERLPAN
human_A3G_ctd*198-384  ------------------------------------DPP human_A3A              IFTSNFNNG---IGRHKTYLCYEVERLDNGTSVKMDQHRGFLHNQAKNLL
human_A3B_ctd          TFTFNFNNDPLVLRRRQTYLCYEVERLDNGTWVLMDQHMGFLCNEAKNLL
human_AID              KFLYQFKNVRWAKGRRETYLCYVVKRRDSATSFSLD--FGYLRNKN----
human_A3C              TFYFQFKNLWEANDRDETWLCFTVEGIKRRSVVSWK--TGVFRNQVDSE-
human_A3F_ctd          IFYFHFKNLRKAYGRNESWLCFTMEVVKHHSPVSWK--RGVFRNQVDPE-
cow_A3F_ntd            TFYFQFCNLLYANRRNCSYICYKVERRKYHSRASFD--WGVFHNQVYGG-
sheep_A3F_ntd          TFYFQFHNLLYAYGRNCSYICYRVKTWKHRSPVSFD--WGVFHNQVYAG-
pig_A3F_ntd            TFSFHFRNLRFASGRNRSYICCQVE-----GKNCFF--QGIFQNQVPPD-
mouse_A3_ntd           TFKFHFKNLRYAIDRKDTFLCYETRKDCDSPVSLH--HGVFKNKD----
human_APOBEC2          FFKFQFRNVEYSSGRNKTFLCYVVEAQGKGGQVQAS--RGYLEDEH----
human_A3G_ctd*198-384  TFTFNFNNEPWVRGRHETYLCYEVERMHNDTWVLLNQRRGFLCNQAPHKH
                         *  :* *       *   :::*  :                 *  :  ::

human_A3A              CGFYGRHAELRFLDLVPS---LQLDPAQIYRVTWFISWSPCFSWGCAGEV
human_A3B_ctd          CGFYGRHAELRFLDLVPS---LQLDPAQIYRVTWFISWSPCFSWGCAGEV
human_AID              ----GCHVELLFLRYISD---WDLDPGRCYRVTWFTSWSPCYD--CARHV
human_A3C              ---THCHAERCFLSWFCD---DILSPNTKYQVTWYTSWSPCPD--CAGEV
human_A3F_ctd          ---THCHAERCFLSWFCD---DILSPNTNYEVTWYTSWSPCPE--CAGEV
cow_A3F_ntd            ---TRCHTELRFLSWFHA---EKLRPNERYHITWFMSWSPCMK--CAKEV
sheep_A3F_ntd          ---THCHSERRFLSWFCA---KKLRPDECYHITWFMSWSPCMK--CAELV
pig_A3F_ntd            ---PPCHAELCFLSWFQS---WGLSPDEHYVVTWFISWSPCCE--CAAKV
mouse_A3_ntd           ----NIHAEICFLYWFHDKVLKVLSPREEFKITWYMSWSPCFE--CAEQV
human_APOBEC2          ---AAAHAEEAFFNTILP----AFDPALRYNVTWYVSSSPCAA--CADRI
human_A3G_ctd*198-384  GFLEGRHAELCFLDVIPF---WKLDLDQDYRVTCFTSWSPCFS--CAQEM
                         *   *  *:  .          :   : :* : * ***    **  :

human_A3A              RAFLQENTHVRLRIFAARIYDYD---PLYKEALQMLRDAGAQVSIMTYDE
human_A3B_ctd          RAFLQENTHVRLRIFAARIYDYD---PLYKEALQMLRDAGAQVSIMTYDE
human_AID              ADFLRGNPNLSLRIFTARLYFCE-DRKAEPEGLRRLHRAGVQIAIMTFKD
human_A3C              AEFLARHSNVNLTIFTARLYYFQ--YPCYQEGLRSLSQEGVAVEIMDYED
human_A3F_ctd          AEFLARHSNVNLTIFTARLYYFW--DTDYQEGLRSLSQEGASVEIMGYKD
cow_A3F_ntd            ADFLGRHQNVTLSIFTSRLYKFQ--EEGSRQGLLRLSDQGAHVDIMSYQE
sheep_A3F_ntd          AGFLGMYQNVTLSIFTARLYYFQ--KPQYRKGLLRLSDQGACVDIMSYQE
pig_A3F_ntd            AQFLEENRNVSLSLSAARLYYFW--KSESREGLRRLSDLGAQVGIMSFQD
mouse_A3_ntd           LRFLATHHNLSLDIFSSRLYNIR--DPENQQNLCRLVQEGAQVAAMDLYE
human_APOBEC2          IKTLSKTKNLRLLILVGRLFMWE--EPEIQAALKKLKEAGCKLRIMKPQD
human_A3G_ctd*198-384  AKFISKNHVSLCIFTARIYDDQ---GRCQEGLRTLAEAGAKISIMTYSE
                          :       ::  * :   .*::                *    *    :

human_A3A              FKHCWDTFVDHQG---CPFQPWDGLDEHSQALSGRLRAILQNQGN-----
human_A3B_ctd          FEYCWDTFVYRQG---CPFQPWDGLEEHSQALSGRLRAILQNQGN-----
human_AID              YFYCWNTFVENHE---RTFKAWEGLHENSVRLSRQLRRILLPLYEVDDLR
human_A3C              FKYCWENFVYNDN---EPFKPWKGLKTNFRLLKRRLRESLQ---------
human_A3F_ctd          FKYCWENFVYNDD---EPFKPWKGLKYNFLFLDSKLQEEILE--------
cow_A3F_ntd            FKYCWKKFVYSQR---RPFRPWKKLDRNYQRLVEEELEDILGNT------
sheep_A3F_ntd          FKYCWKKFVYSQR---RPFRPWKKLKRNYQLLAAELEDILGNT------
pig_A3F_ntd            FQHCWNNFVHNLG---MPFQPWKKLHKNYQRLVTELKQILRNT-------
mouse_A3_ntd           FKKCWKKFVDNGG---RRFRPWKKLLTNFRYQDSKLQEILRPC-------
human_APOBEC2          FEYVWQNFVEQEEGESKAFQPWEDIQENFLYYEEKLADILK---------
human_A3G_ctd*198-384  FKHCWDTFVDHQG---CPFQPWDGLDEHSQDLSGRLRAILQNQEN-----
                         :   * ..**       *:.*. :  :             .*   *
```

FIG 16A

```
   1 ctgccagggg gagggcccca gagaaaacca gaaagagggt gagagactga ggaagataaa
  61 gcgtcccagg gcctcctaca ccagcgcctg agcaggaagc gggaggggcc atgactacga
 121 ggccctggga ggtcacttta gggagggctg tcctaaaacc agaagcttgg agcagaaagt
 181 gaaaccctgg tgctccagac aaagatctta gtcggctgacta gccggccaag gatgaagcct
 241 cacttcagaa acacagtgga gcgaatgtat cgagacacat tctcctacaa cttttataat
 301 agacccatcc tttctcgtcg aataccgtc tggctgtgct acgaagtgaa aacaaagggt
 361 ccctcaaggc cccctttgga cgcaaagatc tttcgaggcc aggtgtattc cgaacttaag
 421 taccacccag agatgagatt cttccactgg ttcagcaagt ggaggaagct gcatcgtgac
 481 caggagtatg aggtcacctg gtacatatcc tggagcccct gcacaaagtg tacaagggat
 541 atggccacgt cctggccga ggaccgaag gttaccctga ccatcttcgt tgcccgcctc
 601 tactacttct gggacccaga ttaccaggag gcgcttcgca gcctgtgtca gaaaagagac
 661 ggtccgcgtg ccaccatgaa gatcatgaat tatgacgaat tcagcactg ttggagcaag
 721 ttcgtgtaca gccaaagaga gctatttgag ccttggaata atctgcctaa atattatata
 781 ttactgcaca tcatgctggg ggagattctc agacactcga tggatccacc cacattcact
 841 ttcaacttta caatgaacc ttgggtcaga ggacggcatg agacttacct gtgttatgag
 901 gtggagcgca tgcacaatga cacctgggtc ctgctgaacc agcgcagggg ctttctatgc
 961 aaccaggctc cacataaaca cggtttcctt gaaggccgcc atgcagagct gtgcttcctg
1021 gacgtgattc ccttttggaa gctggacctg gaccaggact acaggttac ctgcttcacc
1081 tcctggagcc cctgcttcag ctgtgccag gaaatggcta aattcatttc aaaaaacaaa
1141 cacgtgagcc tgtgcatctt cactgcccgc atctatgatg atcaaggaag atgtcaggag
1201 gggctgcgca ccctggccga ggctgggcc aaaatttcaa taatgacata cagtgaattt
1261 aagcactgct gggacacctt tgtggaccac cagggatgtc ccttccagcc ctgggatgga
1321 ctagatgagc acagccaaga cctgagtggg aggctgcggg ccattctcca gaatcaggaa
1381 aactgaagga tgggcctcag tctctaagga aggcagagac ctgggttgag cctcagaata
1441 aaagatcttc ttccaagaaa tgcaaacagg ctgttcacca ccatctccag ctgatcacag
1501 acaccagcaa agcaatgcac tcctgaccaa gtagattctt taaaaatta gagtgcatta
1561 ctttgaatca aaatttat tatatttcaa gaataaagta ctaagattgt gctcaataca
1621 cagaaaagtt tcaaacctac taatccagcg acaatttgaa tcggttttgt aggtagagga
1681 ataaatgaa atactaaatc tttctgtaaa aaaaaaa (SEQ ID NO:1)
```

FIG 16B

```
  1 MKPHFRNTVE RMYRDTFSYN FYNRPILSRR NTVWLCYEVK TKGPSRPPLD AKIFRGQVYS
 61 ELKYHPEMRF FHWFSKWRKL HRDQEYEVTW YISWSPCTKC TRDMATFLAE DPKVTLTIFV
121 ARLYYFWDPD YQEALRSLCQ KRDGPRATMK IMNYDEFQHC WSKFVYSQRE LFEPWNNLPK
181 YYILLHIMLG EILRHSMDPP TFTFNFNNEP WVRGRHETYL CYEVERMHND TWVLLNQRRG
241 FLCNQAPHKH GFLEGRHAEL CFLDVIPFWK LDLDQDYRVT CFTSWSPCFS CAQEMAKFIS
301 KNKHVSLCIF TARIYDDQGR CQEGLRTLAE AGAKISIMTY SEFKHCWDTF VDHQGCPFQP
361 WDGLDEHSQD LSGRLRAILQ NQEN (SEQ ID NO:2)
```

FIG 20A

```
   1 ttccctttgc aattgccttg ggtcctgccg cacagagcgg cctgtcttta tcagaggtcc
  61 ctctgccagg gggagggccc cagagaaaac cagaaagagg gtgagagact gaggaagata
 121 aagcgtccca gggcctccta caccagcgcc tgagcaggaa gggggagggg ccatgactac
 181 gaggccctgg gaggtcactt tagggagggc tgtcctgaaa cctggagcct ggagcagaaa
 241 gtgaaaccct ggtgctccag acaaagatct tagtcgggac tagccggcca aggatgaagc
 301 ctcacttcag aaacacagtg gagcgaatgt atcgagacac attctcctac aactttata
 361 atagacccat cctttctcgt cggaataccg tctggctgtg ctacgaagtg aaaacaaagg
 421 gtccctcaag gccccgtttg gacgcaaaga tctttcgagg ccaggtgtat tcccagcctg
 481 agcaccacgc agaaatgtgc ttcctctctt ggttctgtgg caaccagctg cctgcttaca
 541 agtgtttcca gatcacctgg tttgtatcct ggaccccctg cccggactgt gtggcgaagc
 601 tggccgaatt cctggctgag caccccaatg tcaccctgac catctccgcc gcccgcctct
 661 actactactg ggaaagagat taccgaaggg cgctctgcag gctgagtcag gcaggggccc
 721 gcgtgaagat tatggacgat gaagaatttg catactgctg gaaaactttt gtgtacagtg
 781 aaggtcagcc attcatgcct tggtacaaat cgatgacaa ttatgcattc ctgcaccgca
 841 cgctaaagga gattctcaga aacccgatgg aggcaatgta tccacacata ttctacttcc
 901 actttaaaaa cctacgcaaa gcctatggtc ggaacgaaag ctggctgtgc ttccaccatgg
 961 aagttgtaaa gcaccactca cctgtctcct ggaagagggg cgtcttccga accaggtgg
1021 atcctgagac ccattgtcat gcagaaaggt gcttcctctc ttggttctgt gacgacatac
1081 tgtctcctaa cacaaactac gaggtcacct ggtacacatc ttggagccct tgcccagagt
1141 gtgcagggga gtggccgag ttcctggcca ggcacagcaa cgtgaatctc accatcttca
1201 ccgcccgcct ctactactc tgggatacag attaccagga ggggctccgc agcctgagtc
1261 aggaaggggc ctccgtggag atcatgggct acaaagattt taaatattgt tgggaaaact
1321 ttgtgtacaa tgatgatgag ccattcaagc cttggaaagg actaaaatac aactttctat
1381 tcctggacag caagctgcag gagattctcg agtgagggt ctccccgggc tcatggtct
1441 gtctcctcta gcctcctgct catgttgtgc aggcctcccc tccatcctgg accagctgtg
1501 cttttgcctg tcatcctga gcccctcctg gcctcaggc cattccatag tgctcccctg
1561 cctcaccacc tcctctccgc tctcccaggc tcttcctgca gaggcctctt tctgcctcca
1621 tggctatcca tccacccacc aagaccctgt tccctgagcc tgcatgcccc taacctgcct
1681 tttcccatct ccccagcata acctaatatt tttttttttt tttgagacg gaatttcgct
1741 ctgtcaccca gactggagtg caatggcttg atcttggctc actgcaaact ctgcctacca
1801 ggttcaagcg attctcctgc ctccgcctcc cgagtagctg gaattacaga cgcctgccac
1861 cacgcacagc taactttttt ttttttgta ttttagtag tgactgggtt tcaccatgtt
1921 ggccaggctg tcttgaact cctgacctca ggtgatccgc ctatctcagc ctcccaaagt
1981 gctgggatta caggcgtgag ccactggccc ggcggcacaa ccaaatctta ttaaactcac
2041 cctaggctgg ccgcggtgac tcatgcctat aatccccag caatttggga ggcagaggtg
2101 agagaatcgc ttgagcccag gaattcgaga ccagcctggg ccacatgaca aagccccatc
2161 tctacaaaaa aattacaaaa aaaaaaaaa caggtgtggt ggcatgcacc tgtagttgaa
2221 gctacttgga aggatgaagt gggaggattg cttgagccgg ggaggtggag gctgcagtga
2281 actgagatca cgtcactgaa ctccagtctg agcaacagat cgagaccctg cctgaaaata
2341 aatcaataaa taaactcaac cgaaatgggt atgaaagttg aaatgggtat gtaagttgaa
2401 aaccagaagt tttgagaaac atcctttgtt aactttcatc ctacaaattg ggtcattcat
2461 gtcctacgca gctaaacag agcccaggag ccagggagga aaagcagtca ggccacacac
2521 cattgctccc aaaatggact tctctgcaag cctgactcct gaaactgtgc attgtaccct
2581 gaaaccagct ttatccatag cttctgcaat aaatggctgt aagtcttgga ctccttgcta
2641 taatcgcagc tattcagcaa tggaacctcc cagttcccaa ccttcctag tgcccatggg
2701 cttttcccata ggacaagaga acatttctcc ttttctttt tttttcttt gaaatggagt
2761 ctcgccctgt cacccaggct ggagtgcaat ggtgcggtct cggctcactg caacctctgc
2821 ctcccttgtt caagtgattc tcctgtctca gcctcccgag tagctgggat tacaggcgtc
2881 caccaccaaa ccaggctaat ttttgtattt tcataaaaa cgggtttcat catgtttccc
2941 aggctggtct tattttatt ttattttg agatggagtc ttgctctgtt gcccaggctg
3001 gggtgcagtg gtgcaatctg ggttcactgc agcctctgcc gcctgagttc aagctatttt
3061 cctacctaag cctcccaagt agctggatt acatgcgcgt gccaccacgc ctagctaatt
3121 tttgtgtttt tagtagagac ggggtttcaa catcttgacc aggctggtct tgaactcctg
3181 acctcgtgat ccacccgtct cggcctccca aagtgctggg attacaggcg tgagccacct
3241 ggccaggctt aggctggtct taaactcctg acctcaagtg atccaacctc cttggcctcc
```

FIG 20A (Continued)

```
3301 caaattgctg ggattgctgg tgtgagccac agcgcctagc ccatttctcc ttttaatagg
3361 acctgttgct gtctctgttc tcccaacatg gtgaacacca cccggactgc gtgtatgtcc
3421 caaattacaa ttctttcttt gcaaatgaaa tgtgaaattt agaggccctt ctccacactt
3481 taaatttgac ttgacatttt ctaggcagat ataagttatt agagaatgag attctctata
3541 aaaatgatcc cttcatgctg tggcctccac agaagatgcc ctgggccagg tgcccacatg
3601 aataatgcgg gccacaggca ggcatttatt ttctcacaga tatggaggct acaagtccaa
3661 ggtggagggg tcggcggggt tgtttgctct gaggccgctc ctcctggatg cagggatcc
3721 cttctggctg tgtcctctgt ggcctttcct ctatgaacct gtactgtacc tctgggtct
3781 ctctgcttcc aaatatcttt tttttttttt tcagacagtt ttgctcttgt tttctaggct
3841 ggagtgcaat ggcacaatct cagctcactg caacctctgc cttccgagtt caagcgattc
3901 tcgtgcctca gcctcctgag tagctgggac tacaggcgtg tgccaccacg cctggctaat
3961 tttgtagttt tagtagagac ggggtttctc catgttgctc aggctggtct tgaactcatg
4021 agctcaggcg atccactctc ctcagcctcc caaagtgctg ggattacaga tataagccac
4081 catacacaac ttttttttt ttttgagatg gagtttcact ctgttgccca ggctggagtg
4141 ctaaatagca gaatcactgc tcactgcaac ctctgcctgc tgggttcaag caattctccc
4201 acctcagcct cctgagtagc tgggattaca gatgcccaga accaatctct gctaattttt
4261 ctattttta gtagagatgg ggtttcactg aggaaggaga ccacctctct cattgtctcc
4321 tatttcagaa ggaagcaaaa agttagaaag atgcagaagt aagatcaatg gccagactgt
4381 ttggcgctgc tacctgggcc tggtagttaa agatcaactc ctgacctgac cgcttgtttt
4441 atctaaagat tccagacatt gtatgaggaa gcattgtgaa actttctggt ctgttctgct
4501 agccccacc actgatgcat gtagccccc agtcacgtag cccacgcttg cacaatctat
4561 cacgacccttt tcacgtggac cccttagaat tgtaagccct taaaagggcc agggacttct
4621 tcagggagct ccaatcttca gatgcaagtc tgtcaacgct cccagctgat taaagcctct
4681 tccttcctaa aaaaaaaaaa aaaaaa
```

FIG 20B

```
  1 mkphfrntve rmyrdtfsyn fynrpilsrr ntvwlcyevk tkgpsrprld akifrgqvys
 61 qpehhaemcf lswfcgnqlp aykcfqitwf vswtpcpdcv aklaeflaeh pnvtltisaa
121 rlyyywerdy rralcrlsqa garvkimdde efaycwenfv ysegqpfmpw ykfddnyafl
181 hrtlkeilrn pmeamyphif yfhfknlrka ygrneswlcf tmevvkhhsp vswkrgvfrn
241 qvdpethcha ercflswfcd dilspntnye vtwytswspc pecagevaef larhsnvnlt
301 iftarlyyfw dtdyqeglrs lsqegasvei mgykdfkycw enfvynddep fkpwkglkyn
361 flfldsklqe ile
```

FIG 23A

```
   1   gaaccatcat taattgaagt gagattttc  tggcctgaga cttgcaggga ggcaagaaga
  61   cactctggac accactatgg acagcctctt gatgaaccgg aggaagtttc tttaccaatt
 121   caaaaatgtc cgctgggcta agggtcggcg tgagacctac ctgtgctacg tagtgaagag
 181   gcgtgacagt gctacatcct tttcactgga ctttggttat cttcgcaata agaacggctg
 241   ccacgtggaa ttgctcttcc tccgctacat ctcggactgg gacctagacc ctggccgctg
 301   ctaccgcgtc acctggttca cctcctggag ccctgctac  gactgtgccc gacatgtggc
 361   cgactttctg cgagggaacc ccaacctcag tctgaggatc ttcaccgcgc gcctctactt
 421   ctgtgaggac cgcaaggctg agcccgaggg gctgcggcgg ctgcaccgcg ccggggtgca
 481   aatagccatc atgaccttca aagattattt ttactgctgg aatacttttg tagaaaacca
 541   tgaaagaact ttcaaagcct gggaagggct gcatgaaaat tcagttcgtc tctccagaca
 601   gcttcggcgc atccttttgc ccctgtatga ggttgatgac ttacgagacg catttcgtac
 661   tttgggactt tgatagcaac ttccaggaat gtcacacacg atgaaatatc tctgctgaag
 721   acagtggata aaaacagtc  cttcaagtct tctctgtttt tattcttcaa ctctcacttt
 781   cttagagttt acagaaaaaa tatttatata cgactcttta aaagatcta  tgtcttgaaa
 841   atagagaagg aacacaggtc tggccaggga cgtgctgcaa ttggtgcagt tttgaatgca
 901   acattgtccc ctactgggaa taacagaact gcaggacctg ggagcatcct aaagtgtcaa
 961   cgttttcta  tgactttag  gtaggatgag agcagaaggt agatcctaaa aagcatggtg
1021   agaggatcaa atgtttttat atcaacatcc tttattattt gattcatttg agttaacagt
1081   ggtgttagtg atagatttt  ctattctttt cccttgacgt ttactttcaa gtaacacaaa
1141   ctcttccatc aggccatgat ctataggacc tcctaatgag agtatctggg tgattgtgac
1201   cccaaaccat ctctccaaag cattaatatc caatcatgcg ctgtatgttt taatcagcag
1261   aagcatgttt ttatgtttgt acaaagaag  attgttatgg gtggggatgg aggtatagac
1321   catgcatggt caccttcaag ctactttaat aaaggatctt aaaatgggca ggaggactgt
1381   gaacaagaca ccctaataat gggttgatgt ctgaagtagc aaatcttctg gaaacgcaaa
1441   ctctttttaag gaagtccta  atttagaaac acccacaaac ttcacatatc ataattagca
1501   aacaattgga aggaagttgc ttgaatgttg gggagaggaa aatctattgg ctctcgtggg
1561   tctcttcatc tcagaaatgc caatcaggtc aaggtttgct acattttgta tgtgtgtgat
1621   gcttctccca aaggtatatt aactatataa gagagttgtg acaaaacaga atgataaagc
1681   tgcgaaccgt ggcacacgct catagttcta gctgcttggg aggttgagga gggaggatgg
1741   cttgaacaca ggtgttcaag gccagcctgg gcaacataac aagatcctgt ctctcaaaaa
1801   aaaaaaaaaa aaaaagaaag agagagggcc gggcgtggtg gctcacgcct gtaatcccag
1861   cactttggga ggccgagccg gcggatcac  ctgtggtcag gagtttgaga ccagcctggc
1921   caacatggca aaaccccgtc tgtactcaaa atgcaaaaat tagccaggcg tggtagcagg
1981   cacctgtaat cccagctact gggaggctg  aggcaggaga atcgcttgaa cccaggaggt
2041   ggaggttgca gtaagctgag atcgtgccgt gcactccag  cctgggcgac aagagcaaga
2101   ctctgtctca gaaaaaaaa  aaaaaagag  agagagag   aagagaaca  atatttggga
2161   gagaaggatg gggaagcatt gcaaggaaat tgtgctttat ccaacaaaat gtaaggagcc
2221   aataagggat ccctatttgt ctcttttggt gtctatttgt ccctaacaac tgtctttgac
2281   agtgagaaaa atattcagaa taaccatatc cctgtgccgt tattacctag caacccttgc
2341   aatgaagatg agcagatcca caggaaaact tgaatgcaca actgtcttat tttaatctta
2401   ttgtacataa gtttgtaaaa gagttaaaaa ttgttacttc atgtattcat ttatatttta
2461   tattattttg cgtctaatga tttttatta  acatgattc  cttttctgat atattgaaat
2521   ggagtctcaa agcttcataa atttataact ttagaaatga ttctaataac aacgtatgta
2581   attgtaacat tgcagtaatg gtgctacgaa gccatttctc ttgatttta  gtaaactttt
2641   atgacagcaa atttgcttct ggctcacttt caatcagtta aataaatgat aaataatttt
2701   ggaagctgtg aagataaaat accaaataaa ataatataaa agtgatttat atgaagttaa
2761   aataaaaaat cagtatgatg gaataaactt (SEQ ID NO:5)
```

FIG. 23B

```
1   MDSLLMNRRK FLYQFKNVRW AKGRRETYLC YVVKRRDSAT SFSLDFGYLR NKNGCHVELL
61  FLRYISDWDL DPGRCYRVTW FTSWSPCYDC ARHVADFLRG NPNLSLRIFT ARLYFCEDRK
121 AEPEGLRRLH RAGVQIAIMT FKDYFYCWNT FVENHERTFK AWEGLHENSV RLSRQLRRIL
181 LPLYEVDDLR DAFRTLGL (SEQ ID NO:6)
```

MODIFIED CYTOSINE DEAMINASES

CROSS-REFERENCE TO RELATED APPLICATIONS

This application claims priority under 35 U.S.C. §119(e) from U.S. Provisional Application Ser. No. 61/063,926, filed Feb. 7, 2008, and from U.S. Provisional Application Ser. No. 61/085,225, filed Jul. 31, 2008, all of which are incorporated herein in their entirety.

STATEMENT AS TO FEDERALLY SPONSORED RESEARCH

This invention was made with government support under grant no. RO1 AI064046 and R21/33 AI073167, awarded by the National Institutes of Health. The federal government has certain rights in the invention.

TECHNICAL FIELD

This document relates to modified cytosine deaminases, and more particularly to modified cytosine deaminases with increased solubility and/or increased DNA cytosine deaminase activity.

BACKGROUND

Human APOBEC family members are important mediators of adaptive and innate immune responses. These proteins are defined by a highly conserved zinc-coordinating motif, $HXE-X_{23-28}-CX_{2-4}C$, in which the histidine and the two cysteines position zinc and the glutamate positions water to promote the nucleophilic deamination of cytosines within single-stranded, polynucleotide substrates (usually DNA). One family member, apolipoprotein B mRNA editing enzyme catalytic polypeptide-like 3G (APOBEC3G (A3G)), was identified as a cellular protein capable of blocking the replication of virion infectivity factor (Vif)-defective HIV-1. A3G inhibits the replication of HIV-1 and other retroviruses by deaminating viral cDNA cytosines to uracils during reverse transcription. Uracils template the incorporation of adenines during the synthesis of the complementary viral DNA strand, and subsequent replication (or DNA repair) ultimately produces strand-specific C/G to T/A transition mutations (hypermutations).

SUMMARY

This document provides modified cytosine deaminase polypeptides, and nucleic acids encoding such modified polypeptides. Naturally-occurring cytosine deaminases such as human APOBEC3G and APOBEC3F are prone to aggregation and precipitation, especially at high concentrations. The modified cytosine deaminase polypeptides described herein have increased solubility and/or increased DNA cytosine deaminase activity relative to corresponding naturally-occurring cytosine deaminases. Modified cytosine deaminases also can have enhanced stability relative to a corresponding naturally-occurring cytosine deaminase. In particular, the modified cytosine deaminase polypeptides described herein have greatly increased solubility relative to corresponding naturally-occurring cytosine deaminases. These modified cytosine deaminases also manifest strong DNA cytosine deaminase activity.

In one aspect, the document provides an isolated polypeptide that includes a cytosine deaminase amino acid sequence that aligns with the amino acid sequence set forth in SEQ ID NO:2, wherein the cytosine deaminase amino acid sequence includes (a) an amino acid other than leucine at the position aligning with position 234 of the amino acid sequence or (b) an amino acid other than phenylalanine at the position aligning with position 310 of the amino acid sequence. The cytosine deaminase amino acid sequence can include (a) an amino acid other than leucine at the position aligning with position 234 of the amino acid sequence and (b) an amino acid other than phenylalanine at the position aligning with position 310 of the amino acid sequence. For example, the cytosine deaminase polypeptide amino acid sequence can include an alanine or a lysine at the position aligning with position 234 of the amino acid sequence. For example, the cytosine deaminase polypeptide amino acid sequence can include an alanine, serine, or a lysine at the position aligning with position 310 of the amino acid sequence. In some embodiments, the cytosine deaminase polypeptide amino acid sequence can include (a) an alanine or a lysine at the position aligning with position 234 of the amino acid sequence and (b) an alanine, serine, or a lysine at the position aligning with position 310 of the amino acid sequence. The cytosine deaminase amino acid sequence further can include (c) an amino acid other than cysteine at the position aligning with position 243 of the amino acid sequence, (d) an amino acid other than cysteine at the position aligning with position 321 of the amino acid sequence, or (e) an amino acid other than cysteine at the position aligning with position 356 of the amino acid sequence.

In some embodiments, the cytosine deaminase amino acid sequence can lack the amino acid residues aligning with residues 1 to 174 of the sequence. In other embodiments, the cytosine deaminase amino acid sequence can lack the amino acid sequences aligning with residues 1 to 197 of the sequence. In other embodiments, a cytosine deaminase amino acid sequence can lack the amino acid sequences aligning with residues 1 to 190 of the sequence. In any embodiment, the cytosine deaminase polypeptide amino acid sequence can include (a) an alanine or lysine at the position aligning with position 234 of the amino acid sequence and/or (b) an alanine, serine, or a lysine at the position aligning with position 310 of the amino acid sequence. The cytosine deaminase amino acid sequence further can include (c) an amino acid other than cysteine at the position aligning with position 243 of the amino acid sequence, (d) an amino acid other than cysteine at the position aligning with position 321 of the amino acid sequence, and (e) an amino acid other than cysteine at the position aligning with position 356 of the amino acid sequence. For example, the cytosine deaminase amino acid sequence can include (c) an alanine or glycine at the position aligning with position 243 of the amino acid sequence, (d) an alanine at the position aligning with position 321 of the amino acid sequence, and (e) an alanine at the position aligning with position 356 of the amino acid sequence.

In another aspect, the document provides a purified mutant cytosine deaminase polypeptide. The mutant cytosine deaminase polypeptide is catalytically active and has enhanced solubility relative to a cytosine deaminase having the amino acid sequence set forth in SEQ ID NO:2. The mutant cytosine deaminase polypeptide can include an amino acid sequence that aligns with the amino acid sequence set forth in SEQ ID NO:2, and wherein the mutant cytosine deaminase amino acid sequence includes (a) an amino acid other than leucine at the position aligning with position 234 of the amino acid sequence, (b) an amino acid other than leucine at the position aligning with position 235 of the amino acid sequence, (c) an amino acid other than phenylalanine at the position aligning with position 241 of the amino acid sequence, (d) an amino acid other than leucine at the position aligning with position 253 of the amino acid sequence, (e) an amino acid other than phenylalanine at the position aligning with position 310 of the amino acid sequence, or (f) an amino acid other than leucine at the position aligning with position 371 of the amino acid sequence. For example, the cytosine deaminase amino acid sequence can include (a) an alanine or a lysine at the position aligning with position 234 of the amino acid sequence, (b) an alanine at the position aligning with position 235 of the amino acid sequence, (c) an alanine at the position aligning with position 241 of the amino acid sequence, (d) an alanine or lysine at the position aligning with position 253 of the amino acid sequence, (e) an alanine, serine, or lysine at the position aligning with position 310 of the amino acid sequence, or (f) an alanine at the position aligning with position 371 of the amino acid sequence.

Any of the mutant cytosine deaminases can lack the amino acid residues aligning with residues 1 to 174, residues 1 to 190, or residues 1 to 197 of SEQ ID NO:2. The cytosine deaminase amino acid sequence can include (a) an alanine or a lysine at the position aligning with position 234 of the amino acid sequence, (b) an alanine at the position aligning with position 235 of the amino acid sequence, (c) an alanine at the position aligning with position 241 of the amino acid sequence, (d) an alanine or lysine at the position aligning with position 253 of the amino acid sequence, (e) an alanine, serine, or lysine at the position aligning with position 310 of the amino acid sequence, or (f) an alanine at the position aligning with position 371 of the amino acid sequence.

In another aspect, the document provides an isolated polypeptide that includes a cytosine deaminase amino acid sequence that aligns with the amino acid sequence set forth in SEQ ID NO:2, wherein the cytosine deaminase amino acid sequence includes (a) an amino acid other than leucine at the position aligning with position 260 of the amino acid sequence, (b) an amino acid other than cysteine at the position aligning with position 261 of the amino acid sequence, (c) an amino acid other than cysteine at the position aligning with position 281 of the amino acid sequence, or (d) an amino acid other than cysteine at the position aligning with position 308 of the amino acid sequence. For example, the cytosine deaminase amino acid sequence can include (a) an alanine or lysine at the position aligning with position 260 of the amino acid sequence, (b) an alanine at the position aligning with position 261 of the amino acid sequence, (c) an alanine at the position aligning with position 281 of the amino acid sequence, or (d) an alanine at the position aligning with position 308 of the amino acid sequence. The cytosine deaminase amino acid sequence further can include (e) an amino acid other than leucine at the position aligning with position 234 of the amino acid sequence or (f) an amino acid other than phenylalanine at the position aligning with position 310 of the amino acid sequence.

The document also features an isolated polypeptide that includes a cytosine deaminase amino acid sequence that aligns with the amino acid sequence set forth in SEQ ID NO:2, wherein the cytosine deaminase amino acid sequence includes (a) an amino acid other than methionine at the position aligning with position 227 of the amino acid sequence, (b) an amino acid other than valine at the position aligning with position 265 of the amino acid sequence, (c) an amino acid other than phenylalanine at the position aligning with position 268 of the amino acid sequence, (d) an amino acid other than leucine at the position aligning with position 273 of the amino acid sequence, or (e) an amino acid other than tyrosine at the position aligning with position 340 of the amino acid sequence.

In another aspect, the document features an isolated nucleic acid encoding a mutant cytosine deaminase polypeptide. The mutant cytosine deaminase polypeptide is catalytically active and has enhanced solubility relative to a cytosine deaminase having the amino acid sequence set forth in SEQ ID NO:2, SEQ ID NO:4, or SEQ ID NO:6. The mutant cytosine deaminase polypeptide can lack the amino acid residues aligning with residues 1 to 174 of SEQ ID NO:2; lack the amino acid sequences aligning with residues 1 to 197 of SEQ ID NO:2; lack the amino acid sequences aligning with residues 1 to 190 of SEQ ID NO:2; lack the amino acid sequences aligning with residues 1 to 184 of SEQ ID NO:4; or lack the amino acid sequences aligning with residues 188 to 198 of SEQ ID NO:6. For example, the mutant cytosine deaminase polypeptide can include an amino acid sequence that aligns with the amino acid sequence set forth in SEQ ID NO:2, and include (a) an alanine or a lysine at the position aligning with position 234 of SEQ ID NO:2, (b) an alanine at the position aligning with position 235 of SEQ ID NO:2, (c) an alanine at the position aligning with position 241 of SEQ ID NO:2, (d) an alanine or lysine at the position aligning with position 253 of SEQ ID NO:2, (e) an alanine, serine, or lysine at the position aligning with position 310 of SEQ ID NO:2, or (f) an alanine at the position aligning with position 371 of SEQ ID NO:2. In other embodiments, the cytosine deaminase amino acid sequence includes (a) an alanine or lysine at the position aligning with position 260 of SEQ ID NO:2, (b) an alanine at the position aligning with position 261 of SEQ ID NO:2, (c) an alanine at the position aligning with position 281 of SEQ ID NO:2, or (d) an alanine at the position aligning with position 308 of SEQ ID NO:2. In some embodiments, a mutant cytosine deaminase amino acid sequence can include (a) a lysine at the position aligning with position 44 of SEQ ID NO:6 and (b) a lysine at the position aligning with position 109 of SEQ ID NO:6. In some embodiments, a mutant cytosine deaminase amino acid sequence can include (a) a lysine, aspartic acid, or glutamic acid residue at the position aligning with position 302 of SEQ ID NO:4, (b) an alanine residue at the position aligning with position 314 of SEQ ID NO:4, or (c) an alanine at the position aligning with position 315 of SEQ ID NO:4. In some embodiments, the mutant cytosine deaminase amino acid sequence includes (a) a lysine, aspartic acid, or glutamic acid residue at the position aligning with position 302 of SEQ ID NO:4, (b) an alanine residue at the position aligning with position 314 of SEQ ID NO:4, and (c) an alanine at the position aligning with position 315 of SEQ ID NO:4

The document also features an isolated nucleic acid encoding a polypeptide that includes a cytosine deaminase amino acid sequence that aligns with the amino acid sequence set forth in SEQ ID NO:2, wherein the cytosine deaminase amino acid sequence includes (a) an amino acid other than leucine at the position aligning with position 234 of the amino acid sequence or (b) an amino acid other than phenylalanine at the position aligning with position 310 of the amino acid sequence.

This document also features an isolated nucleic acid encoding a mutant cytosine deaminase polypeptide, wherein the mutant cytosine deaminase polypeptide is catalytically active and has enhanced solubility relative to a corresponding cytosine deaminase having the amino acid sequence set forth in SEQ ID NO:2, SEQ ID NO:4, or SEQ ID NO:6. The mutant cytosine deaminase can include any of the mutations describes herein.

In yet another aspect, the document features a kit that includes a mutant cytosine deaminase polypeptide. The mutant cytosine deaminase polypeptide can be catalytically active and have enhanced solubility relative to a cytosine deaminase having the amino acid sequence set forth in SEQ ID NO:2, SEQ ID NO:4, or SEQ ID NO:6. The mutant cytosine deaminase can include any of the mutations describes herein. The kit further can include a reagent selected from the group consisting of an antibody, a buffer, a uracil DNA glycosylase, or a nucleic acid.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

This application contains at least one drawing executed in color. Copies of this patent or patent application publication with color drawing(s) will be provided by the Office upon request and payment of the necessary fee.

FIG. 1 is a sequence alignment of human APOBEC3G residues 198-380 (SEQ ID NO:7) and human APOBEC2 residues 48-221 (SEQ ID NO:8). This alignment was used to generate a model three-dimensional structure of APOBEC3Gctd using the homology module program of the InsightII program (Accelrys). The atomic coordinates of the main-chain atoms for residues in red boxes were copied directly from the APOBEC2 structure (PDB 2YNT) and applied to APOBEC3Gctd. Residues located outside of the red boxes were treated as loops and their atomic coordinates were computationally generated. The atomic coordinates of all sidechain heavy atoms were optimized energetically using molecular dynamics calculations (InsightII program, Accelrys). The $Zn^{2+}$ of APOBEC2 was not involved in calculations, but it was subsequently positioned in the APOBEC3Gctd model structure. Therefore, the main-chain atoms of residues involved in Zn-binding were not changed from that of A2 structure. APOBEC3G residues 380-384 and the last residue of A2 are not shown in the alignment.

FIG. 4 contains GST-A3G198-384 expression data. (A) A representative gel showing the soluble (supernatant; S) and insoluble (pellet; P) amounts of GST, GST-A3G198-384 (WT) and 5 mutant derivatives. The S/P ratio of the boxed bands is shown below each lane. The *E. coli* protein(s) that migrates indistinguishably from GST-A3G198-384 was present in every sample and it provided a constant (but lower) background signal. (B) Anti-GST (left panel) and anti-A3G (right panel) immunoblots confirm the identities of the bands boxed in A. (C) Mutants with higher, near equivalent or lower S/P values than those of wild type GST-A3G198-384 are listed. Total protein amounts (S+P) were similar for every construct ([A] and data not shown).

Each histogram bar reports the average median mutation frequency and SEM from 2-5 independent experiments, except the bars for the controls (left Y axis: vector and A3G198-384, n=12; right Y axis: vector and A3G-2K3A, n=13). Histogram bars for two A3G-2K3A derivatives exceeded the right Y-axis [N236A (53+19) and Q322A (61+12); indicated by asterisks]. The primary amino acid sequence matches wildtype A3G and the secondary structure is derived from the observed A3G-2K3A solution structure.

Figure 8:
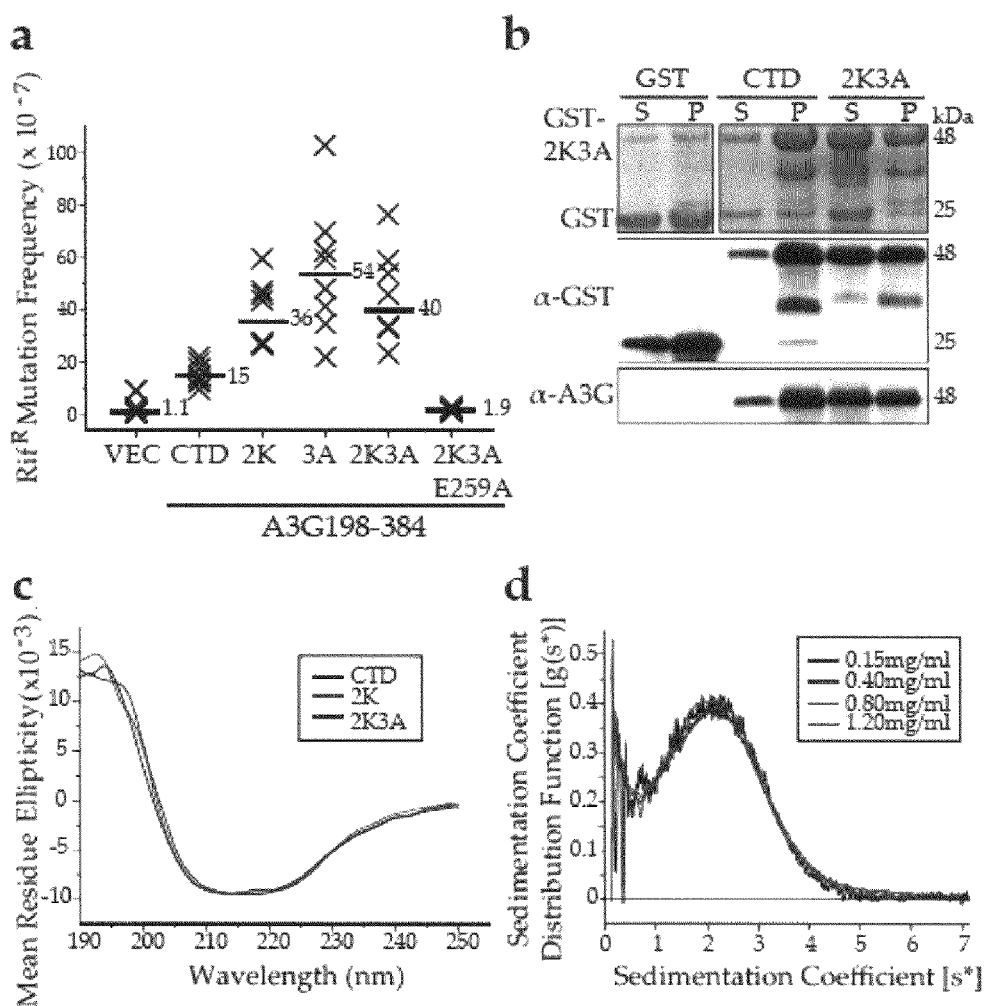

FIG. 8 depicts functional and biophysical properties of A3G-2K3A. FIG. 8a, capacity of GSTA3G198-384 (CTD) and the indicated mutant derivatives to trigger $Rif^R$ mutations in *E. coli*. Each X represents the mutation frequency of an independent culture and the median values are indicated. FIG. 8b, solubility of GST, GST-A3G198-384 (CTD) and GST-A3G-2K3A as monitored by SDS-PAGE and coomassie blue staining (top panels) or immunoblotting (anti-GST middle and anti-A3G bottom panel). FIG. 8c, CD spectra of A3G198-384 (CTD), 2K- and 2K3A-derivatives. FIG. 8d, sedimentation velocity analytical ultracentrifugation profiles for A3G-2K3A. The sedimentation coefficient distribution function g(s*) is shown for various concentrations of A3G-2K3A. The single peak of the g(s*) distribution indicates that A3G-2K3A is homogenous and monomeric.

Figure 9:
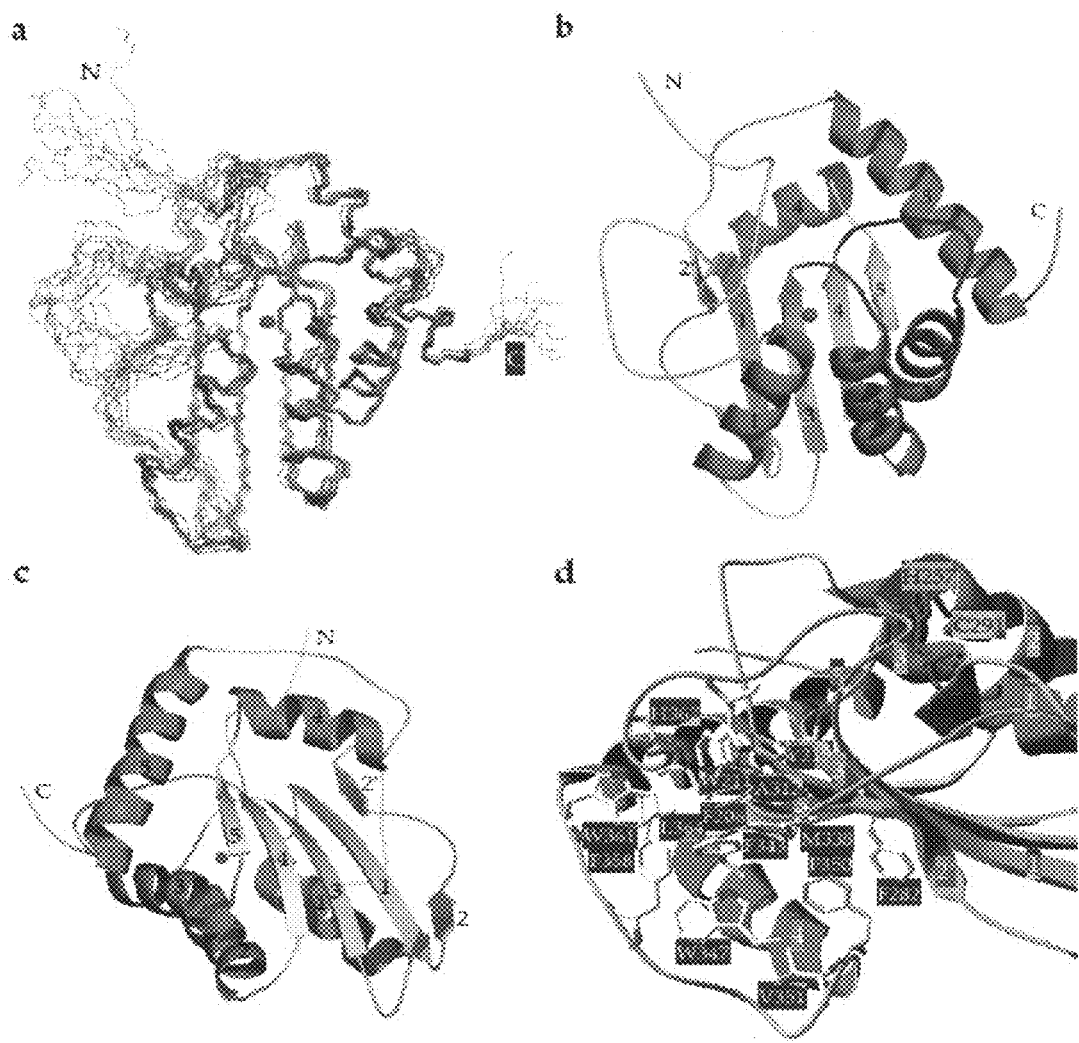

FIG. 9 is the NMR structure of A3G-2K3A (2jyw). FIG. 9a, superimposition of 10

NMR structures showing α-helices in red, β-sheets in yellow and $Zn^{2+}$ in purple. FIGS. 9b and 9c, ribbon-diagrams of the NMR structure shown in (a) from the same and 180° angles, respectively. The β3-to-α2 and β4-to-α3 loops are colored blue in (b) and the β2-bulge-β2' is colored orange in (c). FIG. 9d, hydrophobic contacts between α4 and the β-strands and loops of the indicated regions (β1, β3, β4, N-terminal-loop, β3-α2-loop and β4-α3-loop). Amino acid side chain atoms are colored yellow (sulfur), red (oxygen), blue (nitrogen) and white (carbon). $Zn^{2+}$ binding side chains are colored purple.

FIG. 10 is an alignment of A3G198-384 (SEQ ID NO:9) with selected mammalian APOBEC family members (Clustal W). Residues corresponding to A3G R215, W285 and R313 are highlighted together with homologous residues of family members. Accession numbers: human A3A (NP_663745.1) (SEQ ID NO:10), human A3B (NP_004891.3) (SEQ ID NO:11), human AID (NP_065712.1) (SEQ ID NO:12), human A3C (NP_055323.2) (SEQ ID NO:13), human A3F (AAH38808.1) (SEQ ID NO:14), cow A3F (NM_001077845.1) (SEQ ID NO:15), sheep A3F (NM_001093784.1) (SEQ ID NO:16), pig A3F (NM_001097446.1) (SEQ ID NO:17), mouse A3 (NP_084531.1) (SEQ ID NO:18), human APOBEC2 (NP_006780.1) (SEQ ID NO:19), and human A3G (NP_068594.1). Eight amino acids from the C-terminus of human AID are not shown because they go beyond the aligned region.

Figure 11:
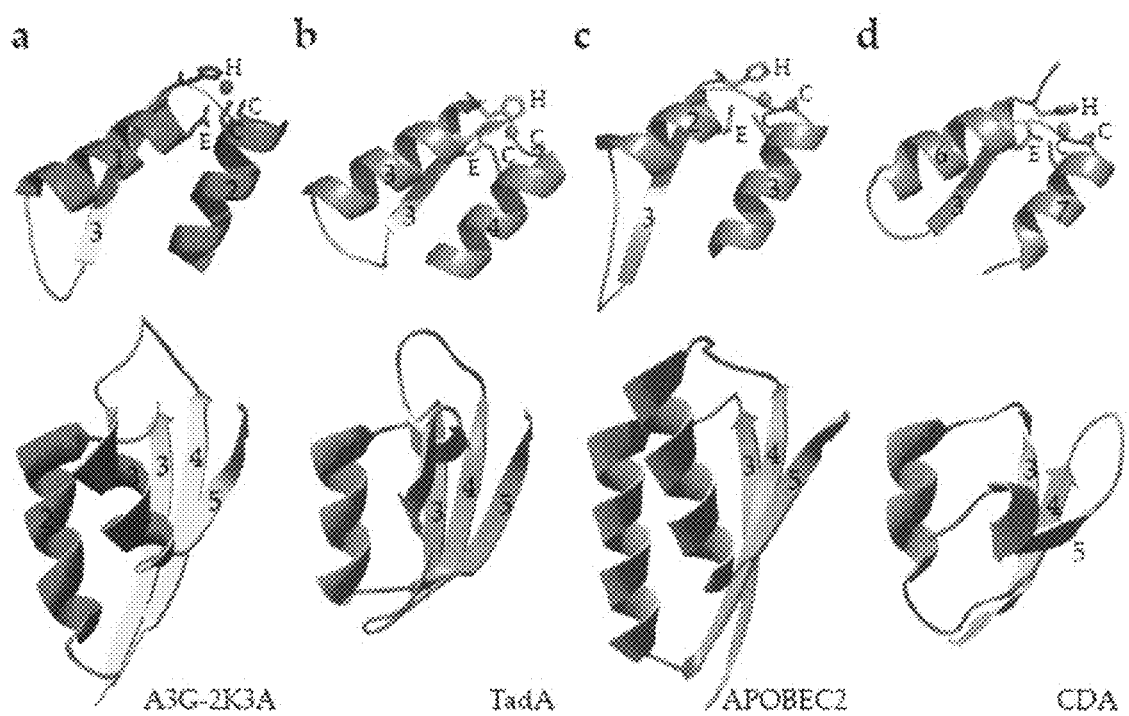

FIG. 11 are structures depicting the relationship of the catalytic domain of APOBEC3G to selected family members. a, b, c, d, human A3G (2jyw), S. aureus TadA (2b3j), human APOBEC2 (2nyt), and E. coli cytidine deaminase (1 ctu) $Zn^{2+}$-binding motifs (top row) and β-strand organization (bottom row). The amino acid side chains of the catalytic glutamate and the $Zn^{2+}$-binding histidine and cysteines are indicated.

Figure 12:
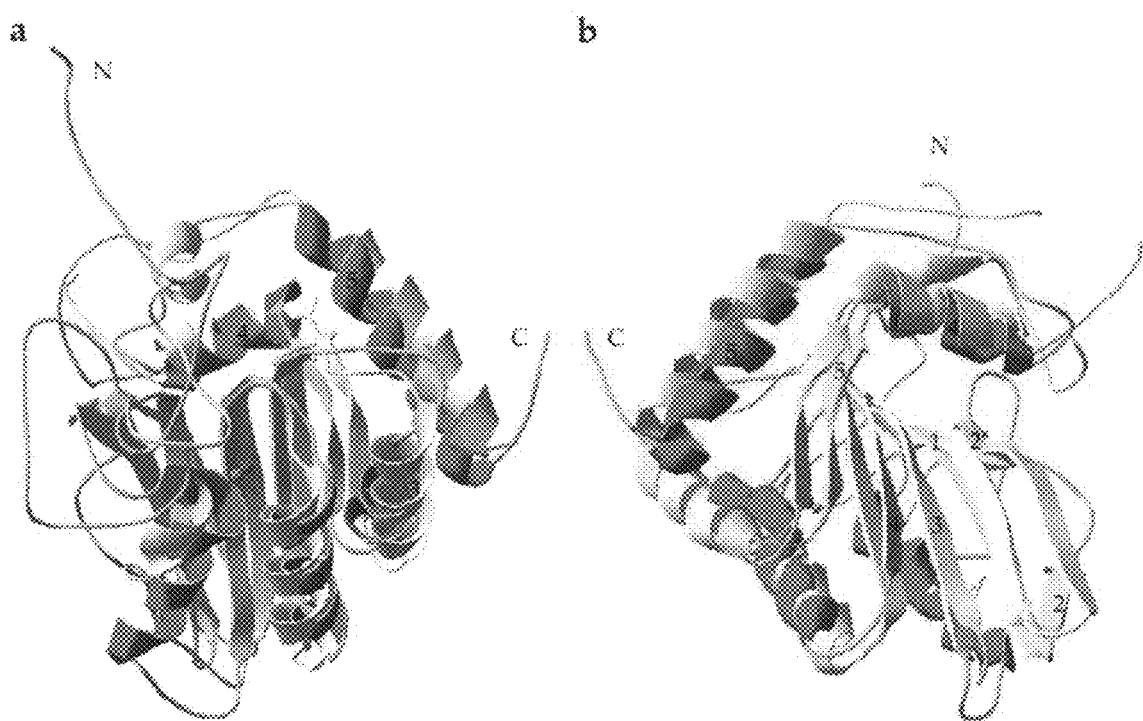

FIG. 12 are ribbon structures of A3G-2K3A and APOBEC2 (PDB 2NYT1). a, view of the zinc-coordinating faces. b, view of the β-sheet cores [rotated approximately 180 degrees around the central axis relative to (a)]. A3G-2K3A secondary structures and termini are colored and numbered. Cα atoms were superimposed to find the minimum r.m.s.d. using the Swiss-Pdb viewer (expasy.org/spdbv/).

Figure 13:
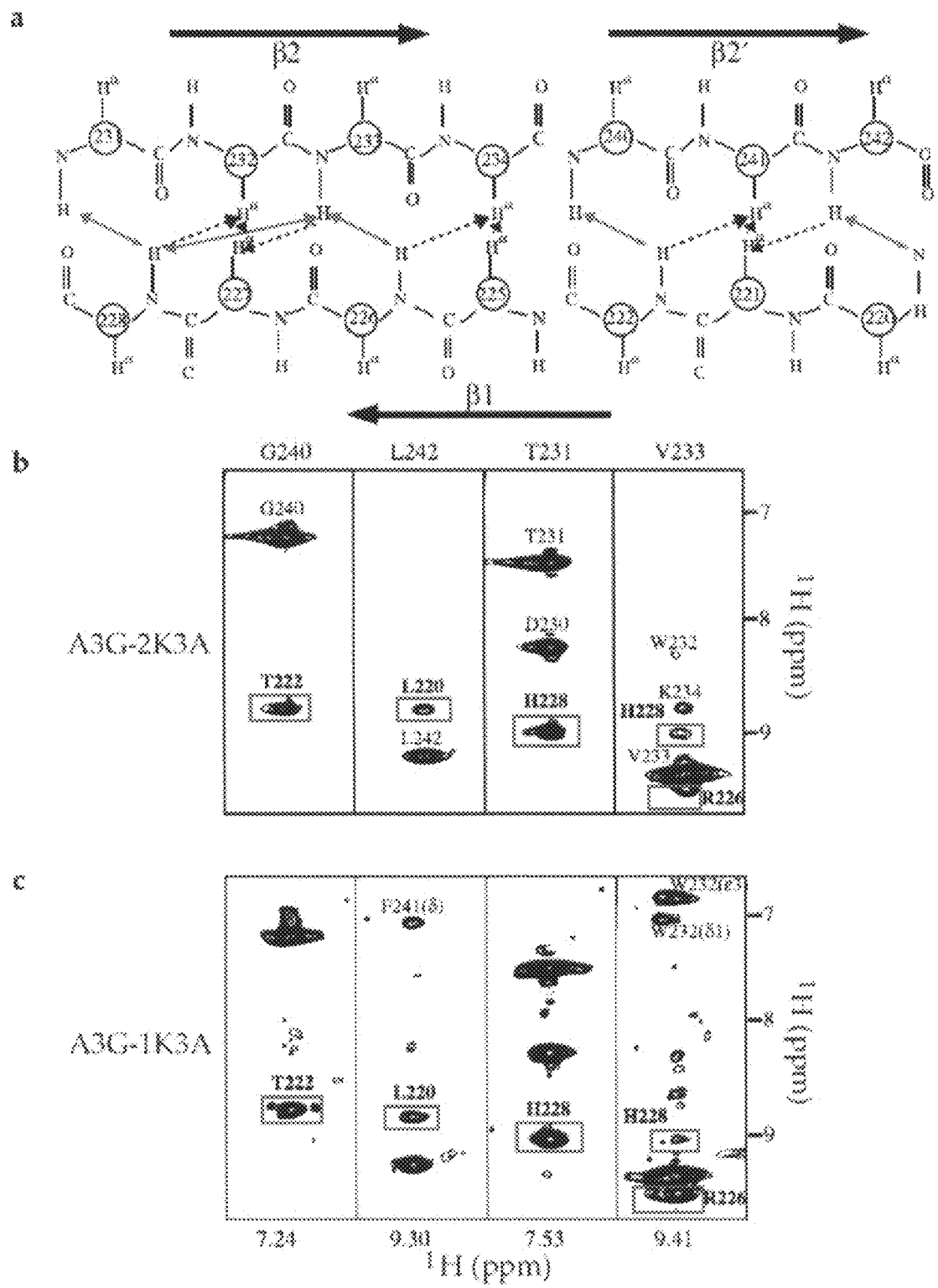

FIG. 13 contains NMR data showing that K234 does not affect the β2-bulge-β2' secondary structure. a, a schematic diagram of the interactions detected between β1 and β2/β2'. Red arrows represent NOE interactions observed in NMR spectra, and they correspond to the boxed signals in (b) and (c). Black, dashed arrows represent observed NOE interactions not shown in (b) and (c). b, representative strips of the $^{15}$N-edited 3D NOESY spectrum of A3G-2K3A showing NOE signals between β1 and β2/β2'. c, representative strips of the $^{15}$N-edited 3D NOESY spectrum of A3G-1K3A showing NOE signals nearly identical to (b).

FIG. 14A-D depict APOBEC3G catalytic domain DNA interaction model. a, surface representation of A3G-2K3A highlighting positions of positive (blue), negative (red) or neutral (white) charge. Arginines that brim the concave active site are labeled. The hypothesized position and polarity of ssDNA is indicated (green dashed line). b, NMR ssDNA-titration data summary (details in FIG. 15). Residues with chemical shift perturbations greater than 1 SD above average are colored green (E259 is perturbed but hidden by H257). H257, C288 and C291 are shaded purple. c, model depicting the interaction between A3G-2K3A and ssDNA (5'-$C_1$-$C_2$-$T_3$-3'). H257 (purple) is shown partially stacked with the ring of the flipped-out target cytosine (C2). W285 (gray) helps form a hydrophobic catalytic cavity. Arginines surrounding the positively charged brim of the active site are indicated (see text for discussion). ssDNA is colored white (carbon), blue (nitrogen), red (oxygen) and yellow (phosphate). d, DNA deaminase activity of A3G-2K3A derivatives. Each X represents the mutation frequency of an independent culture and key median values are indicated (others were at background levels). The Y-axis splits to accommodate the high activity of A3G-2K3A and therefore one CTD data point (52.7) is not shown. The significance of the A versus E substitution at R213 or R320 is indicated (Student's t-test).

Figure 14:
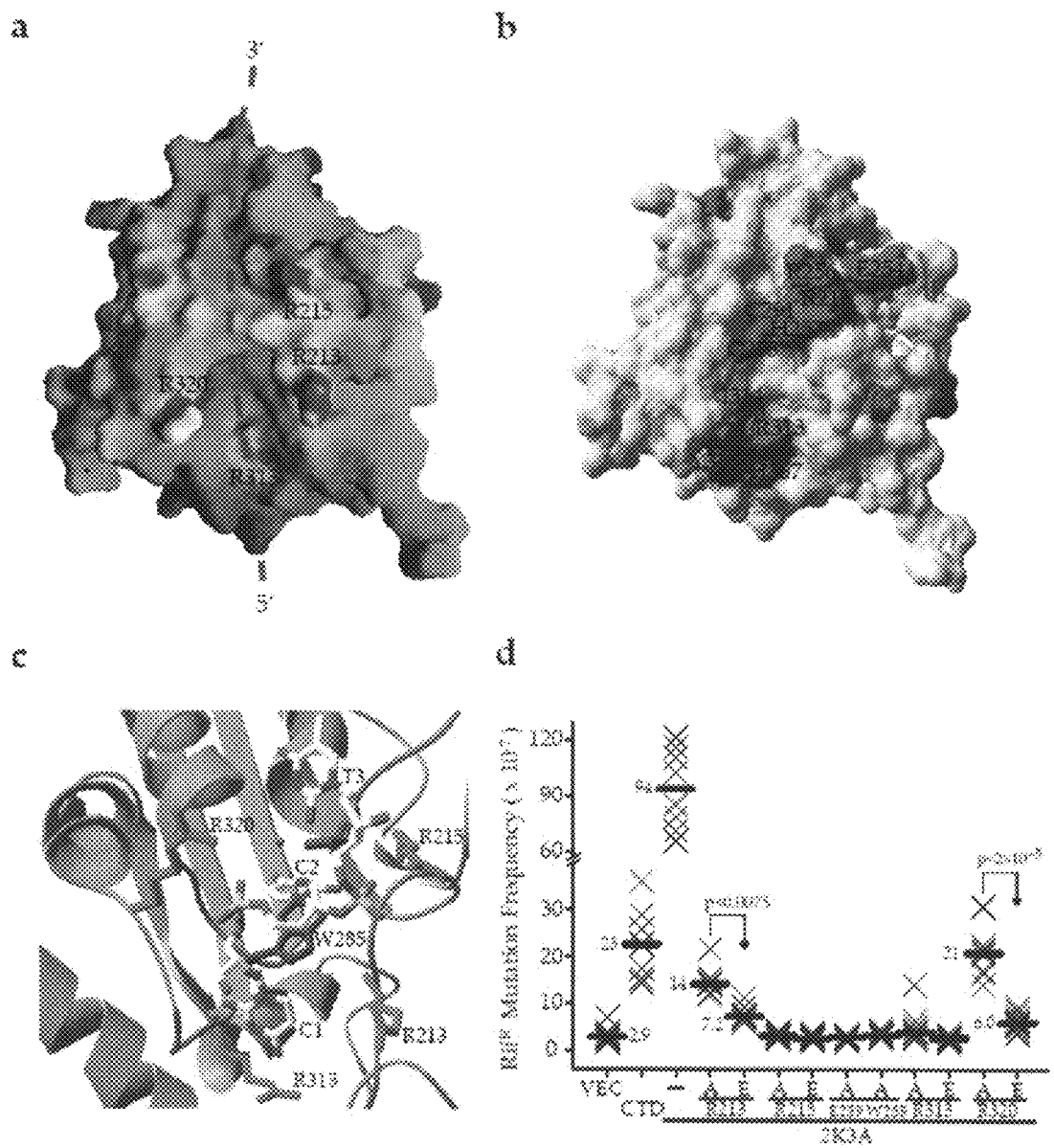
Figure 15:
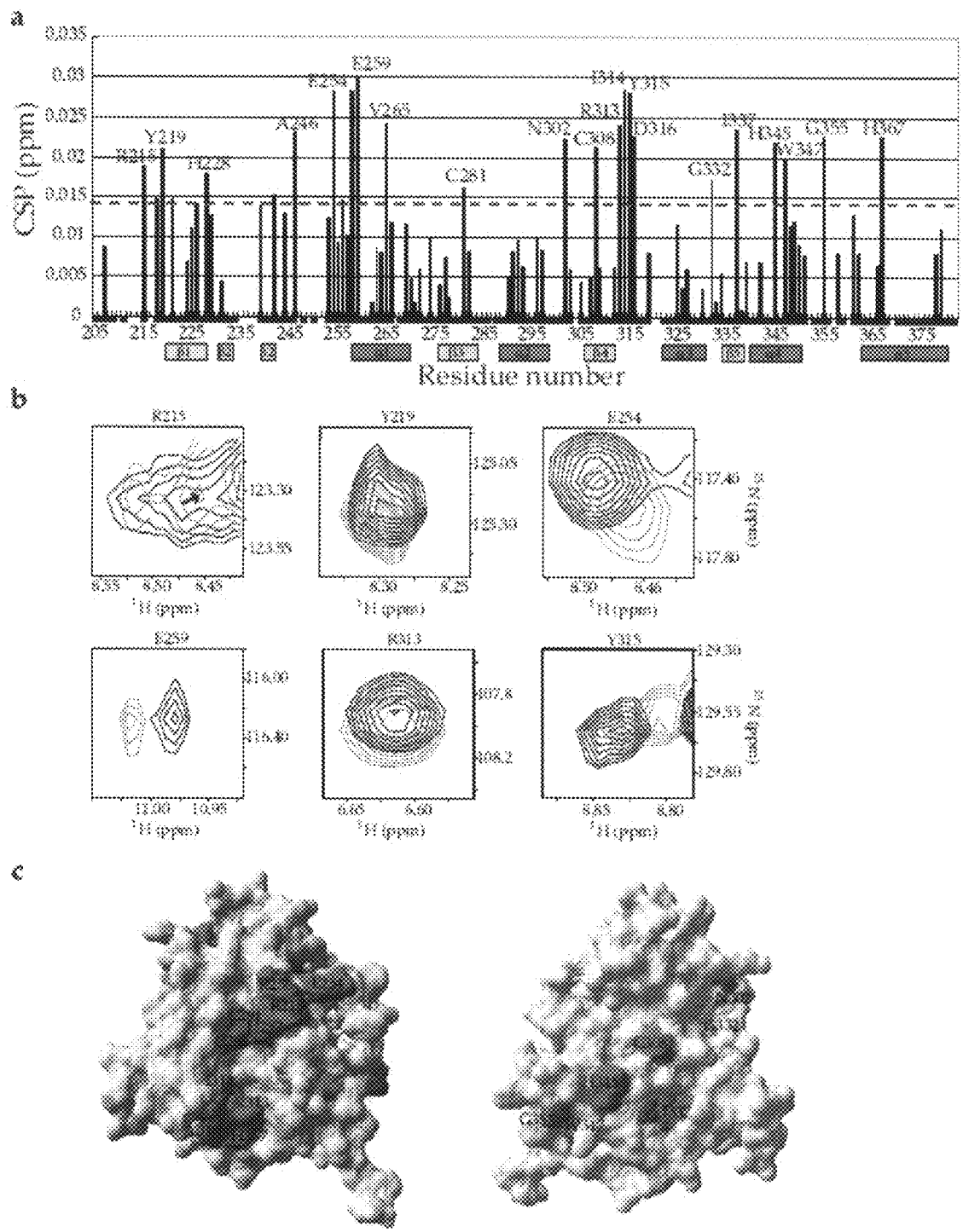

FIG. 15 depicts A3G-2K3A NMR chemical shift perturbations caused by ssDNA. FIG. 15a contains NMR chemical shift perturbation data for A3G-2K3A incubated with a ssDNA (5'-GCT TCT TCT ACC TTC TCT TGA-3', SEQ ID NO:252) at a molar ratio of 1 protein to 4 ssDNA. The chemical shift perturbations (parts per million) are shown for the underlined residues of A3G-2K3A. A schematic of the observed secondary structure is shown for reference. FIG. 15b contains representative A3G-2K3A NMR signal shifts caused by ssDNA. Red and black plots are with and without ssDNA, respectively. FIG. 15c shows ssDNA induced A3G-2K3A NMR chemical shift perturbations occurred predominantly on the active site side of the protein (left panel, identical to FIG. 14b) and not on the opposite side of the protein (right panel).

FIGS. 16A-16B contain the nucleotide sequence (SEQ ID NO:1) encoding human APOBEC3G and the amino acid sequence of human APOBEC3G (SEQ ID NO:2).

FIGS. 17A-17C are graphs depicting $Rif^R$ mutation frequencies ($\times 10^{-7}$) of untagged A3G in E. coli growing under non-inducing conditions (A) or IPTG-induced expression conditions (B), or GST-tagged constructs performed under non-inducing conditions (C). Each X represents the mutation frequency of an independent culture (n=8 per construct). The median mutation frequency for cells expressing the vector control, wild-type (wt), 2K3A, or 2K3A-E259A truncated A3G protein is indicated. Representative anti-A3G immunoblots are shown below, with non-specific (NS) bands providing loading controls. 2K3A derivatives migrate slightly slower. The Y-axis values are different. For C, the complementary IPTG-induced experiment could not be done with the GST expression constructs because induction causes cell death.

FIG. 18A is a schematic view of the major steps of the in vitro deamination assay.

FIG. 18B depict in vitro activity of A3G191-384-2K3A and A3G198-384-2K3A in thessDNA deamination assay. The migration positions of a positive control (PC) and a negative control (NC) are indicated. The top band represents deaminated ssDNA substrate that incurred a 5'-CCC to -CCT transition mutation that protected it from restriction endonuclease digestion and the bottom band represents the restriction-susceptible input substrate (2 products of equal size).

The controls were processed in parallel with the experimental reactions and analyzed as part of the same gel, but non-relevant intervening lanes were removed for presentation.

Figure 19A:
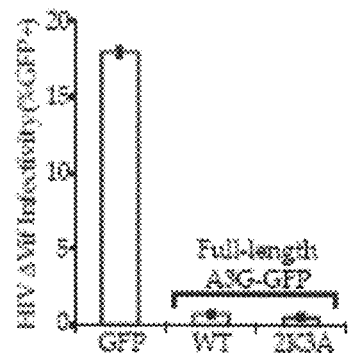

FIG. 19A is a histogram reporting the infectivity of Vif-deficient HIV-1 produced in the presence of a control expression vector, wild-type (WT) A3G or full-length A3G-2K3A.

Figure 19B:
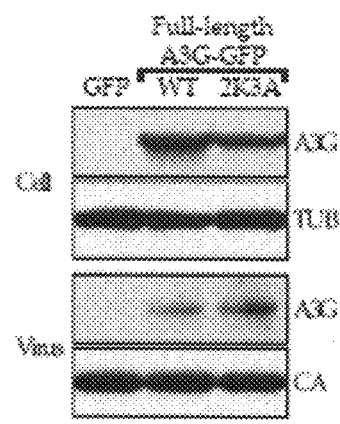

FIG. 19B contains representative immunoblots of cellular and encapsidated wild-type (WT) A3G and full-length A3G-2K3A, with tubulin (TUB) and p24 (CA) as loading controls, respectively.

FIGS. 20A-20B contain the nucleotide sequence (SEQ ID NO:3) encoding human APBEC3F and the amino acid sequence of human APOBEC3F (SEQ ID NO:4), respectively. In FIG. 20A, the coding sequence is from nucleotides 294 to 1415.

Figure 21:
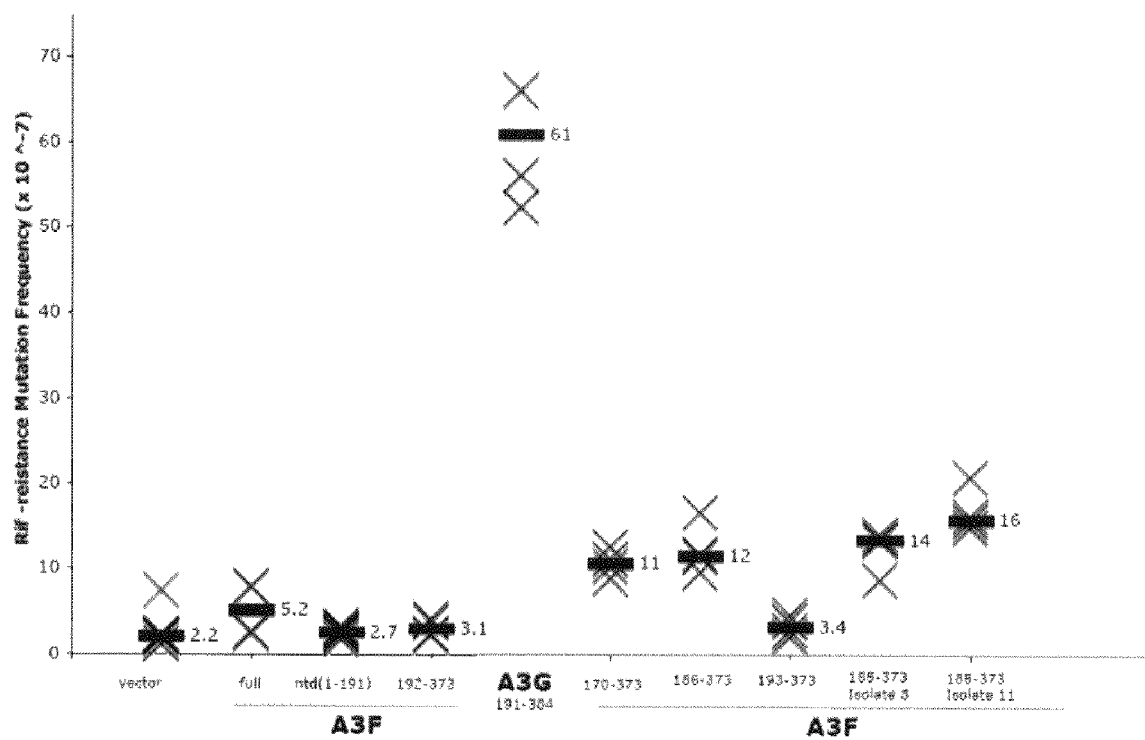

FIG. 21 is a graph depicting $Rif^R$ mutation frequencies ($\times 10^{-7}$) of the indicated GST-A3F or A3G constructs. Each X represents the mutation frequency of an individual culture (n=8 per construct). The median mutation frequency for cells expressing the recited constructs is indicated. ntd(1-191) refers to a construct expressing residues 1-191 (i.e., the N-terminal pseudo catalytic domain). The negative result with ntd(1-191) was predicted.

Figure 22:
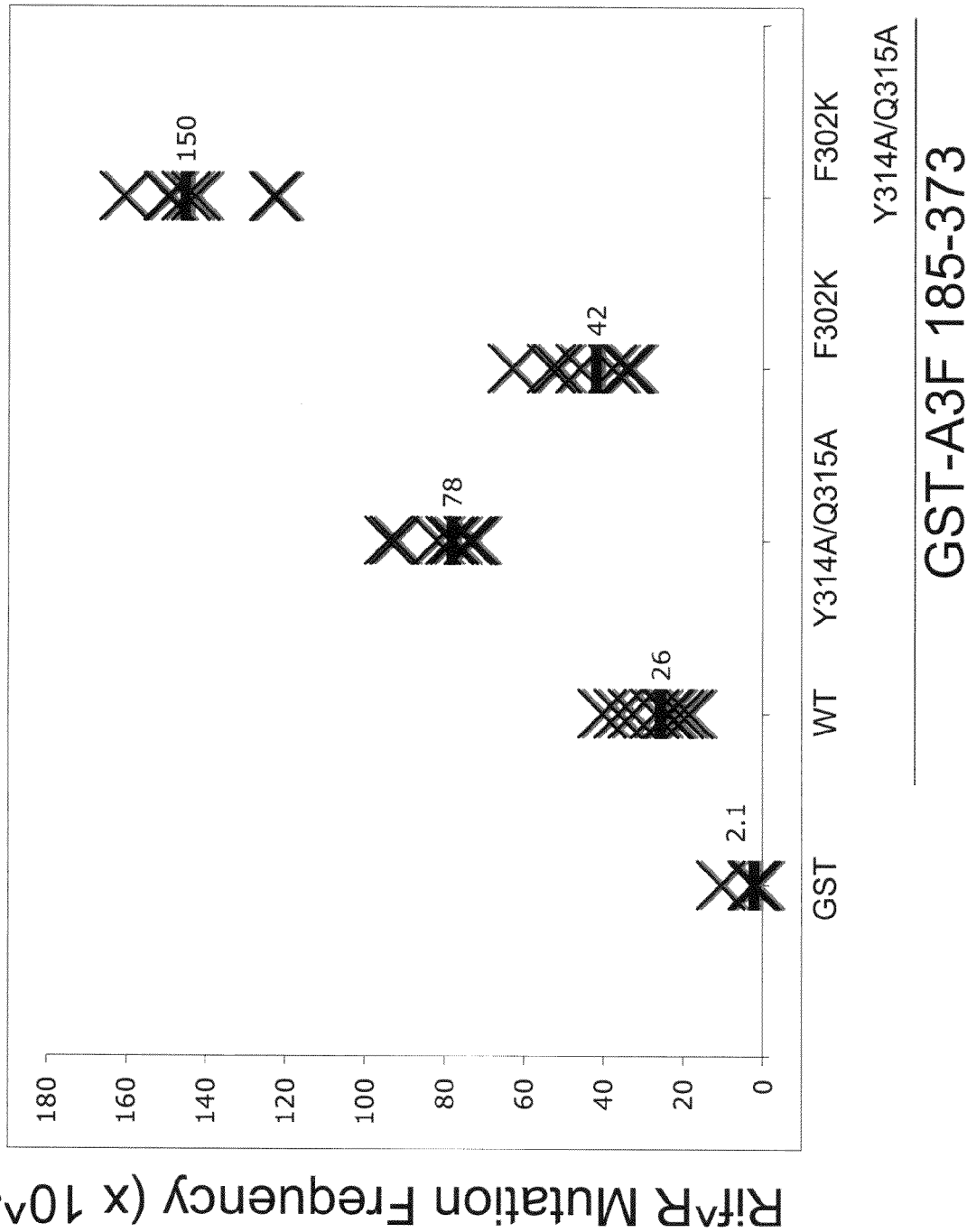

FIG. 22 is a graph depicting $Rif^R$ mutation frequencies ($\times 10^{-7}$) of the indicated A3F constructs.

FIGS. 23A-23B contain the nucleotide sequence (SEQ ID NO:5) encoding human AID and the amino acid sequence of human AID (SEQ ID NO:6), respectively. In FIG. 23A, the coding sequence is from nucleotides 77 to 673.

Figure 24:
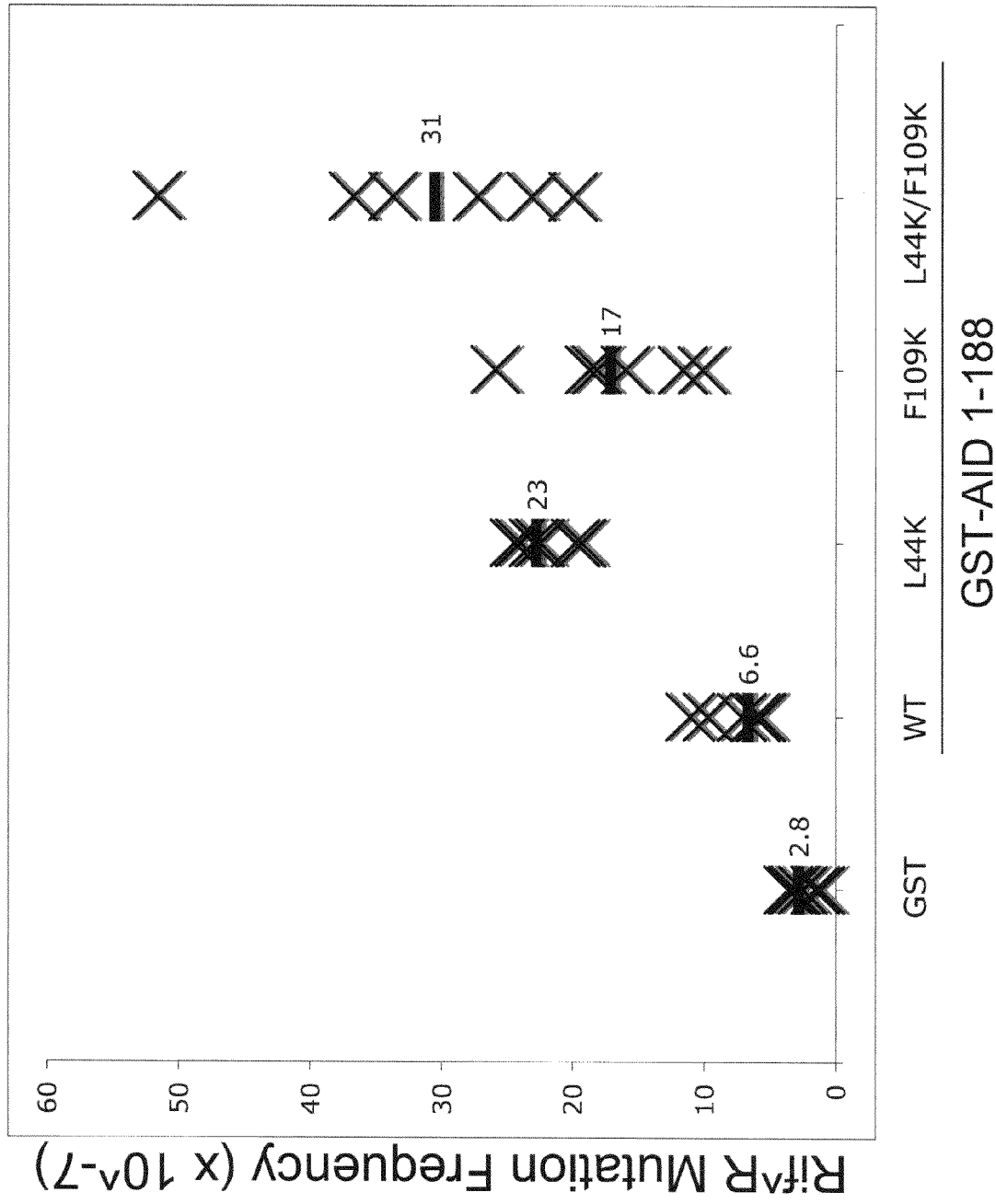

FIG. 24 is a graph depicting $Rif^R$ mutation frequencies ($\times 10^{-7}$) of the indicated AID constructs.

Like reference symbols in the various drawings indicate like elements.

DETAILED DESCRIPTION

In general, the document provides cytosine deaminase polypeptides and nucleic acids encoding cytosine deaminase polypeptides. Non-limiting examples of cytosine deaminase polypeptides include single domain DNA cytosine deaminases and double domain DNA cytosine deaminases. For example, single domain DNA cytosine deaminases include, for example, activation induced deaminase (AID), APOBEC1, APOBEC2, APOBEC3A, APOBEC3C, APOBEC3D, APOBEC3E, and APOBEC3H polypeptides. Double domain DNA cytosine deaminases include, for example, APOBEC3B, APOBEC3F, and APOBEC3G polypeptides. APOBEC3D and APOBEC3E also can be produced as double domain cytosine deaminases. See, e.g., Harris and Liddament (2004), supra; and Jarmuz et al Genomics (2002) 79(3):285-96. APOBEC3G and/or APOBEC3F are particularly useful. Human APOBEC3G (apolipoprotein B mRNA-editing enzyme catalytic polypeptide-like 3G, also known as CEM15) uses cytosine to uracil deamination to inhibit the replication of a variety of retroviruses, including HIV-1. APOBEC3G localizes predominantly to the cytoplasm of mammalian cells. In a retrovirus-infected cell, this localization may facilitate the incorporation of APOBEC3G into viral particles, which are released from the plasma membrane. APOBEC3G also is specifically incorporated into virions through an association with the viral Gag protein and/or viral genomic RNA. Once a retrovirus enters a cell, its genomic RNA is reverse transcribed, and during this process, APOBEC3G is capable of deaminating cDNA cytosines to uracils (C->U). These lesions occur at such a high frequency that they ultimately inactivate the virus (causing G->A hypermutation, as read-out on the genomic strand of the virus). The amino acid sequence of human APOBEC3G is set forth in SEQ ID NO:2; the nucleotide sequence encoding human APOBEC3G is set forth in SEQ ID NO:1 (see FIGS. 16A and 16B). See also GenBank Accession No. NM_021822 for the nucleotide and amino acid sequences of human APOBEC3G. APOBEC3F is a homolog of APOBEC3G and restricts HIV-1 infection by a similar mechanism. The amino acid sequence of human APOBEC3F is set forth in SEQ ID NO:4; the nucleotide sequence encoding human APOBEC3F is set forth in SEQ ID NO:3 (see FIG. 20A and FIG. 20B). See also GenBank Accession No. NM_145298 for the nucleotide sequence encoding human APOBEC3F and GenBank Accession No. NP_660341 for the amino acid sequence of human APOBEC3F. APOBEC3F and -3G deaminate cytosines within different local contexts, preferring 5'-TC and 5'-CC, respectively. The amino acid sequence of human AID is set forth in SEQ ID NO:6; the nucleotide sequence encoding human AID is set forth in SEQ ID NO:5 (see FIGS. 23A and 23B). See also GenBank Accession No. NM_020661 and NP_065712 for the nucleotide and amino acid sequences of human AID, respectively. It is noted that AID is also referred to as "activation-induced cytidine deaminase" (AICDA).

In particular, the document provides nucleic acid molecules that encode cytosine deaminase polypeptides that are heterologous to any naturally occurring cytosine deaminase polypeptide. In some embodiments, the cytosine deaminase polypeptides have increased solubility and/or increased DNA cytosine deaminase activity as compared to a naturally occurring cytosine deaminase polypeptide. For example, a cytosine deaminase polypeptide can have increased solubility relative to a naturally occurring cytosine deaminase and maintain a high level of DNA cytosine deaminase activity. In some embodiments, the cytosine deaminases are not catalytically active. The term "nucleic acid" as used herein encompasses both RNA and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

An "isolated nucleic acid" refers to a nucleic acid that is separated from other nucleic acid molecules that are present in a viral genome, including nucleic acids that normally flank one or both sides of the nucleic acid in a viral genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Nucleic acids described herein encode cytosine deaminase polypeptides that are heterologous to any naturally occurring cytosine deaminase polypeptide (i.e., are "modified" cytosine deaminase polypeptides). The term "cytosine deaminase polypeptide amino acid sequence" as used herein refers to any amino acid sequence that is at least 50 percent (e.g., at least 55, 60, 65, 70, 75, 80, 85, 90, 95, 96, 97, 98, 99, or 100 percent) identical to the sequence set forth in SEQ ID NO:2, SEQ ID NO:4, or SEQ ID NO:6.

The percent identity between a particular amino acid sequence and the amino acid sequence set forth in SEQ ID NO:2, SEQ ID NO:4, or SEQ ID NO:6 is determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid residue is presented in both sequences. The percent identity is determined by dividing the number of matches by the length of the full-length cytosine deaminase polypeptide amino acid sequence followed by multiplying the resulting value by 100. For example, an amino acid sequence that has 300 matches when aligned with the sequence set forth in SEQ ID NO:2 is 78.1 percent identical to the sequence set forth in SEQ ID NO:2 (i.e., 300÷384*100=78.1).

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

A mutation in a nucleic acid molecule described herein can be in any portion of the coding sequence. In some embodiments, the mutation can be in any portion of the coding sequence that renders the encoded cytosine deaminase polypeptide more soluble than the corresponding, naturally occurring cytosine deaminase polypeptide. In other embodiments, the mutation can be in any portion of the coding sequence that renders increased DNA cytosine deaminase activity in the encoded cytosine deaminase polypeptide. Mutations at nucleotides encoding the amino acids at one or more of positions 202, 204, 205, 207, 208, 209, 211, 212, 219, 224, 227, 232, 233, 234, 235, 241, 242, 243, 244, 252, 253, 260, 261, 262, 265, 266, 268, 269, 273, 275, 277, 279, 289, 299, 308, 310, 321, 322, 340, 344, 345, 349, 351, 356, 366, 371, and 378 (relative to SEQ ID NO:2) are particularly useful. See also FIG. 7. Mutations at nucleotides encoding, for example, one or more of amino acids 302, 314, and 315 (relative to SEQ ID NO:4) also are particularly useful as are mutations at nucleotides encoding, for example, one or more of amino acids 44 and 109 (relative to SEQ ID NO:6).

For example, cytosine deaminase polypeptides that include mutations at amino acid positions 234 and/or 310 relative to SEQ ID NO:2 have increased solubility and maintain high levels of DNA cytosine deaminase activity. That is, a cytosine deaminase polypeptide having an amino acid other than leucine at the position aligning with position 234 and/or an amino acid other than phenylalanine at the position aligning with position 310 relative to SEQ ID NO:2 have increased solubility and maintain high levels of DNA cytosine deaminase activity. For example, an alanine, lysine, or serine residue can be substituted for the leucine at position 234 or the phenylalanine at position 310. Cytosine deaminase polypeptides that include mutations at positions aligning with positions 227, 235, 241, 253, 265, 268, 273, 340 or 371 of SEQ ID NO:2 also can have increased solubility. See, for example FIG. 4C and Table 6. For example, an alanine residue can be substituted for the leucine residue at the position aligning with position 235 or 371 of SEQ ID NO:2. An alanine residue can be substituted for phenylalanine at the position aligning with position 241 of SEQ ID NO:2. An alanine or lysine residue can be substituted for the leucine residue at the position aligning with position 253 of SEQ ID NO:2.

Cytosine deaminase polypeptides that include mutations at positions aligning with positions 209, 260, 261, 275, 281, 308, 322, or 366 of SEQ ID NO:2 can have increased DNA cytosine deaminase activity. For example, an alanine or lysine residue can be substituted for the leucine residue at the position aligning with position 260 of SEQ ID NO:2. An alanine residue can be substituted for cysteine at the position aligning with position 261, 281, or 308 of SEQ ID NO:2. An alanine residue can be substituted for glutamic acid at the position aligning with position 209 and/or 366 of SEQ ID NO:2. An alanine residue can be substituted for glutamine at the position aligning with position 275 and/or 322 of SEQ ID NO:2.

Cytosine deaminase polypeptides that include mutations at one or more of amino acid positions aligning with residues 243, 321, and 356 of SEQ ID NO:2 can have reduced inter-molecular disulfide bond formation and increased stability. For example, an alanine or glycine residue can be substituted for the cysteine residues at the positions aligning with positions 243, 321, or 356 of SEQ ID NO:2. In some embodiments, a cytosine deaminase polypeptide can include mutations at residues aligning with residues 234, 243, 310, 321, and 356 of SEQ ID NO:2, and optionally, one or more mutations at residues 209, 275, 322, and 366. Such polypeptides have increased solubility, increased DNA cytosine deaminase activity, and reduced inter-molecular disulfide bond formation. In other embodiments, a cytosine deaminase polypeptide can include mutations at residues aligning with residues 202, 205, 207, 208, 209, 244, 275, 322, 344, 345, 349, or 366 of SEQ ID NO:2. See, for example, Table 7.

In another embodiment, a cytosine deaminase polypeptide includes a mutation at amino acid position 302, 314, and/or 315 relative to SEQ ID NO:4. Such a modified polypeptide can have increased solubility and/or maintain high levels of DNA cytosine deaminase activity. That is, a cytosine deaminase polypeptide having an amino acid other than phenylalanine at the position aligning with position 302 relative to SEQ ID NO:4 can have increased solubility and/or maintain high levels of DNA cytosine deaminase activity. For example, a lysine, aspartic acid, or glutamic acid residue can be substituted for the phenylalanine at position 302. A cytosine deaminase polypeptide also can have an amino acid other than tyrosine at the position aligning with position 314 or an amino acid other than glutamine at the position aligning with position 315 relative to SEQ ID NO:4, and have increased solubility and/or maintain high levels of DNA cytosine deaminase activity. For example, an alanine residue can be substituted at positions 314 and 315. In some embodiments, a modified cytosine deaminase polypeptide includes a lysine residue at the position aligning with position 302 of SEQ ID NO:4, and an alanine residue at the positions aligning with positions 314 and 315 of SEQ ID NO:4.

In another embodiment, a cytosine deaminase polypeptide includes a mutation at amino acid position 44 and/or 109 relative to SEQ ID NO:6 Such a modified polypeptide can have increased solubility and/or maintain high levels of DNA cytosine deaminase activity. That is, a cytosine deaminase polypeptide having an amino acid other than phenylalanine at the position aligning with position 44 relative to SEQ ID NO:6 can have increased solubility and/or maintain high levels of DNA cytosine deaminase activity. For example, a lysine can be substituted for the phenylalanine at position 44. A cytosine deaminase polypeptide also can have an amino acid other than leucine at the position aligning with position 44 relative to SEQ ID NO:6, and have increased solubility and/or maintain high levels of DNA cytosine deaminase activity. For example, a lysine residue can be substituted at positions 44 and 109. In some embodiments, a modified cytosine deaminase polypeptide includes a lysine residue at the positions aligning with positions 44 and 109 of SEQ ID NO:6.

It is noted that cytosine deaminase polypeptides that are less than full-length can still have DNA cytosine deaminase activity. See, Examples 2, 11, and 12. For example, in one embodiment, a cytosine deaminase polypeptide can lack the residues aligning with residues 1 to 174 of SEQ ID NO:2 and still retain DNA cytosine deaminase activity. In another embodiment, a cytosine deaminase polypeptide can lack the residues aligning with residues 1 to 190 of SEQ ID NO:2 and retain DNA cytosine deaminase activity. In another embodiment, a cytosine deaminase polypeptide can lack the residues aligning with residues 1 to 197 of SEQ ID NO:2 and retain DNA cytosine deaminase activity. Thus, any of the mutations described herein can be introduced into a cytosine deaminase polypeptide that lacks residues aligning with residues 1 to 174, 1 to 190, or 1 to 197 of SEQ ID NO:2. For example, a cytosine deaminase polypeptide can have one or more mutations at positions aligning with amino acid positions 234, 243, 310, 321, and 356 of SEQ ID NO:2, and lack the amino acid residues aligning with residues 1 to 174, 1 to 190, or residues 1 to 197 of SEQ ID NO:2.

In another embodiment, a cytosine deaminase polypeptide can lack the residues aligning with residues 1 to 169, residues 1 to 184, residues 1 to 185, or residues 1 to 192 of SEQ ID NO:4. Thus, any of the mutations described herein can be introduced into a cytosine deaminase polypeptide that lacks residues aligning with residues 1 to 169, 1 to 184, residues 1 to 185, or 1 to 192 of SEQ ID NO:4. For example, a cytosine deaminase polypeptide can have one or more mutations at positions aligning with amino acid positions 302, 314, and 315 of SEQ ID NO:4, and lack the amino acid residues aligning with residues 1 to 169, 1 to 184, residues 1 to 185, or 1 to 192 of SEQ ID NO:4.

In still other embodiments, a cytosine deaminase polypeptide can lack the residues aligning with residues 189 to 198 of SEQ ID NO:6 and still retain DNA cytosine deaminase activity. Thus, any of the mutations described herein can be introduced into a cytosine deaminase polypeptide that lacks residues aligning with residues 189 to 198 of SEQ ID NO:6. For example, a cytosine deaminase polypeptide can have one or more mutations at positions aligning with amino acid positions 44 and 109 of SEQ ID NO:6, and lack the amino acid residues aligning with residues 188 to 198 of SEQ ID NO:6.

Nucleic acids encoding cytosine deaminase polypeptides can be modified using common molecular cloning techniques (e.g., site-directed mutagenesis) to generate mutations at such positions. Possible mutations include, without limitation, substitutions (e.g., transitions and transversions), deletions, insertions, and combinations of substitutions, deletions, and insertions. Nucleic acid molecules can include a single nucleotide mutation or more than one mutation, or more than one type of mutation. Polymerase chain reaction (PCR) and nucleic acid hybridization techniques can be used to identify nucleic acids encoding cytosine deaminase polypeptides having altered amino acid sequences.

The document also provides vectors containing nucleic acid that encodes a cytosine deaminase polypeptide. Such vectors can be, without limitation, viral vectors, plasmids, phage, and cosmids. For example, vectors can be of viral origin (e.g., paramyxovirus vectors, SV40 vectors, molecular conjugate vectors, or vectors derived from adenovirus, adeno-associated virus, herpes virus, lentivirus, retrovirus, parvovirus, or Sindbis virus) or of non-viral origin (e.g., vectors from bacteria or yeast). A nucleic acid encoding a cytosine deaminase polypeptide typically is inserted into a vector such that the cytosine deaminase polypeptide is expressed. For example, a nucleic acid provided herein can be inserted into an expression vector. "Expression vectors" can contain one or more expression control sequences (e.g., a sequence that controls and regulates the transcription and/or translation of another sequence. Expression control sequences include, without limitation, promoter sequences, transcriptional enhancer elements, and any other nucleic acid elements required for RNA polymerase binding, initiation, or termination of transcription.

In some embodiments, a nucleic acid sequence encoding a modified cytosine deaminase can include a tag sequence that encodes a "tag" designed to facilitate subsequent manipulation of the encoded polypeptide (e.g., to facilitate localization or detection). Tag sequences can be inserted in the nucleic acid sequence encoding the cytosine deaminase polypeptide such that the encoded tag is located at either the carboxyl or amino terminus of the cytosine deaminase polypeptide. Non-limiting examples of encoded tags include green fluorescent protein (GFP), glutathione S transferase (GST), and Flag™ tag (Kodak, New Haven, Conn.).

Nucleic acid molecules within the scope of the invention can be obtained using any method including, without limitation, common molecular cloning and chemical nucleic acid synthesis techniques. For example, PCR can be used to construct nucleic acid molecules that encode modified cytosine deaminase polypeptides. PCR refers to a procedure or technique in which target nucleic acid is amplified in a manner similar to that described in U.S. Pat. No. 4,683,195, and subsequent modifications of the procedure described therein.

This document also provides modified cytosine deaminase polypeptides, which are heterologous to naturally occurring cytosine deaminase polypeptides. As used here, a "polypeptide" refers to a chain of amino acid residues, regardless of post-translational modification (e.g., phosphorylation or glycosylation). A cytosine deaminase polypeptide described herein has a cytosine deaminase polypeptide amino acid sequence that is at least 50 percent (e.g., at least 55, 60, 65, 70, 75, 80, 85, 90, 95, 99, or 100 percent) identical to the sequence set forth in SEQ ID NO:2, SEQ ID NO:4, or SEQ ID NO:6.

The modified cytosine deaminase polypeptides can have increased solubility and/or increased DNA cytosine deaminase activity as compared to a naturally occurring cytosine deaminase polypeptide. Solubility can be assessed by standard techniques such as those described herein (see Examples 1 and 5). For example, the modified polypeptides can be expressed in a host cell (e.g., *E. coli*). After lysing the cells and separating into supernatant (soluble) and pellet (insoluble) fractions, the amount of modified polypeptide in each fraction can be assessed. For example, each fraction can be separated by SDS-PAGE, and protein levels assessed, e.g., by coomassie blue staining. Immunoblotting can be used to confirm identity of the modified polypeptide. DNA cytosine deaminase activity can be assessed using an *E. coli* based mutation assay. Rifampicin resistance ($Rif^R$) is attributable to base substitution mutations in the *E. coli* RNA polymerase B (rpoB) gene, and it occurs in approximately one of every five million bacterial cells. This assay therefore provides a robust measure of intrinsic DNA cytosine deaminase activity. See, for example, Haché et al. (2005) *J Biol Chem,* 280, 10920-10924; Harris et al. (2002) *Molecular Cell,* 10, 1247-1253. In vitro single strand DNA (ssDNA) deaminase assays also can be performed by incubating a cytosine deaminase with a ssDNA substrate containing a deaminase target site (e.g., 5'-GGGCCC-3' A3G target site). Deamination products can be amplified by PCR, digested with a restriction enzyme which cleaves the deamination substrate but not deamination product, and the amount of deamination product quantified. See, for example, Nowarski et al. (2008) *Nat. Struct. Mol. Biol.* 15(10):1059-1066, and Example 11 herein.

Cytosine deaminase polypeptides described herein typically contain at least one amino acid substitution relative to the corresponding wild type cytosine deaminase polypeptides (e.g., AID, APOBEC1, APOBEC2, APOBEC3A, APOBEC3B, APOBEC3C, APOBEC3D, APOBEC3E, APOBEC3F, APOBEC3G, or APOBEC3H polypeptide). AID, APOBEC3A, APOBEC3B, APOBEC3C, APOBEC3D, APOBEC3E, APOBEC3F, and APOBEC3G are particularly useful. The cytosine deaminase polypeptide can be from any species, e.g., mammals such as humans, non-human primates such as monkeys, baboons, or chimpanzees, horses, cows (cattle or oxen), pigs, sheep, goats, cats, rabbits, guinea pigs, hamsters, rats, gerbils, and mice. See Harris and Liddament (2004), supra; and LaRue et al. (2008) *BMC Mol. Biol.,* 9, 109. Amino acid substitutions can be conservative or non-conservative. Conservative amino acid substitutions replace an amino acid with an amino acid of the same class, whereas non-conservative amino acid substitutions replace an amino acid with an amino acid of a different class. Examples of conservative substitutions include amino acid substitutions within the following groups: (1) glycine and alanine; (2) valine, isoleucine, and leucine; (3) aspartic acid and glutamic acid; (4) asparagine, glutamine, serine, and threonine; (5) lysine, histidine, and arginine; and (6) phenylalanine and tyrosine.

Non-conservative amino acid substitutions may replace an amino acid of one class with an amino acid of a different class. Non-conservative substitutions can make a substantial change in the charge or hydrophobicity of the gene product. Non-conservative amino acid substitutions also can make a substantial change in the bulk of the residue side chain, e.g., substituting an alanine residue for an isoleucine residue. Examples of non-conservative substitutions include the substitution of a basic amino acid for a non-polar amino acid or a polar amino acid for an acidic amino acid. One of ordinary skill in the art will appreciate that similar amino acids can be substituted for the mutants described herein. For example, in addition to an alanine, serine, or lysine residue, any hydrophilic amino acid (e.g., glutamatic acid, glutamine, or arginine) could be substituted for the phenylalanine at position 310. This phenylalanine is found in a conserved motif [Leu-Xaa-(Ile/Leu)-Phe-Xaa-Xaa-Arg-(Leu/Ile)-Tyr] in APOBEC3 family members. Out of 58 APOBEC3 family members (including all human APOBEC3 family members and 10 AID sequences), 49 of 58 sequences contain a phenylalanine at this position, and 54 of 58 sequences contain a hydrophobic residue (phenylalanine, leucine, or tyrosine). This conserved motif can be used to identify the corresponding phenylalanine in other APOBEC3 family members. For example, the phenylalanine at position 310 of APOBEC3G (SEQ ID NO:2) corresponds with the phenylalanine at position 302 of human APOBEC3F (SEQ ID NO:4) and the phenylalanine at position 109 of human AID (SEQ ID NO:6). See, for example, FIG. 10. In addition, the leucine at position 234 of APOBEC3G (SEQ ID NO:2) corresponds with the leucine at position 44 of SEQ ID NO:6.

Amino acid substitutions that are particularly useful can be found at, for example, one or more positions aligning with amino acids 202, 204, 205, 207, 208, 209, 211, 212, 219, 224, 227, 232, 233, 234, 235, 241, 242, 243, 244, 252, 253, 260, 261, 262, 265, 266, 268, 269, 273, 275, 277, 279, 289, 299, 308, 310, 321, 322, 340, 344, 345, 349, 351, 356, 366, 371, and 378 of a cytosine deaminase polypeptide having the amino acid sequence set forth in SEQ ID NO:2. In other embodiments, useful substitutions can be found at, for example, one or more positions aligning with amino acids 302, 314, and 315 of a cytosine deaminase polypeptide having the amino acid sequence set forth in SEQ ID NO:4. In still other embodiments, useful substitutions can be found at, for example, at positions 44 and/or 109 of SEQ ID NO:6.

In some embodiments, a cytosine deaminase polypeptide contains two substitutions, e.g., at positions corresponding to amino acids 234 and 310 of a polypeptide having the amino acid sequence set forth in SEQ ID NO:2. In other embodiments, a cytosine deaminase polypeptide contains four substitutions, e.g., at positions corresponding to amino acids 243, 310, 321, and 356 of a polypeptide having the amino acid sequence set forth in SEQ ID NO:2. In other embodiments, a cytosine deaminase polypeptide contains five substitutions, e.g., at positions corresponding to amino acids 234, 243, 310, 321, and 356 of a polypeptide having the amino acid sequence set forth in SEQ ID NO:2. As discussed above, such mutations also result in increased solubility and/or activity in a polypeptide containing residues 198-384 (i.e., a cytosine deaminase lacking residues corresponding to residues 1-197 of SEQ ID NO:2), a polypeptide containing residues 191-384 (i.e., a cytosine deaminase lacking residues corresponding to residues 1-190 of SEQ ID NO:2), or a polypeptide containing residues 175-384 (i.e., a cytosine deaminase lacking residues 1-174 of SEQ ID NO:2). Such one or more substitutions (1) render the cytosine deaminase polypeptide more soluble than naturally occurring cytosine deaminase polypeptides or (2) confer increased DNA cytosine deaminase activity than a corresponding naturally occurring cytosine deaminase polypeptide. For example, a cytosine deaminase polypeptide containing such one or more substitutions can be more soluble than naturally occurring cytosine deaminase polypeptides and maintain high levels of DNA cytosine deaminase activity than a corresponding naturally occurring cytosine deaminase polypeptide.

Similarly, in other embodiments, cytosine deaminase polypeptides can include three substitutions, e.g., at positions corresponding to positions 302, 314, and 315 of SEQ ID NO:4. As discussed herein, such mutations also result in increased solubility and/or activity in a polypeptide containing residues 185-373 (i.e., a cytosine deaminase lacking residues corresponding to residues 1-184 of SEQ ID NO:4). In other embodiments, cytosine deaminase polypeptides can include two substitutions, e.g., at positions corresponding to 44 and 109 of SEQ ID NO:6. As discussed herein, such mutations also result in increased solubility and/or activity in a polypeptide containing residues 1-188 of SEQ ID NO:6 (i.e., a cytosine deaminase lacking residues corresponding to residues 189-198 of SEQ ID NO:6).

Cytosine deaminase polypeptides can be produced using any method. For example, cytosine deaminase polypeptides can be produced by chemical synthesis. Alternatively, cytosine deaminase polypeptides described herein can be produced by standard recombinant technology using heterologous expression vectors encoding cytosine deaminase polypeptides. Expression vectors can be introduced into host cells (e.g., by transformation or transfection) for expression of the encoded polypeptide, which then can be purified. Expression systems that can be used for small or large scale production of cytosine deaminase polypeptides include, without limitation, microorganisms such as bacteria (e.g., *E. coli* and *B. subtilis*) transformed with recombinant bacteriophage DNA, plasmid DNA, or cosmid DNA expression vectors containing the nucleic acid molecules described herein, and yeast (e.g., *S. cerevisiae*) transformed with recombinant yeast expression vectors containing the nucleic acid molecules described herein. Useful expression systems also include insect cell systems infected with recombinant virus expression vectors (e.g., baculovirus) containing the nucleic acid molecules of the invention, and plant cell systems infected with recombinant virus expression vectors (e.g., tobacco mosaic virus) or transformed with recombinant plasmid expression vectors (e.g., Ti plasmid) containing the nucleic acid molecules described herein. Cytosine deaminase polypeptides also can be produced using mammalian expression systems, which include cells (e.g., primary cells or immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids described herein.

Articles of Manufacture

Isolated nucleic acids and polypeptides described herein can be combined with packaging material and sold as a kit, e.g., for cytosine-specific single strand DNA mutagenesis or dC-to-dU conversion as a biomarker. For example, a modified cytosine deaminase polypeptide can be used for dC-to-dU conversion to facilitate penetration of G/C-rich genomic/repetitive DNA sequences by conventional di-deoxy sequencing or deep sequencing technologies. A modified cytosine deaminase polypeptide also can be used for detecting methylation status or identifying methylated cytosines (e.g., as a complement to bisulfite treatment, which deaminates all C's). Particular cytosine deaminase polypeptides can be chosen on the basis of the dinucleotide deamination specificity/preference of the enzyme. For example, APOBEC3G deaminates 5'CC, A3F deaminates 5'-TC, and AID deaminates 5'(G/A)C). Modified cytosine deaminase polypeptides that are more active, more soluble, and more stable that a corresponding wild-type cytosine deaminase are particularly useful for including in kits, which may be stored for periods of time. For example, a modified cytosine deaminase having substitutions at positions 234, 243, 310, 321, and 356 of SEQ ID NO:2 (e.g., L234K, C243A, F310K, C321A, and C356A) is particularly useful in kits. Other useful modified cytosine deaminases have mutations at positions 209, 275, 322, and 366 of SEQ ID NO:2 (e.g., E209A, Q275A, Q322A, or E366A); mutations at positions 302, 314, and/or 315 of SEQ ID NO:4 (e.g., F302K, Y314A, and Q315A); or mutations at positions 44 and/or 109 of SEQ ID NO:6 (e.g., L44K and F109K) Components and methods for producing articles of manufactures are well known.

Articles of manufacture also may include reagents for carrying out the methods disclosed herein (e.g., a buffer, a uracil DNA glycosylase, an antibody, control nucleic acids, or DNA polymerase). Instructions describing how the polypeptides can be used for cytosine-specific single strand DNA mutagenesis, dC-to-dU conversion, or for detecting methylation status also may be included in such kits.

The invention will be further described in the following examples, which do not limit the scope of the invention described in the claims.

EXAMPLES

Example 1

Materials and Methods

Plasmid constructs: The A3G cDNA used here matches NM_021822. A3G and mutant derivatives were expressed as GST fusion proteins using pGEX6P1 or pGEX6P2 (GE Healthsciences). An EcoRI-SalI DNA fragment from pTrc99A-A3G encoding full-length A3G was sub-cloned directly into pGEX6P1. A3G deletion mutants were constructed by amplifying the relevant A3G coding regions, digesting the resulting PCR products with SmaI and SalI and ligating them into the SmaI and XhoI sites of pGEX6P2. Alanine and lysine mutants were constructed using the QuikChange protocol (Stratagene). Tables 1 and 2 list the oligonucleotides used to create each of the mutants. All constructs were verified by DNA sequencing.

TABLE 1

Oligonucleotides used to construct A3G deletion or alanine mutants.

| Mutant | Oligo 1 (5' to 3') | SEQ ID NO: | Oligo 2 (5' to 3') | SEQ ID NO: |
|---|---|---|---|---|
| 175-344 | NCCCGGGTGGAATAATCTGCCTAAATAT | 20 | NGTCGACTCACTTAAATTCACTGTATGTCAT | 21 |
| 198-344 | NCCCGGGGATCCACCCACATTCACTTTC | 22 | NGTCGACTCACTTAAATTCACTGTATGTCAT | 23 |
| 215-344 | NCCCGGGCGGCATGAGACTTACCTGTGT | 24 | NGTCGACTCACTTAAATTCACTGTATGTCAT | 25 |
| 175-362 | NCCCGGGTGGAATAATCTGCCTAAATAT | 26 | NGTCGACTCAATCCCAGGGCTGGAAGGGACA | 27 |

TABLE 1-continued

Oligonucleotides used to construct A3G deletion or alanine mutants.

| Mutant | Oligo 1 (5' to 3') | SEQ ID NO: | Oligo 2 (5' to 3') | SEQ ID NO: |
|---|---|---|---|---|
| 198-362 | NCCCGGGGATCCACCCACATTCACTTTC | 28 | NGTCGACTCAATCCCAGGGCTGGAAGGGACA | 29 |
| 215-362 | NCCCGGGCGGCATGAGACTTACCTGTGT | 30 | NGTCGACTCAATCCCAGGGCTGGAAGGGACA | 31 |
| 175-384 | NCCCGGGTGGAATAATCTGCCTAAATAT | 32 | NGTCGACCCCATCCTTCAGTTTTCCTG | 33 |
| 198-384 | NCCCGGGGATCCACCCACATTCACTTTC | 34 | NGTCGACCCCATCCTTCAGTTTTCCTG | 35 |
| 215-384 | NCCCGGGCGGCATGAGACTTACCTGTGT | 36 | NGTCGACCCCATCCTTCAGTTTTCCTG | 37 |
| F202A | CGATCCACCCACAGCCACTTTCAACTTTAACAATG | 38 | CATTGTTAAAGTTGAAAGTGGCTGTGGGTGGATCG | 39 |
| F204A | CCACCCACATTCACTGCCAACTTTAACAATGAACC | 40 | GGTTCATTGTTAAAGTTGGCAGTGAATGTGGGTGG | 41 |
| F206A | CCACATTCACTTTCAACGCTAACAATGAACCTTGG | 42 | CCAAGGTTCATTGTTAGCGTTGAAAGTGAATGTGG | 43 |
| E209A | CACTTTCAACTTTAACAATGCACCTTGGGTCAG | 44 | CTGACCCAAGGTGCATTGTTAAAGTTGAAAGTG | 45 |
| W211A | CTTTAACAATGAACCTGCGGTCAGAGGACGGC | 46 | GCCGTCCTCTGACCGCAGGTTCATTGTTAAAG | 47 |
| V212A | CAATGAACCTTGGGCCAGAGGACGGCATG | 48 | CATGCCGTCCTCTGGCCCAAGGTTCATTG | 49 |
| R213A | CAATGAACCTTGGGTCGCAGGACGGCATGAGAC | 50 | GTCTCATGCCGTCCTGCGACCCAAGGTTCATTG | 51 |
| Y219A | GGACGGCATGAGACTGCTCTGTGTTATGAGGTG | 52 | CACCTCATAACACAGAGCAGTCTCATGCCGTCC | 53 |
| L220A | CGGCATGAGACTTACGCGTGTTATGAGGTGGAGC | 54 | GCTCCACCTCATAACACGCGTAAGTCTCATGCCG | 55 |
| C221A | GGCATGAGACTTACCTGGCTTATGAGGTGGAGCGC | 56 | GCGCTCCACCTCATAAGCCAGGTAAGTCTCATGCC | 57 |
| Y222A | GAGACTTACCTGTGTGCTGAGGTGGAGCGCATG | 58 | CATGCGCTCCACCTCAGCACACAGGTAAGTCTC | 59 |
| V224A | CCTGTGTTATGAGGCGGAGCGCATGCAC | 60 | GTGCATGCGCTCCGCCTCATAACACAGG | 61 |
| M227A | GAGGTGGAGCGCGCGCACAATGACACCTG | 62 | CAGGTGTCATTGTGCGCGCGCTCCACCTC | 63 |
| N229A | GGAGCGCATGCACGCTGACACCTGGGTC | 64 | GACCCAGGTGTCAGCGTGCATGCGCTCC | 65 |
| W232A | GCACAATGACACCGCGGTCCTGCTGAACC | 66 | GGTTCAGCAGGACCGCGGTGTCATTGTGC | 67 |
| V233A | CAATGACACCTGGGCCCTGCTGAACCAG | 68 | CTGGTTCAGCAGGGCCCAGGTGTCATTG | 69 |
| L234A | GACACCTGGGTCGCGCTGAACCAGCGC | 70 | GCGCTGGTTCAGCGCGACCCAGGTGTC | 71 |
| L235A | CACCTGGGTCCTGGCGAACCAGGGCAG | 72 | CTGCGCTGGTTCGCCAGGACCCAGGTG | 73 |
| F241A | GCGCAGGGGCGCTCTATGCAACCAGG | 74 | CCTGGTTGCATAGAGCGCCCCTGCGC | 75 |
| L242A | GCGCAGGGGCTTTGCATGCAACCAGGC | 76 | GCCTGGTTGCATGCAAAGCCCCTGCGC | 77 |
| C243A | CGCAGGGGCTTTCTAGCCAACCAGGCTCCAC | 78 | GTGGAGCCTGGTTGGCTAGAAAGCCCCTGCG | 79 |
| F252A | CCACATAAACACGGTGCCCTTGAAGGCCGCC | 80 | GGCGGCCTTCAAGGGCACCGTGTTTATGTGG | 81 |
| L253A | CATAAACACGGTTTCGCTGAAGGCCGCCATGC | 82 | GCATGGCGGCCTTCAGCGAAACCGTGTTTATG | 83 |
| R256A | CGGTTTCCTTGAAGGCGCCCATGCAGAGCTGTG | 84 | CACAGCTCTGCATGGGCGCCTTCAAGGAAACCG | 85 |
| E259A | GAAGGCCGCCATGCAGCGCTGTGCTTCCTGGACG | 86 | CGTCCAGGAAGCACAGCGCTGCATGGCGGCCTTC | 87 |
| L260A | CGCCATGCAGAGGCGTGCTTCCTGGAC | 88 | GTCCAGGAAGCACGCCTCTGCATGGCG | 89 |
| C261A | GCCATGCAGAGCTGGCCTTCCTGGACGTGATTCC | 90 | GGAATCACGTCCAGGAAGGCCAGCTCTGCATGGC | 91 |
| F262A | GCAGAGCTGTGCGCCCTGGACGTGATTC | 92 | GAATCACGTCCAGGGCGCACAGCTCTGC | 93 |

TABLE 1-continued

Oligonucleotides used to construct A3G deletion or alanine mutants.

| Mutant | Oligo 1 (5' to 3') | SEQ ID NO: | Oligo 2 (5' to 3') | SEQ ID NO: |
|---|---|---|---|---|
| L263A | CAGAGCTGTGCTTCGCGGACGTGATTCCC | 94 | GGGAATCACGTCCGCGAAGCACAGCTCTG | 95 |
| V265A | GTGCTTCCTGGACGCGATTCCCTTTTGG | 96 | CCAAAAGGGAATCGCGTCCAGGAAGCAC | 97 |
| I266A | CTTCCTGGACGTGGCTCCCTTTTGGAAGC | 98 | GCTTCCAAAAGGGAGCCACGTCCAGGAAG | 99 |
| F268A | GGACGTGATTCCCGCTTGGAAGCTGGACC | 100 | GGTCCAGCTTCCAAGCGGGAATCACGTCC | 101 |
| W269A | GACGTGATTCCCTTTGCGAAGCTGGACCTGG | 102 | CCAGGTCCAGCTTCGCAAAGGGAATCACGTC | 103 |
| L271A | GATTCCCTTTTGGAAGGCGGACCTGGACCAGGA | 104 | TCCTGGTCCAGGTCCGCCTTCCAAAAGGGAATC | 105 |
| L273A | CTTTTGGAAGCTGGACGCGGACCAGGACTACAG | 106 | CTGTAGTCCTGGTCCGCGTCCAGCTTCCAAAAG | 107 |
| Y277A | CTGGACCAGGACGCCAGGGTTACCTGC | 108 | GCAGGTAACCCTGGCGTCCTGGTCCAG | 109 |
| V279A | CAGGACTACAGGGCTACCTGCTTCACC | 110 | GGTGAAGCAGGTAGCCCTGTAGTCCTG | 111 |
| C281A | GGACTACAGGGTTACCGCCTTCACCTCCTGGAGC | 112 | GCTCCAGGAGGTGAAGGCGGTAACCCTGTAGTCC | 113 |
| F282A | CAGGGTTACCTGCGCCACCTCCTGGAGC | 114 | GCTCCAGGAGGTGGCGCAGGTAACCCTG | 115 |
| W285A | CCTGCTTCACCTCCGCGAGCCCCTGCTTC | 116 | GAAGCAGGGGCTCGCGGAGGTGAAGCAGG | 117 |
| C288A | CTCCTGGAGCCCCGCCTTCAGCTGTGCCCAG | 118 | CTGGGCACAGCTGAAGGCGGGGCTCCAGGAG | 119 |
| F289A | CTGGAGCCCCTGCGCCAGCTGTGCCCAGG | 120 | CCTGGGCACAGCTGGCGCAGGGGCTCCAG | 121 |
| C291A | GCCCCTGCTTCAGCGCTGCCCAGGAAATGGC | 122 | GCCATTTCCTGGGCAGCGCTGAAGCAGGGGC | 123 |
| M295A | CAGCTGTGCCCAGGAAGCGGCTAAATTCATTTCAAAAAACAAAC | 124 | GTTTGTTTTTTGAAATGAATTTAGCCGCTTCCTGGGCACAGCTG | 125 |
| F298A | GTGCCCAGGAAATGGCTAAAGCCATTTCAAAAAACAAACACGTGAGCC | 126 | GGCTCACGTGTTTGTTTTTTGAAATGGCTTTAGCCATTTCCTGGGCAC | 127 |
| I299A | CCAGGAAATGGCTAAATTCGCTTCAAAAAACAAACACGTGAGC | 128 | GCTCACGTGTTTGTTTTTTGAAGCGAATTTAGCCATTTCCTGG | 129 |
| H304A | GCTAAATTCATTTCAAAAAAGAAAGCCGTGAGCCTGTGC | 130 | GCACAGGCTCACGGCTTTGTTTTTTGAAATGAATTTAGC | 131 |
| V305A | CATTTCAAAAAACAAACACGCGAGCCTGTGCATCTTC | 132 | GAAGATGCACAGGCTCGCGTTTGTTTTTTGAAATG | 133 |
| L307A | CAAAAAACAAACACGTGAGCGCGTGCATCTTCACTGCC | 134 | GGCAGTGAAGATGCACGCGCTCACGTGTTTGTTTTTG | 135 |
| C308A | CAAACACGTGAGCCTGGCCATCTTCACTGCCCG | 136 | CGGGCAGTGAAGATGGCCAGGCTCACGTGTTG | 137 |
| I309A | CGTGAGCCTGTGCGCCTTCACTGCCCGC | 138 | GCGGGCAGTGAAGGCGCACAGGCTCACG | 139 |
| F310A | GAGCCTGTGCATCGCCACTGCCCGCATC | 140 | GATGCGGGCAGTGGCGATGCACAGGCTC | 141 |
| I314A | CATCTTCACTGCCCGCGCCTATGATGATCAAGG | 142 | CCTTGATCATCATAGGCGCGGGCAGTGAAGATGC | 143 |
| Y315A | CACTGCCCGCATCGCTGATGATCAAGGAAGATGTC | 144 | GACATCTTCCTTGATCATCAGCGATGCGGGCAGTG | 145 |
| C321A | GCATCTATGATGATCAAGGAAGAGCTCAGGAGGGGCTGC | 146 | GCAGCCCCTCCTGAGCTCTTCCTTGATCATCATAGATGC | 147 |
| L325A | GATGTCAGGAGGGGCGCGCACCCTGGC | 148 | GCCAGGGTGCGCGCCCCCTCCTGACATC | 149 |
| R326A | CAGGAGGGGCTGGCCACCCTGGCCG | 150 | CGGCCAGGGTGGCCAGCCCCTCCTG | 151 |
| L328A | GGGCTGCGCACCGCGGCCGAGGCTGG | 152 | CCAGCCTCGGCCGCGGTGCGCAGCCC | 153 |
| I335A | GGCTGGGGCCAAAGCTTCAATAATGACATACAGTGAATTTAAG | 154 | CTTAAATTCACTGTATGTCATTATTGAAGCTTTGGCCCCAGCC | 155 |
| I337A | CTGGGGCCAAAATTTCAGCAATGACATACAGTG | 156 | GTGCTTAAATTCACTGTATGTCATTGCTGAAATTTTGGCCCCAGAATTTAAGCAC | 157 |

TABLE 1-continued

Oligonucleotides used to construct A3G deletion or alanine mutants.

| Mutant | Oligo 1 (5' to 3') | SEQ ID NO: | Oligo 2 (5' to 3') | SEQ ID NO: |
|---|---|---|---|---|
| M338A | CTGGGGCCAAAATTTCAATAGCGACATACAGTGAATTTAAGCAC | 158 | GTGCTTAAATTCACTGTATGTCGCTATTGAAATTTTGGCCCCAG | 159 |
| Y340A | GGGCCAAAATTTCAATAATGACAGCCAGTGAATTAAGCAGTGC | 160 | GCAGTGCTTAAATTCACTGGCTGTCATTATTGAAATTTTGGCCC | 161 |
| E342A | CAATAATGACATACAGTGCATTTAAGCACTGCTGG | 162 | CCAGCAGTGCTTAAATGCACTGTATGTCATTATTG | 163 |
| F343A | CAATAATGACATACAGTGAAGCTAAGCACTGCTGGGAC | 164 | GTCCCAGCAGTGCTTAGCTTCACTGTATGTCATTATTG | 165 |
| C346A | GACATACAGTGAATTTAAGCACGCCTGGGACACCTTTGTG | 166 | CACAAAGGTGTCCCAGGCGTGCTTAAATTCACTGTATGTC | 167 |
| W347A | CAGTGAATTTAAGCACTGCGCGGACACCTTTGTGG | 168 | CCACAAAGGTGTCCGCGCAGTGCTTAAATTCACTG | 169 |
| F350A | CTGCTGGGACACCGCTGTGGACCACCAGG | 170 | CCTGGTGGTCCACAGCGGTGTCCCAGCAG | 171 |
| V351A | CTGGGACACCTTTGCGGACCACCAGGG | 172 | CCCTGGTGGTCCGCAAAGGTGTCCCAG | 173 |
| C356A | GTGGACCACCAGGGAGCTCCCTTCCAGCCC | 174 | GGGCTGGAAGGGAGCTCCCTGGTGGTCCAC | 175 |
| F358A | CACCAGGGATGTCCCGCCCAGCCCTGGGATG | 176 | CATCCCAGGGCTGGGCGGGACATCCCTGGTG | 177 |
| W361A | CCCTTCCAGCCCGCGGATGGACTAGATGAGC | 178 | GCTCATCTAGTCCATCCGCGGGCTGGAAGGG | 179 |
| L364A | GCCCTGGGATGGAGCAGATGAGCACAGCCAAG | 180 | CTTGGCTGTGCTCATCTGCTCCATCCCAGGGC | 181 |
| L371A | GAGCACAGCCAAGACGCGAGTGGGAGGCTG | 182 | CAGCCTCCCACTCGCGTCTTGGCTGTGCTC | 183 |
| L375A | GACCTGAGTGGGAGGGCGCGGGCCATTCTCC | 184 | GGAGAATGGCCCGCGCCCTCCCACTCAGGTC | 185 |
| I378A | GGCTGCGGGCCGCTCTCCAGAATCAGGAAAAC | 186 | GTTTTCCTGATTCTGGAGAGCGGCCCGCAGCC | 187 |
| L379A | GCTGCGGGCCATTGCCCAGAATCAGGAAAACTG | 188 | CAGTTTTCCTGATTCTGGGCAATGGCCCGCAGC | 189 |

TABLE 2

Oligonucleotides used to construct A3G lysine mutants.

| Name | SEQUENCE | SEQ ID NO: |
|---|---|---|
| A3G-F204K_S | GATCCACCCACATTCACTAAAAACTTTAACAATGAACCTTGG | 190 |
| A3G-F204K_A | CCAAGGTTCATTGTTAAAGTTTTTAGTGAATGTGGGTGGATC | 191 |
| A3G-W211K_S | CAACTTTAACAATGAACCTAAAGTCAGAGGACGGC | 192 |
| A3G-W211K_A | GCCGTCCTCTGACTTTAGGTTCATTGTTAAAGTTG | 193 |
| A3G-V212K_S | CAACTTTAACAATGAACCTTGGAAAAGAGGACGGCATGAG | 194 |
| A3G-V212K_A | CTCATGCCGTCCTCTTTTCCAAGGTTCATTGTTAAAGTTG | 195 |
| A3G-Y219K_S | GGACGGCATGAGACTAAACTGTGTTATGAGGTGGAG | 196 |
| A3G-Y219K_A | CTCCACCTCATAACACAGTTTAGTCTCATGCCGTCC | 197 |
| A3G-V224K_S | GAGACTTACCTGTGTTATGAGAAAGAGCGCATGCACAATG | 198 |
| A3G-V224K_A | CATTGTGCATGCGCTCTTTCTCATAACACAGGTAAGTCTC | 199 |
| A3G-M227K_S | GAGGTGGAGCGCAAAACACAATGACACCTGG | 200 |
| A3G-M227K_A | CCAGGTGTCATTGTGTTTTGCGCTCCACCTC | 201 |

TABLE 2-continued

Oligonucleotides used to construct A3G lysine mutants.

| Name | SEQUENCE | SEQ ID NO: |
|---|---|---|
| A3G-W232K_S | GCATGCACAATGACACCAAAGTCCTGCTGAACCAG | 202 |
| A3G-W232K_A | CTGGTTCAGCAGGACTTTGGTGTCATTGTGCATGC | 203 |
| A3G-V233K_S | GCACAATGACACCTGGAAACTGCTGAACCAGCG | 204 |
| A3G-V233K_A | CGCTGGTTCAGCAGTTTCCAGGTGTCATTGTGC | 205 |
| A3G-L234K_S | CAATGACACCTGGGTCAAACTGAACCAGCGCAG | 206 |
| A3G-L234K_A | CTGCGCTGGTTCAGTTTGACCCAGGTGTCATTG | 207 |
| A3G-L235K_S | GACACCTGGGTCCTGAAAAACCAGCGCAGGG | 208 |
| A3G-L235K_A | CCCTGCGCTGGTTTTTCAGGACCCAGGTGTC | 209 |
| A3G-F241K_S | CAGCGCAGGGGCAAACTATGCAACCAGGCTC | 210 |
| A3G-F241K_A | GAGCCTGGTTGCATAGTTTGCCCCTGCGCTG | 211 |
| A3G-L242K_S | GCGCAGGGGCTTTAAATGCAACCAGGCTC | 212 |
| A3G-L242K_A | GAGCCTGGTTGCATTTAAAGCCCCTGCGC | 213 |
| A3G-F252K_S | TCCACATAAACACGGTAAACTTGAAGGCCGCC | 214 |
| A3G-F252K_A | GGCGGCCTTCAAGTTTACCGTGTTTATGTGGA | 215 |
| A3G-L253K_S | CCACATAAACACGGTTTCAAAGAAGGCCGCCATGC | 216 |
| A3G-L253K_A | GCATGGCGGCCTTCTTTGAAACCGTGTTTATGTGG | 217 |
| A3G-L260K_S | CCGCCATGCAGAGAAATGCTTCCTGGACGTG | 218 |
| A3G-L260K_A | CACGTCCAGGAAGCATTTCTCTGCATGGCGG | 219 |
| A3G-F262K_S | CATGCAGAGCTGTGCAAACTGGACGTGATTCCC | 220 |
| A3G-F262K_A | GGGAATCACGTCCAGTTTGCACAGCTCTGCATG | 221 |
| A3G-V265K_S | GCTGTGCTTCCTGGACAAAATTCCCTTTTGGAAGC | 222 |
| A3G-V265K_A | GCTTCCAAAAGGGAATTTTGTCCAGGAAGCACAGC | 223 |
| A3G-I266K_S | GCTTCCTGGACGTGAAACCCTTTTGGAAGCTGG | 224 |
| A3G-I266K_A | CCAGCTTCCAAAAGGGTTTCACGTCCAGGAAGC | 225 |
| A3G-F268K_S | TCCTGGACGTGATTCCCAAATGGAAGCTGGACCTGG | 226 |
| A3G-F268K_A | CCAGGTCCAGCTTCCATTTGGGAATCACGTCCAGGA | 227 |
| A3G-W269K_S | GACGTGATTCCCTTTAAAAAGCTGGACCTGG | 228 |
| A3G-W269K_A | CCAGGTCCAGCTTTTTAAAGGGAATCACGTC | 229 |
| A3G-L273K_S | CCTTTTGGAAGCTGGACAAAGACCAGGACTACAGG | 230 |
| A3G-L273K_A | CCTGTAGTCCTGGTCTTTGTCCAGCTTCCAAAAGG | 231 |
| A3G-Y277K_S | CCTGGACCAGGACAAAAGGGTTACCTGCTTC | 232 |
| A3G-Y277K_A | GAAGCAGGTAACCCTTTTGTCCTGGTCCAGG | 233 |
| A3G-V279K_S | CCAGGACTACAGGAAAACCTGCTTCACCTC | 234 |
| A3G-V279K_A | GAGGTGAAGCAGGTTTTCCTGTAGTCCTGG | 235 |
| A3G-F289K_S | CTGGAGCCCCTGCAAAAGCTGTGCCCAGG | 236 |
| A3G-F289K_A | CCTGGGCACAGCTTTTGCAGGGGCTCCAG | 237 |
| A3G-I299K_S | CCAGGAAATGGCTAAATTCAAATCAAAAACAAACACGTGAGC | 238 |

TABLE 2-continued

Oligonucleotides used to construct A3G lysine mutants.

| Name | SEQUENCE | SEQ ID NO: |
|---|---|---|
| A3G-I299K_A | GCTCACGTGTTTGTTTTTTGATTTGAATTTAGCCATTTCCTGG | 239 |
| A3G-F310K_S | CGTGAGCCTGTGCATCAAAACTGCCCGCATCTATGATG | 240 |
| A3G-F310K_A | CATCATAGATGCGGGCAGTTTTGATGCACAGGCTCACG | 241 |
| A3G-I337K_S | CTGGGGCCAAAATTTCAAAAATGACATACAGTGAATTTAAGC | 242 |
| A3G-I337K_A | GCTTAAATTCACTGTATGTCATTTTTGAAATTTTGGCCCCAG | 243 |
| A3G-Y340K_S | GGGCCAAAATTTCAATAATGACAAAAAGTGAATTTAAGCACTGCTG | 244 |
| A3G-Y340K_A | CAGCAGTGCTTAAATTCACTTTTTGTCATTATTGAAATTTTGGCCC | 245 |
| A3G-V351K_S | CTGCTGGGACACCTTTAAAGACCACCAGGGATG | 246 |
| A3G-V351K_A | CATCCCTGGTGGTCTTTAAAGGTGTCCCAGCAG | 247 |
| A3G-L371K_S | GAGCACAGCCAAGACAAAAGTGGGAGGCTGC | 248 |
| A3G-L371K_A | GCAGCCTCCCACTTTTGTCTTGGCTGTGCTC | 249 |
| A3G-I378K_S | GGCTGCGGGCCAAACTCCAGAATCAGGAAAACTG | 250 |
| A3G-I378K_A | CAGTTTTCCTGATTCTGGAGTTTGGCCCGCAGCC | 251 |

All oligonucleotides are presented 5' to 3'

*Escherichia coli* mutation assays: The *E. coli*-based, rifampicin-resistance (Rif$^R$) mutation assay has been used to monitor the intrinsic DNA cytosine deaminase activity of several A3 proteins including A3G (e.g. Harris et al., *Mol. Cell* 10, 1247-1253 (2002)). *E. coli* strain BW310 (uracil excision defective) was used. Aliquots of saturated overnight cultures (LB plus 200 µg/mL ampicillin) were spread onto LB plates containing 100 µg/mL rifampicin to select for Rif$^R$ mutants and diluted aliquots were spread onto LB plates containing 200 µg/mL ampicillin to determine the number of viable cells. Mutation frequencies were calculated by dividing the number of Rif$^R$ mutants by the number of viable cells in each culture. For the deletion experiments, the mutation frequencies of eight individual cultures were plotted and the median indicated. For the alanine or lysine mutant experiments, the Rif$^R$ mutation frequency for each construct was determined by assaying the median Rif$^R$ mutation frequency for 8-12 independent cultures, calculating the fold-difference relative to the median value of the vector control cultures and averaging at least two (and up to 12) independent experiments.

GST-A3G expression, purification and size exclusion procedures: GST-A3G protein levels were monitored by expressing them in *E. coli* BL21 DE3 RIL (Stratagene), sonicating the cells in lysis buffer (100 mM NaCl, 50 mM Na$_2$HPO$_4$/NaH$_2$PO$_4$ [pH7.0], protease inhibitor [Roche]), separating the soluble (supernatant) and insoluble (pellet) fractions by centrifugation (12110 x g, 20 min, 4° C.) and fractionating aliquots of the resulting proteins by SDS-PAGE. Proteins were detected by coomassie blue and quantified by Image J software (http at rsb.info.nih.gov/ij/). Immunoblots were done with antibodies from GE Healthcare (anti-GST) and from J. Lingappa (anti-A3G; [Newman et al., *Curr. Biol.* 15, 166-170 (2005)]).

GST-based constructs were expressed in *E. coli* strain BL21 DE3 RIL (Stratagene). Unlabeled proteins were produced by overnight expression at 17° C. in LB medium containing 1 mM IPTG and 200 µg/mL ampicillin. Isotope-labeled proteins were produced by overnight expression at 17° C. in M9 supplemented with $^{15}$NH$_4$Cl, $^{13}$C-labeled D-glucose and $^2$H water as previously described by Devany et al., *Protein Sci.* 13, 2252-259 (2004). Proteins were purified by sonicating cell pellets in lysis buffer [100 mM NaCl, 50 mM Na$_2$HPO$_4$/NaH$_2$PO$_4$ (pH7.0), protease inhibitor (Roche)], separating the soluble (supernatant) and insoluble (pellet) fractions by centrifugation (12,110 g, 20 min, 4° C.), binding to glutathione sepharose (GE healthcare), washing with lysis buffer and eluting with PreScission protease (GE Healthcare) in 1 mM DTT, 50 mM Na$_2$HPO$_4$/NaH$_2$PO$_4$ [pH7.4] and, finally, concentrating with Centricon filters (Millipore). Solubility was monitored by SDS PAGE, coomassie blue staining and/or immunoblotting as discussed above. For size exclusion experiments, GST-A3G198-384 was bound to glutathione sepharose, washed several times with lysis buffer, eluted with PreScission protease (GE Healthcare) in 1 mM DTT, 50 mM Na$_2$HPO$_4$/NaH$_2$PO$_4$ [pH 7.0] buffer, quantified and immediately 1 mg (approx. 1 mL) was passed through a Superdex 75 size exclusion column (GE Healthcare) and detected in fractions by UV (absorbance 280). GST and lysozyme were purchased from Sigma.

Structural modeling: A3G198-384 and APOBEC2 primary amino acid sequences were aligned with the homology modeling module of the InsightII program (Accelrys) (FIG. 1). Secondary structural elements of A3G 198-384 were predicted using the HNN program. Combet et al. *Trends Biochem Sci.* 25, 147-150 (2000); Guermeur et al. *Bioinformatics* 15, 413-421 (1999). A model was generated by fitting these elements (allowing for gaps) to those in the actual structure of APOBEC2 (PDB 2YNT; Prochnow et al. *Nature* 445, 447-451 (2004)). No gross differences in secondary structure were observed. The homology modeling module of the InsightII program (Accelrys) was used to construct and refine the model by minimizing energetically unfavorable amino acid side chain interactions.

Circular Dichroism (CD) Spectroscopy: Proteins were purified as described above and diluted to 6 μM in 50 mM $Na_2HPO_4/NaH_2PO_4$ [pH7.4], 50 μM $ZnCl_2$. CD spectra were collected on a Jasco 710 dichrograph using 10 mm thick quartz cells at 10° C. Data were acquired between 190 and 250 nm at 50 nm/min with a bandwidth of 1 nm.

Sedimentation Velocity Analytical Ultracentrifugation Experiments. A3G-2K3A was diluted to 0.15, 0.4, 0.8 or 1.2 mg/ml in a buffer containing 50 mM $Na_2HPO_4/NaH_2PO_4$ [pH7.4], 0.005% tween 20, 5 mM dithiothreitol and 50 μM $ZnCl_2$. Samples were then sedimented using a 4-hole rotor at 20° C. and 55,000 rpm. The rotor and cells were preequilibrated at 20° C. and the samples were kept on ice during protein preparation and dilution. Synthetic boundary cells were loaded with 430 μL of buffer and 420 μL of the appropriate sample solution. The cells were placed in the rotor and accelerated to 24,000 rpm while monitoring the transfer of the excess buffer in each cell. Subsequently, the rotor was stopped and then gently inverted to thoroughly mix the contents of the cells. The rotor was then equilibrated under vacuum at 20° C. and after a period of ~1 hour at 20° C. the rotor was accelerated to 55,000 rpm. Interference scans were acquired at 1 minute intervals for 6 hours. The data for each loading concentration was analyzed using the program DcDt+ (version 2.0.7). See Philo, *Anal. Biochem.* 354, 238-246 (2006); and Philo, *Anal. Biochem.* 279, 151-163 (2000). The normalized g(s*) plots of all four concentrations of A3G-2K3A are shown in FIG. 1d. The complete data set for A3G-2K3A was analyzed using Sedphat v4.4b using the model of a hybrid local continuous distribution and global discrete species. Schuck, *Anal. Biochem.* 320, 104-124 (2003). The fit yielded a value of 22.15 kDa [21.85, 22.45; 95% confidence limits] for the molecular weight, and a corrected sedimentation coefficient, s20,w of 2.42S, with an r.m.s. error of 0.0034 mg/ml. A similar analysis using Sedanal v4.37 gave a value of 22.3 kDa [21.9, 22.8; 95% confidence limits] for the molecular weight, and a corrected sedimentation coefficient, s20,w of 2.39S, with an r.m.s. error of 0.0025 mg/mL. Stafford and Sherwood, *Biophys. Chem.,* 108, 231-243 (2004).

NMR spectroscopy and structure determination: Five amino acid substitutions, L234K, C243A, F310K, C321A and C356A, were required to increase the solubility and stability of A3G-198-384 for NMR experiments. The backbone $^1H$, $^{13}C$ and $^{15}N$ resonances of the uniformly $^{13}C$ and $^{15}N$ labeled and 90% perdeuterated protein were assigned using triple resonance HNCA, HNCO, HNCACB, HNCOCACB, HNCOCA and HNCACO experiments. See, Matsuo et al., *J Magn Reson B* 113, 91-96 (1996); Ikura et al. *Biochemistry* 29, 4659-4667 (1990); Kay et al. *J. Magn. Reson.* 89, 496-514 (1990); Wittekind and Mueller, *J. Magn. Reson. B* 101, 201-205 (1993); Matsuo et al. *J Magn Reson B* 111, 194-198 (1996); Matsuo et al., *J Magn Reson B* 110, 112-115 (1996); and Clubb et al., *J. Magn. Reson.* 97, 213-217 (1992).

The side chain assignments were completed using 3D CCONH, HCCH-TOCSY and $^{15}N$-, $^{13}C$edited NOESY-HSQC with 80 ms mixing time. Grzesiek, et al. *J. Magn. Reson. B* 101, 114-119 (1993); Clore, et al. *Biochemistry* 29, 8172-8184 (1990); Zhang, et al. *J. Biomol. NMR* 4 (1994). NOE-derived distance restraints were obtained from $^{15}N$- or $^{13}C$-edited NOESY-HSQC and 2D NOESY spectra acquired with the 200 ms (for $^{15}N$-edited NOESY of perdeuterated protein), 150 ms (for $^{15}N$-edited NOESY of non-deuterated protein) or 100 ms mixing time (for $^{13}C$-edited NOESY and 2D NOESY). To collect NOEs between amide proton and methyl proton, aromatic proton and methyl proton, or aromatic proton and aromatic proton, these protons were selectively protonated in an otherwise fully deuterated protein.

NMR spectra were processed with NMRPipe (Delaglio et al. *J Biomol NMR* 6, 277-293 (1995)) and analyzed with CARA [Keller. R. (2004). The computer aided resonance assignment tutorial. Cantina Verlag, Goldau]. Two hundred (200) torsion angles restraints were taken from TALOS prediction. Cornilescu, et al. *J Biomol NMR* 13, 289-302 (1999). One hundred forty two (142) hydrogen bonds were set for residues consistent with the chemical shifts deviations and NOE pattern defined secondary structure. One thousand (1000) NOE distance restraints were picked manually from NOESY data, and 1004 additional NOEs were assigned using Atnos/Candid structure dependent cycles. Herrmann, et al. *J Biomol NMR* 24, 171-189 (2002); Herrmann, et al., *J Mol Biol* 319, 209-227 (2002).

The final calculation employed 242 intra-residue, 604 sequential, 506 medium-range and 652 long-range NOEs. 100 structures were calculated with CNS30 torsion angle molecular dynamics. Ten of the calculated structures were chosen based on energy and Ramachandran plot to represent in the FIG. 2 ensemble. NMR calculation statistics are summarized in Tables 3 and 4.

TABLE 3

NMR statistics for A3G-2K3A (2jyw)

| Violations (mean and s.d.) | |
|---|---|
| Distance constraints (Å) | 0.00 ± 0.00 |
| Dihedral angle constraints (°) | 0.00 ± 0.00 |
| Max. dihedral angle violation (°) | 4.03 |
| Max. distance constraint violation (Å) | 0.21 |
| Deviations from idealized geometry | |
| Bond lengths (Å) | 0.0026 ± 0.0000 |
| Bond angles (°) | 0.4622 ± 0.0124 |
| Impropers (°) | 0.3531 ± 0.0217 |
| Average pairwise r.m.s.d. (Å) | |
| Heavy (residues 206-234, 240-242, 254-381) | 1.6 |
| Backbone (residues 206-234, 240-242, 254-381) | 0.81 |

TABLE 4

Detailed NMR statistics for A3G-2K3A (2jyw)

| Distance Restraints NOEs | |
|---|---|
| All | 2008 |
| Intra-residue | 242 |
| Inter-residue | 1772 |
| Sequential (|i − j| = 1) | 604 |
| Medium | 506 |
| Long | 656 |
| Hydrogen bonds | 142 |
| Dihedral angel restraints: | |
| Φ | 115 |
| Ψ | 115 |
| Average RMSD | |
| from distance restraints | 0.019 ± 0.0005 |
| from distance restraints | 0.3626 ± 0.0335 |
| from idealized geometry: | |
| bonds (Å) | 0.0026 ± 0.00004 |
| angels (°) | 0.4622 ± 0.0124 |
| impropers (°) | 0.3531 ± 0.0217 |
| average pairwise between 10 structures: | |
| backbone (Å) * | 0.81 ± 0.15 |
| all heavy atoms (Å) * | 1.6 ± 0.17 |
| backbone (Å) ** | 0.55 ± 0.14 |

TABLE 4-continued

Detailed NMR statistics for A3G-2K3A (2jyw)

| all heavy atoms (Å) ** | 1.26 ± 0.21 |
|---|---|
| Ramachandran plot appearance: | |
| Most favored regions (%) | 66 |
| Additional allowed (%) | 29 |
| Generously allowed (%) | 3.4 |
| Disallowed regions (%) | 1.6 |

* these calculation included residues 206-234, 240-242 and 254-381 (the bulge between β2 and β2' and the loop between β2' and α1 were excluded)
** these calculations included all secondary structure elements (residues 219-228, 231-233, 240-242, 258-269, 276-282, 288-301, 306-311, 321-336, 339-351 and 363-379)

The position of $Zn^{2+}$ in the A3G-2K3A structure was estimated based on how it is coordinated in existing deaminase superfamily member crystal structures. Betts, et al., *J Mol Biol* 235, 635-656 (1994); Johansson, et al. *Biochemistry* 41, 2563-2570 (2002); Ko, et al., *J Biol Chem* 278, 19111-19117 (2003); Losey, et al. *Nat Struct Mol Biol* 13, 153-159 (2006); and Xie, et al. *Proc Natl Acad Sci USA* 101, 8114-8119 (2004). Table 5 lists the covalent bond lengths and angles that were used to link $Zn^{2+}$ to H257, C288 and C291 in the A3G-2K3A structure.

TABLE 5

Constraints for $Zn^{2+}$ positioning*

Covalent bonds

| Atom 1 | Atom 2 | Length (Å) |
|---|---|---|
| H257 Nδ1 | $Zn^{2+}$ | 2.0 |
| C288 Sγ | $Zn^{2+}$ | 2.3 |
| C291 Sγ | $Zn^{2+}$ | 2.3 |

Bond angles

| Atom 1 | Atom 2 | Atom 3 | Angle (degrees) |
|---|---|---|---|
| H257 Cγ | H257 Nδ | $Zn^{2+}$ | 126 |
| C288 Cβ | C288 S | $Zn^{2+}$ | 108 |
| C291 Cβ | C291 S | $Zn^{2+}$ | 108 |

*$Zn^{2+}$ molecule was constrained in the structure of A3G-2K3A. Covalent bonds were created between $Zn^{2+}$ and His 257, Cys288 or Cys291. The bond lengths and angles used for the calculation are listed.

NMR titration experiments: Non-labeled ssDNA was titrated into 15N-labeled A3G-2K3A at protein:DNA molar ratios of 1:0, 1:1, 1:2, 1:4, 1:8 and 1:16. A heteronuclear single quantum coherence (HSQC) spectrum was recorded at each molar ratio, which enabled specific amino acid chemical shift perturbations to be detected. Chemical shift perturbation was calculated using following equation $\Delta\delta=[(\Delta^1H)^2+(\Delta^{15}N/5)^2]^{1/2}$ where $\Delta^1H$ and $\Delta^{15}N$ are differences in $^1H$ chemical shifts and $^{15}N$ chemical shifts, respectively.

Single-strand DNA binding model: The target cytosine was positioned in the catalytic active site (under H257 and adjacent to E259) based on existing crystal structures of active cytidine deaminases. Teh, et al. *Biochemistry* 45, 7825-7833 (2006); and Xiang, et al. *Biochemistry* 36, 4768-4774 (1997). This positioning fixed the target cytosine base and enabled calculations of all possible rotamer configurations of the 5'-C (C1), the 3'-T (T3) and all 25 of the amino acid side chains that showed significant NMR chemical shift perturbations (R215, T218, Y219, C221, H228, L242, A246, E254, R256, A258, E259, V265, C281, N302, C308, R313, I314, Y315, D316, G332, I337, H345, W347, G355, and H367; i.e., signals that were 1 SD above mean in FIG. 15). All rotable bonds were varied (6 bonds per nucleotide) to obtain lowest energy configurations for both the DNA and the affected A3G-2K3A residues. Although these calculations resulted in a very large number of possible configurations, the number was efficiently reduced using the dead-end elimination method, which eliminates configurations of side-chains or nucleotides that are unlikely be part of the global minimum structure. Desmet, et al. *Nature* 356, 539-542 (1992); and Goldstein, *Biophys J* 66, 1335-1340 (1994). The reduced number of configurations was enumerated systematically to arrive at a minimum energy model.

Example 2

Residues 198-384 of APOBEC3G are Sufficient for DNA Deamination

Figure 2:
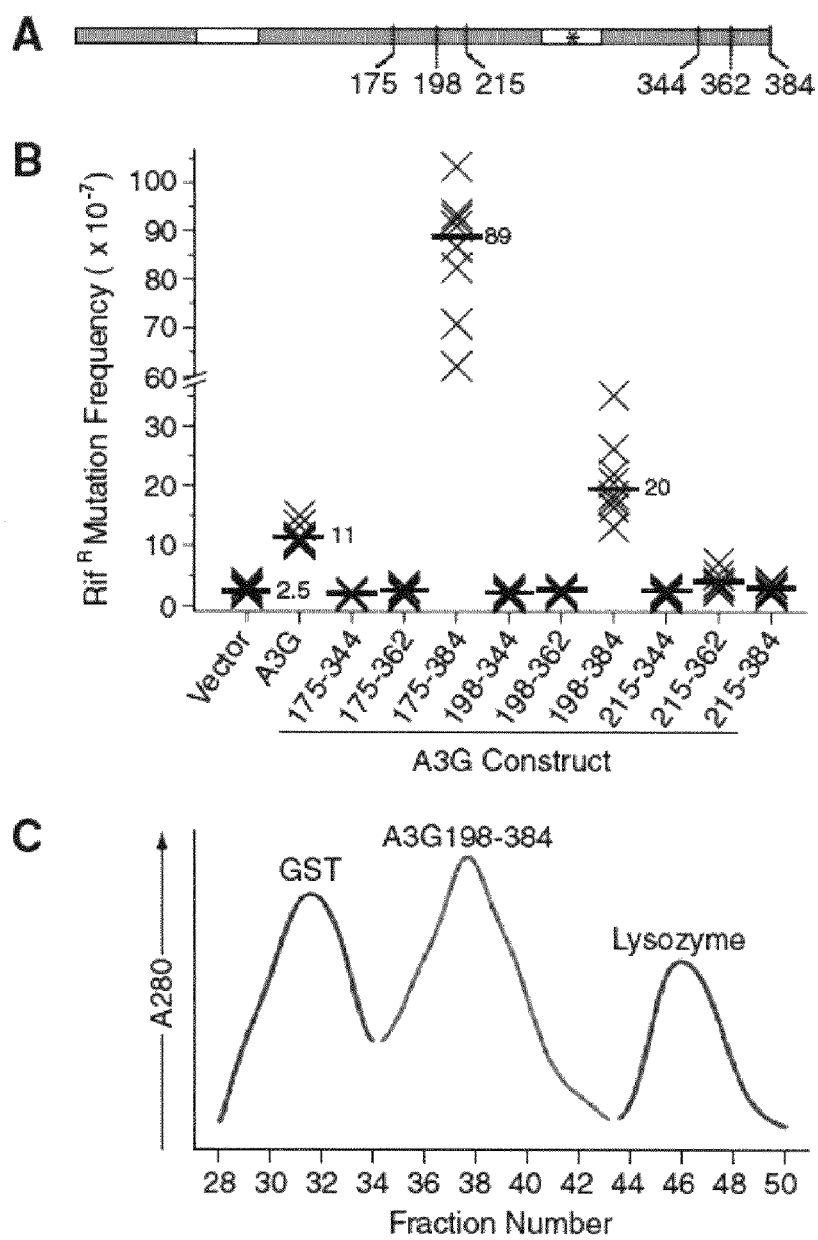
FIG. 2A-2B show that APOBEC3G deletion mutants delineate a minimal active domain. (A) An illustration showing the amino acid boundaries used for deletion constructs. The $HXE-X_{23-28}-CX_{2-4}C$ motifs are depicted by open boxes, and the asterisk designates the catalytic domain. (B) $Rif^R$ mutation frequencies of the indicated GST-A3G constructs. Each X represents the mutation frequency of an individual culture (n=8 per construct). The median mutation frequency for cells expressing the vector control, A3G, A3G175-384 and A3G198-384 is indicated. (C) Size exclusion profiles of GST (25 kDa), A3G198-384 (22 kDa) and lysozyme (14 kDa) indicate that A3G198-384 is monomeric.

Chimeric APOBEC3 proteins and site-directed mutants have been used to demonstrate that the intrinsic DNA cytosine deaminase activity of human APOBEC3G resides in the conserved C-terminal zinc-coordinating domain. Hache et al., *J. Biol. Chem.* 280, 10920-10924 (2005); Iwatani, et al. *J. Virol.* 80, 5992-6002 (2006); Newman, et al. *Curr. Biol.* 15, 166-170 (2005); Navarro et al. *Virology* 333, 374-386 (2005). To further delineate the minimal domain required for catalysis, nine A3G deletion constructs were tested for mutability in the *E. coli*-based RifR mutation assay (FIG. 2). Bacteria expressing GST showed a median of 2.5 RifR mutants per $10^7$ viable cells.

Expression of full-length A3G fused to GST caused a 4.4-fold increase in mutation frequency. Apart from two notable exceptions, all of the A3G deletion constructs were inactive. The inactivity of constructs lacking 22 or 40 C-terminal residues was consistent with prior work showing that A3G lacking 38 or 89 C-terminal amino acids was unable to inhibit HIVΔvif. Li, et al. *J. Cell Biochem.* 92, 560-572 (2004); Shindo et al. *J. Biol. Chem.* 278, 44412-44416 (2003).

A more interesting result emerged from analyses of N-terminal deletion set. A3G variants encoding residues 175-384 or 198-384, but not 215-384, were considerably more mutable than full-length A3G. These data demonstrated that the entire N-terminal, zinc-binding domain is dispensable for activity, and only A3G residues 198-384 are required.

Example 3

Size Exclusion Experiments Indicate that A3G198-384 is Monomeric

Previous studies indicated that an A3G C97A mutant was incapable of co-immunoprecipitating wildtype A3G, but was still capable of DNA deamination. Navarro et al. *Virology* 333, 374-386 (2005); and Opi, et al. *J. Virol.* 80, 4673-4682 (2006). Consistent with these studies, A3G198-384 profiled as a 22 kDa monomer in size exclusion experiments, migrating clearly between the elution positions of lysozyme (14 kDa) and GST (25 kDa) (FIG. 2C). It is not likely that stable oligomeric forms of A3G198-384 exist, because fractions 1-27 did not contain protein peaks.

Example 4

Alanine Mutations Define Essential and Non-Essential Residues of A3 G198-384

Figure 3:
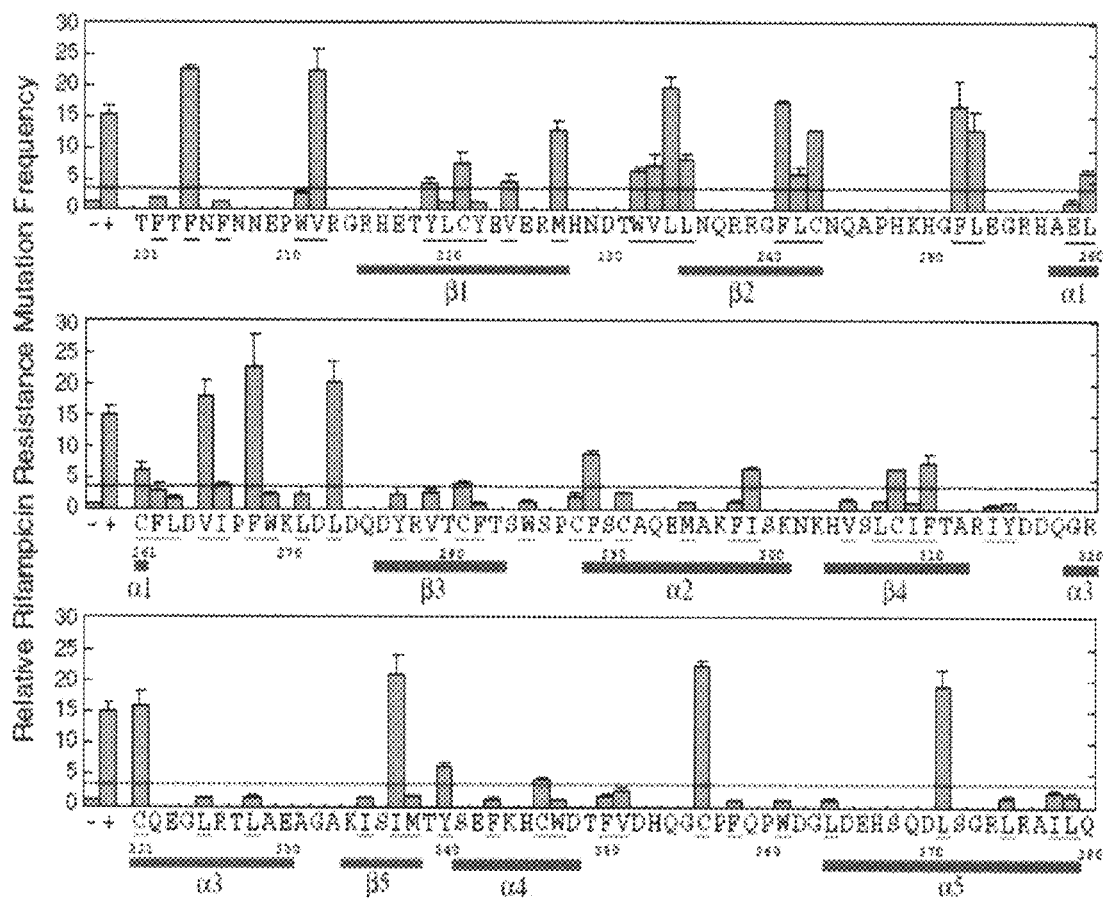
FIG. 3 contains histograms depicting the mutator phenotype of 69 APOBEC3G alanine substitution mutants. The histograms show the relative $Rif^R$ mutation frequencies of cells expressing the vector control (−), A3G198-384 (+) or derivatives with alanine substitutions at the underlined amino acid positions. Each histogram bar reports data from two to five independent experiments, except the bars for vector and A3G198-384, which reflect data from 12 (±S.E.M.). The dotted line represents the 3-fold significance threshold that was used to distinguish active and inactive mutant constructs. A3G amino acids 198-200 and 381-384 were not shown. A predicted secondary structure of A3G198-384, based on a pair wise alignment with APOBEC2, is included to facilitate comparisons with FIG. 5.

To more precisely delineate the residues and domains required for DNA deamination, the A3G198-384 variant was used to construct a series of 69 alanine mutants (FIG. 3). Mutagenesis was concentrated to hydrophobic residues and cysteines. This strategy was motivated partly by the likelihood that some of the hydrophobic amino acids would likely be important structurally (perhaps forming part of the enzyme core) whereas, more intriguingly, others would be positioned on the surface of the protein (perhaps defining interaction sites). It also was envisaged that mutating select hydrophobic residues might help overcome the solubility issues of A3G and other family members. Chelico, et. al. *Nat. Struct. Mol. Biol.* 13, 392-399 (2006); Iwatani, et al. supra; and Opi et al., supra. All 69 mutants were analyzed using the *E. coli*-based $Rif^R$ mutation assay, because in vitro experiments were hindered by the fact that A3G198-384 frequently precipitated during biochemical purification and invariably during long-term storage.

Twelve independent $Rif^R$ experiments, each with at least 10 constructs (and 8-12 independent cultures per mutant), were required to analyze 69 alanine mutant derivatives of A3G198-384 (FIG. 3). It was not feasible to simultaneously examine all 69 mutants, and minimizing inter-experiment variability was therefore important. This was done by normalizing the median $Rif^R$ mutation frequencies of cells expressing the control vector (i.e., the spontaneous mutation frequency was set to 1 and used as a baseline). The actual vector control values ranged from 0.8 to 3.9 RifR mutants per 10$^7$ viable cells (n=12 experiments). This approach readily enabled the mutagenic effects of A3G198-384 and derivatives to be compared between multiple experiments. For instance, the first two columns of each row of FIG. 3 report the relative mutation frequency of the vector control and A3G198-384, which increased the $Rif^R$ mutation frequency 14.9-fold (S.E.M.: 1.5-fold; n=12 experiments; the actual values ranged from 15.1 to 54.5 $Rif^R$ mutants per 10$^7$ viable cells). Although the raw experimental values fluctuated modestly between experiments (attributable to factors such as incubation temperatures, freshness of the rifampicin-containing plates, colony sizes upon counting, time in stationary phase, etc.), the small S.E.M.s indicated that the relative inter-experiment values were remarkably constant and therefore readily comparable.

A surprising number of alanine mutants elicited levels of DNA deaminase activity that were at least 3-fold greater than those of the vector control (FIG. 3). In total, 31/69 mutants met this threshold. Several of the other mutants also triggered mutation frequencies significantly above those of the vector control cells and above those of cells expressing a catalytically dead A3G variant, E259A. Newman et al., supra; Jonsson, et al. *Nucleic Acids Res.* 34, 5683-5694 (2006).

The second notable feature of this dataset was a clustering of non-essential and essential residues, defined by alanine substitution mutants that retained or lost significant activity, respectively. Approximately two-thirds of the nonessential amino acids were found in the A3G region spanning 198-275, with 224-253 particularly striking. Conversely, the majority of the essential residues were found in the C-terminal interval, 276-384, suggesting that the C-terminal end of A3G is required for the integrity of the enzyme. Third, the alanine mutant data agreed with those from the deletion studies. Toward the N-terminal end, F202, F206 and W211 were required for $Rif^R$ mutagenesis, explaining why all of the A3G variants starting at position 215 were inactive. Similarly, L364, L375, I378 and L379 were clearly required, offering a reasonable explanation for why all three C-terminal deletion constructs were inactive.

Example 5

A3G198-384 and Derivative Mutator Activities are not Simply Explained by Expression Levels To help exclude the possibility that a lack of deaminase activity might simply be due to reduced solubility or expression, the relative abundance of each protein was analyzed by SDS-PAGE. Rather than examine whole cell extracts, the soluble (supernatant) and insoluble (pellet) fractions were considered separately (the sum of course reflecting whole cell levels). A representative coomassie-stained gel is shown for the first five GST-A3G198-384 derivatives, F202A, F204A, F206A, W211A and V212A (FIG. 4A). The supernatant/pellet ratio of all five mutants was similar to that of the parent construct, indicating that the low activity levels for F202A, F206A and V212A were not simply due to solubility or expression deficiencies. Anti-GST and anti-A3G immunoblots confirmed the identity of the coomassie-stained bands (FIG. 4B). The overwhelming majority of the remaining mutants were as soluble and some were even more soluble than GST-A3G198-348 (FIG. 4C). However, six mutants were less soluble. Four of these mutants, L260A, C261A, C281A and C308A, caused significant mutation frequency increases indicating that these mutants are catalytically active and that the corresponding mutation frequencies may be underestimates. Correction factors were not calculated because these mutants did not impact major conclusions. However, two of the six less soluble mutants, W269A and C288A (one of the conserved zinc-coordinating positions), showed no activity. It was not determined whether this was due to gross insolubility, to a loss of enzyme activity or to both of these reasons. Nevertheless, the expression data indicated that vast majority of mutants are well expressed and modestly soluble and, therefore, that the corresponding *E. coli*-based activity data are informative.

Example 6

The DNA Deaminase Results Corroborate a Predicted 3D Structure for A3G198-384

Figure 5:
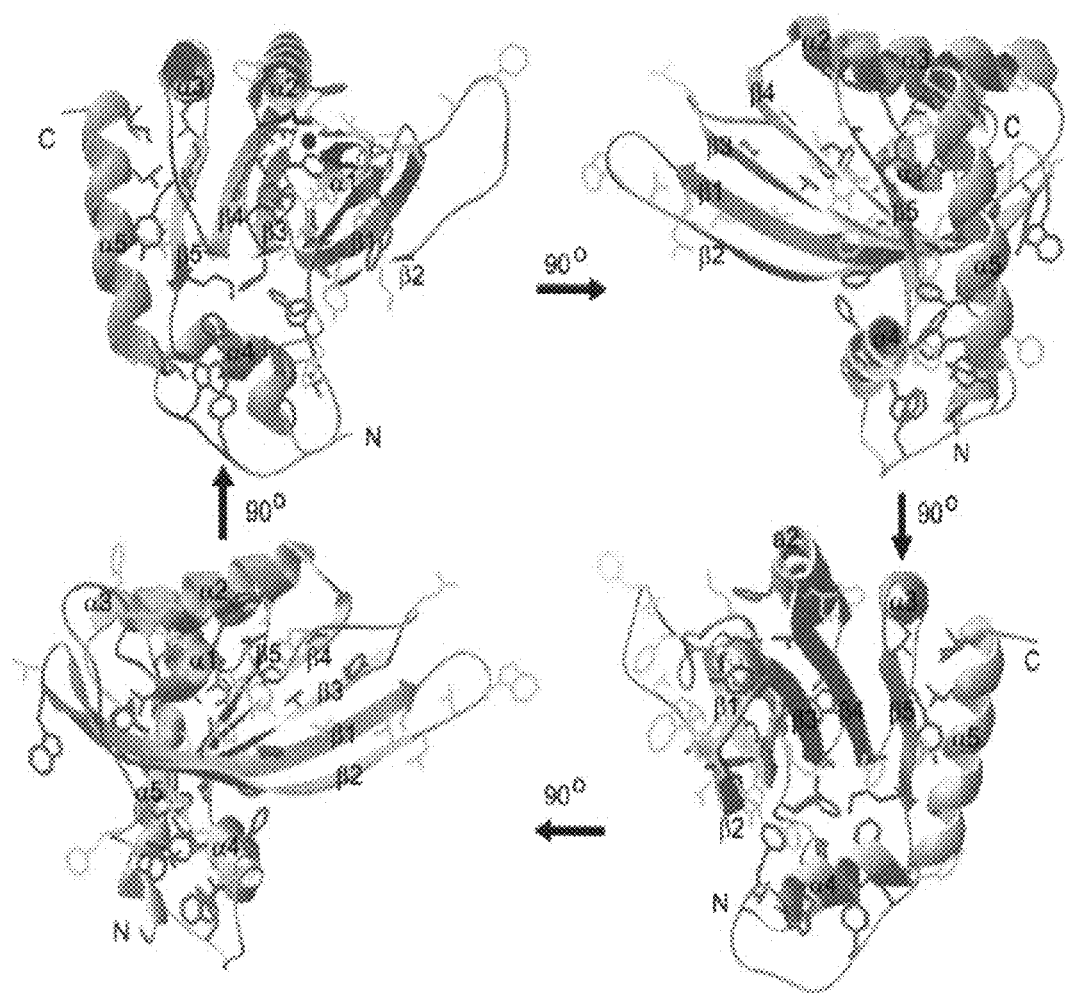
FIG. 5 contains four views of a model A3G198-384 structure based on human APOBEC2. The predicted α helices and β sheets correspond with those shown in FIG. 3. Relevant amino acid side chains are depicted in green or red to reflect the activity or inactivity, respectively, of an alanine substitution at that position. The purple amino acid side chains in the top left panel represent the zinc (purple ball)-coordinating histidine (H257 in α1) and cysteine residues (C288 and C291 in α2).

To begin to address whether there was a correlation between activity level and structural position, the APOBEC2 crystal structure was used to model A3G198-384 (FIG. 5). Side-chains of all of the mutated residues were added to the model and colored green or red, representing non-essential or essential residues, respectively. This scheme revealed two striking correlations. First, the amino acid side chains of most of the essential residues positioned toward the core of the protein, facing inward and away from solvent-accessible areas. Second, most of the amino acid side chains of the residues that were not required for DNA deamination appeared in external, solvent accessible spaces. A particularly interesting (and apparently dispensable) cluster was located within the predicted β1-loop-β2-loop region (M227, W232, V233, L234, L235, F241, L242, C243, F252 and L253). It is tempting to speculate that this region constitutes a protein interaction surface, possibly involved in an association with the N-terminal half of A3G. Such a possibility is supported by the APOBEC2 crystal structure, which shows that the analogous β2 strand forms extensive anti-parallel contacts with the β2 strand of another APOBEC2 molecule resulting in a dimer. Analogous contacts may zip-together the N- and the C-terminal halves of A3G.

The structural model also afforded reasonable explanations for the essential nature of the N- and C-terminal ends of A3G198-384 (FIG. 5). N-terminal residues preceding the β1 strand may help stabilize the β-sheet core of A3G198-384 such that removing (or mutating) these N-terminal residues would likely cause α5 to dissociate from the core and thereby render the resulting protein non-functional. Similarly, the C-terminal domain α5 helix appears positioned to help stabilize the zinc-coordinating active site, which consists of β1, β3, β4, α1 and α2.

The structural model for A3G198-384 is likely to be reasonably accurate because 31/35 of the hydrophobic residues required for DNA deaminase activity are similar (11/31) or identical (20/31) to homologous amino acids in APOBEC2. Many of the 31 residues are located within or near predicted secondary structural elements, which are probably required for hydrophobic interactions that maintain the overall structural integrity of the enzyme. These residues include L220 and Y222 in β1, F262, I266 and W269 in α1, Y277, V279 and F282 in β3, M295 in α2, V305, L307, I309, I314 and Y315 in β4, L325 and L328 in α3, I335 and M338 in β5, F343, W347, F350 and V351 in α4 and L364, L375, I378 and L379 in α5. The strong correlation between conservation and activity is further bolstered by the periodicity of the correlation—apparent at every other residue in β-strands and every three or four residues in α-helices. The amino acid side chains of these important residues are facing toward the inside of the protein structure (FIG. 5). Moreover, these correlations are even more striking when one considers that fact that these two proteins have less than 40% identity overall. Therefore, the *E. coli*-based mutation data strongly indicate that both the secondary structural elements and the overall three-dimensional folds of A3G198-384 are similar to those of APOBEC2.

A major unanswered question is how does A3G bind DNA? One clue may be provided by the location of the conserved HXE-X$_{23-28}$—CX$_{2-4}$ active site, which appeared uniquely positioned on the outside of the predicted structure, with the zinc-coordinating histidine and the two cysteines appearing toward the ends of a1 and a2 helices, respectively (FIG. 5). This positioning together with the monomeric nature of A3G198-384 suggested that single-strand DNA may be contacted by these two helices.

Example 7

Figure 6:
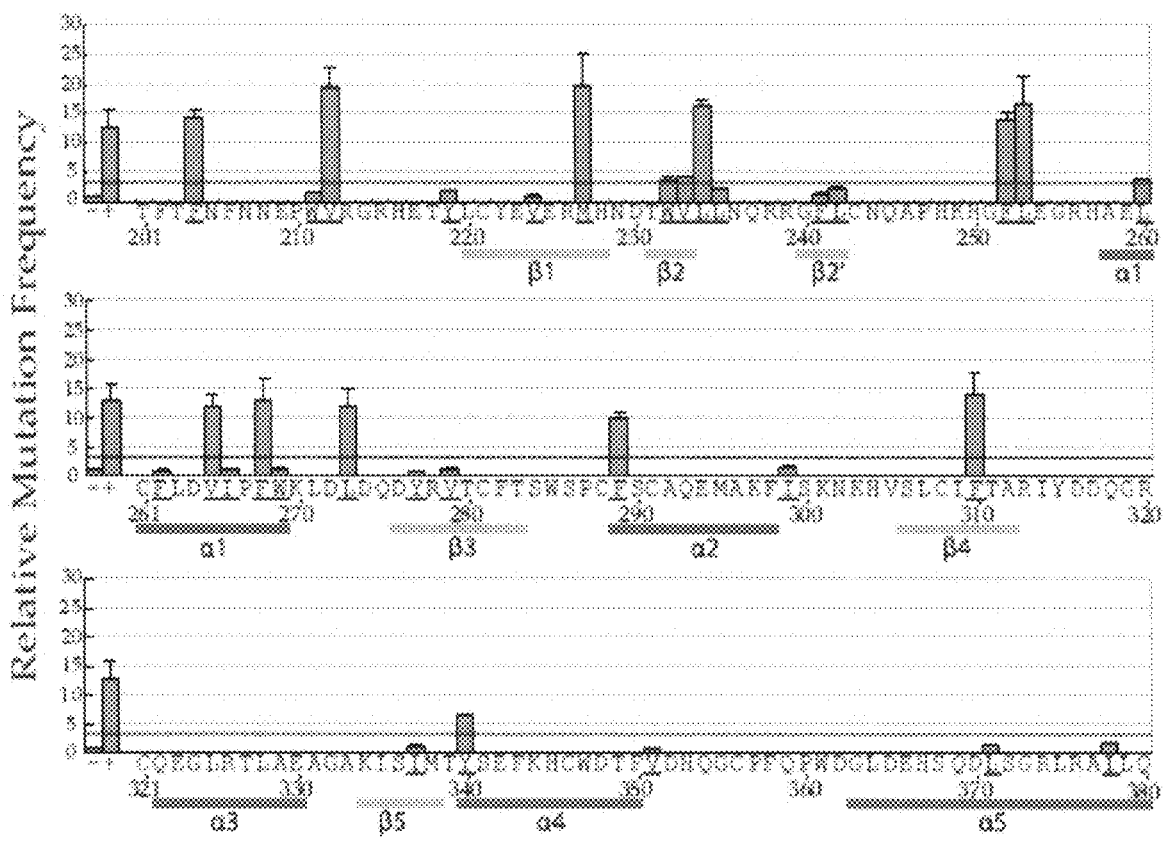
FIG. 6 contains histograms depicting the mutator phenotype of 31 A3G198-384 lysine substitution mutants. The histogram bars show the relative $Rif^R$ mutation frequencies of cells expressing the vector control (−), A3G198-384 (+) or derivatives with lysine substitutions at the underlined amino acid positions. Each histogram bar reports the average and SEM of the median mutation frequency from 2-4 independent experiments, except the bars for vector and A3G198-384, which summarize data from 12 experiments. A3G amino acids 198-200 and 381-384 were not mutated or illustrated. The primary amino acid sequence matches wildtype A3G and the secondary structure is derived from the observed A3G-2K3A solution structure.
Figure 7:
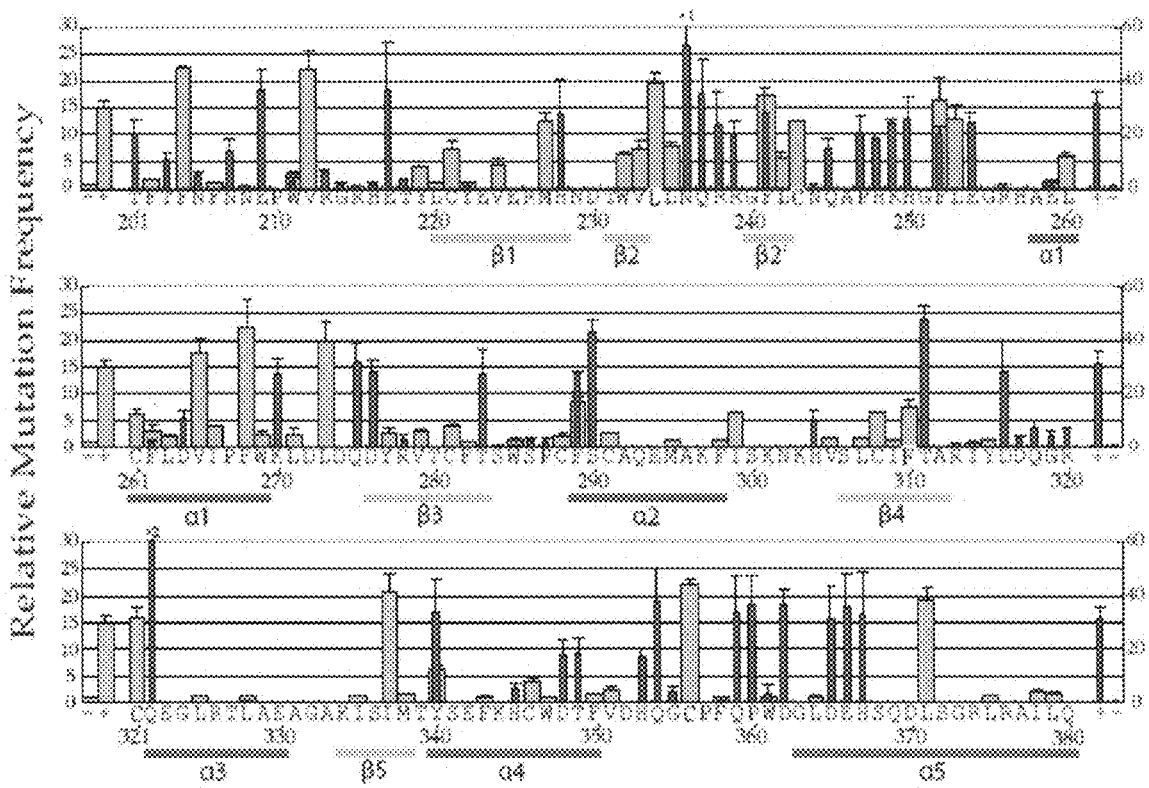
FIG. 7 depicts $Rif^R$ mutation phenotypes of A3G198-384 and A3G-2K3A alanine substitution derivatives. Data for A3G198-384 and derivative constructs are represented by left Y-axis values and grey histogram bars. These 69 mutants are shown in FIG. 3, but they are shown again here to facilitate comparisons with the A3G-2K3A alanine substitution data (represented by right Y axis values and blue histogram bars).

As discussed above, full-length human APOBEC3G is prone to aggregation and precipitation, especially at high concentrations. Residues 198-384 are sufficient for DNA deamination but similarly insoluble (see Examples 4-6). To circumvent this problem, 31 individual lysine substitution derivatives of A3G198-384 were tested for activity and solubility. Activity was measured using an *E. coli*-based Rif$^R$ mutation assay. As observed above for alanine substitutions at these positions, many of the lysine substitution mutants retained activity (FIG. 6). Several variants, including L234K and F310K, had improved solubility when assayed as described in Example 1. See Table 6. L234K and F310K were combined to yield a protein that was 2.4-fold more active and 4-fold more soluble (FIG. 8a and FIG. 6, data not shown). Three additional non-detrimental substitutions, C243A, C321A and C356A, were added to this construct to minimize the possibility of inter-molecular disulfide bond formation and maximize long-term stability (FIG. 7). The resulting variant was dubbed A3G-2K3A, and it was 2.7-fold more active and 4-fold more soluble than the parental protein (FIGS. 8a, 8b). Importantly, the DNA cytosine deamination activity of A3G-2K3A was fully dependent on the catalytic glutamate E259 (FIG. 8a).

TABLE 6

A3G-198-384 Lysine substitution mutant solubility data

| | |
|---|---|
| More soluble | 227K, 234K, 265K, 268K, 273K, 310K, 340K |
| Comparable to wild type | 204K, 211K, 212K, 219K, 232K, 233K, 235K, 241K, 242K, 252K, 253K, 260K, 269K, 289K |
| Less soluble | 224K, 262K, 266K, 279K, 277K, 299K, 351K, 378K |

As described above, gel filtration assays were used previously to show that A3G198-384 is monomeric. To bolster this finding and to assess the integrity of A3G-2K3A, the parental protein and the five-substitution derivative were compared using circular dichroism (CD) spectroscopy. The CD spectra of A3G198-384 and A3G-2K3A virtually superimposed indicating that the five-substitution derivative had intact secondary structures (FIG. 8c). Moreover, A3G-2K3A sedimentation velocity analytical ultracentrifugation profiles were nearly identical over a range of concentrations, providing strong evidence that a monomer-dimer or higher order equilibrium is not occurring (FIG. 8d). These sedimentation velocity data were also used to calculate an A3G-2K3A molecular weight of 22.3 kDa (within error of the theoretical 22.6 kDa).

A3G-2K3A was used for NMR spectroscopy experiments as described in Example 1. A total of 2,004 distance constraints were obtained and used to calculate a solution structure (FIG. 9, Tables 1 & 2). The superimposition of the ten lowest energy structures demonstrated that this enzyme has a well-defined core structure comprised of 5 β-strands and 5 α-helices, arranged from N- to C-terminus as β1-β2/2'-α1-β3-α2-β4-α3-β5-α4-α5 (FIGS. 9a, b, c). The zinc-coordinating active site, α1-β3-α2, is anchored within the platform of β strands. The catalytic site is further supported by the α4 and α5 helices, which make extensive stabilizing hydrophobic contacts with the β strand platform (FIG. 9d). The secondary structural elements are connected by loops of varying lengths, with the β3-to-α2 loop being remarkably well-defined (blue in FIG. 9b). This loop consists of S284, W285, S286 and P287, residues that are conserved among DNA deaminases and likely important for active site integrity (FIG. 10 & below).

The A3G catalytic domain shares some features with prior structures. First, the α-β-α Zn$^{2+}$-binding motif, α1-β3-α2 in A3G-2K3A, is the clearest structural feature of this deaminase superfamily e.g., 11,13-16,21 (FIG. 11, top). Second, a subset of the superfamily members, including human APOBEC3G, *S. aureus* tRNA adenosine editing protein TadA and human APOBEC2 (and likely all of the other APOBEC family members), has the β-strand of the zinc-coordinating motif and the two subsequent β strands arranged in parallel (FIG. 11, bottom). This organization is likely a key determinant of substrate specificity, enabling a loop and additional structural elements to be accommodated between the latter two β-strands. In contrast, cytidine deaminases of *E. coli, B. subtilis, S. cerevisiae* and humans have an anti-parallel β4-β5 organization separated by a small loop (FIG. 11, bottom right). Finally, closer family members, such as APOBEC2, have a common overall fold and similar secondary structures (FIGS. 11 & 12). Several prior reports have discussed and modeled this likelihood. See Conticello, et al. *Adv Immunol* 94, 37-73 (2007); Prochnow, et al. *Nature* 445, 447-451 (2007); Xie, et al. *Proc Natl Acad Sci USA* 101, 8114-8119 (2004); Huthoff. & Malim, *Virology* 334, 147-153 (2005); Zhang, et al. *PLoS ONE* 2, e378 (2007).

However, A3G-2K3A differs significantly from all prior structures. For instance, the closest family member with structural information, APOBEC2, shares 31% identity overall (FIG. 10). See Prochnow, et al., supra. The majority of these residues are located within the protein core (35/86 residues), consistent with the likelihood that these amino acids are critical for forming the overall scaffold (FIG. 12). In contrast, much less identity (11/68 residues) occurs among solvent-accessible residues, which mediate substrate recognition, catalysis and interactions with other macromolecules (FIG. 12). This makes sense in light of evolution, as more than 400 million years have passed since these two proteins were encoded by a single gene (prior to vertebrate radiation). Thus, as described below, the A3G-2K3A structure helps explain why APOBEC3G and other family members (but apparently not APOBEC2) are endowed with DNA cytosine deaminase and retrovirus restriction activities.

In addition to surface residue differences, A3G-2K3A has several remarkable structural features. First, A3G-2K3A (or a derivative with L234 restored) has a unique β2 strand, which is interrupted with a bulge of 6 residues (FIGS. 9c, 12 & 13). In contrast, APOBEC2 has a continuous 11 residue β2 strand, which mediates dimerization through a β2 strand of another molecule. The structural constraints imposed by the β2-bulge-β2' suggest that different contacts will connect N- and C-terminal domains of APOBEC3G. Alternatively, the β2-bulge-β2' may mediate interactions with RNA and/or other proteins (of cellular and/or viral origin), because it appears largely dispensable for DNA deamination activity (FIGS. 6 & 7). Second, A3G-2K3A begins with β1, whereas APOBEC2 has a small α-helix preceding its first β-strand. See Prochnow et al. supra.

Amino acid alignments suggest that residues 198-202 of APOBEC3G may form an analogous α helix (ExPASy proteomix tools, world wide web at ca.expasy.org). Finally, there are many less obvious differences between A3G-2K3A and APOBEC2 (FIGS. 10 & 12). For instance, the zinc-coordinating α1 helix in A3G-2K3A is considerably longer than the corresponding helix in APOBEC2, and the conserved S—W285-S motif in APOBEC3G and other DNA deaminases is an S-S-S motif in all known APOBEC2 proteins. Given the prominence of W285 within the APOBEC3G catalytic site (discussed further below), it is likely that the S-S-S motif of APOBEC2 contributes to this protein's substrate specificity.

A fundamental question is how APOBEC3G and related family members recognize single-strand DNA (ssDNA). Like many other nucleic acid-interacting proteins, it was thought that A3G-2K3A would have a prominent positively charged surface that would define the DNA interacting region. However, the electrostatic potential of the active site face of A3G-2K3A was largely negative apart from a few positively charged residues arranged on an apparent brim surrounding the concave active site region (FIG. 14a). To directly test whether any of these residues interacted with DNA, NMR chemical shift perturbation experiments were conducted with $^{15}$N-labeled A3G-2K3A and varying concentrations of a 21 base ssDNA oligonucleotide, which contained an APOBEC3G 5'-CC deamination hotspot. As expected, significant chemical shift perturbations occurred predominantly on the active site face of A3G-2K3A (FIGS. 14b & 15). Notable perturbations were detected for conserved arginines R215 and R313 and for the catalytic glutamate E259. Residues adjacent to R313 (within the β4-to-α3 loop) and E259 also showed strong chemical shift perturbations. The two other brim domain arginines, R213 and R320, could not be detected with this technique.

The NMR titration data were used to build a model for ssDNA binding (FIGS. 14b, 14c & 15). First, an APOBEC3G hotspot was selected that contained trinucleotide 5'-$C_1$-$C_2$-$T_3$-3' to model the DNA interaction. This short sequence was selected because ssDNA interactions were detected predominantly around the active site and this sequence spans that region. Second, the target cytosine ($C_2$) was positioned under H257, analogous to how it orients in cytidine deaminase crystal structures. Finally, all residues that showed significant chemical shift perturbations were used to calculate the lowest energy structure of an A3G-2K3A-trinucleotide 5'-$C_1$-$C_2$-$T_3$-3' complex (FIG. 14c).

One notable feature of the DNA binding model is that the target cytosine is predicted to be flipped-out from the phosphodiester backbone (i.e., without flipping it can not access the catalytic glutamate E259). A similar substrate contortion was described previously for TadA21 and a number of other DNA metabolism proteins. The model further predicted that the 5' nucleotide C1 would be sufficiently close to interact with conserved R313. C1 has a large interaction surface that contributes significantly to the overall trinucleotide binding energy (−44.7 kcal mol−1). This strong interaction may help explain the observed specificity of APOBEC3G for 5'-CC dinucleotides, which underlies the retroviral genomic strand 5'-GG to -AG hypermutation bias. It was hypothesized that DNA deaminases with different dinucleotide preferences such as AID (5'-RC) or APOBEC3F (5'-TC) will make similarly robust contacts with the 5' nucleotide. The model also predicted that the phosphate of the 3' nucleotide T3 would contact both R215 and R213 and that the C2 phosphate would interact with R320.

To test this brim domain model for DNA binding, it was asked whether conserved residues would be required for activity. The model predicted that R215 and R313 would promote DNA binding, W285 would help form the hydrophobic active site and E259, as shown previously, would mediate catalysis. As expected, all of these residues proved essential for activity (FIGS. 14d & 7). Second, since R213 and R320 were predicted to interact with the phosphate backbone of ssDNA, we hypothesized that they would be influential but non-essential for activity. Accordingly, a non-invasive substitution at these positions might be tolerated, but a negatively charged substitution might render the protein inactive by repelling the phosphate backbone. Indeed, R213A and R320A derivatives still retained 20% of wild-type activity, whereas R213E and R320E derivatives were nearly dead (FIGS. 14d & 7). Thus, the A3G-2K3A solution structure, NMR DNA titration data, computational modeling, phylogenetic conservation and DNA cytosine deaminase activity data combined to support the brim domain model for ssDNA binding.

The catalytic domain of the HIV-1 restriction factor APOBEC3G represents the first high-resolution ssDNA deaminase structure. This structure will facilitate studies on related proteins such as the mRNA editor APOBEC1, the antibody gene deaminase AID and other family members that elicit retroelement restriction activity. As a practical consideration, similar mutagenesis strategies may be used to improve the solubility of other family members. Moreover, the A3G-2K3A structure can be used to build accurate models of the N-terminal, Vif-interacting domain of APOBEC3G and therefore also models of the full-length protein.

Example 8

A3G-2K3A β2-Bulge-β2'

One of the major differences between A3G-2K3A and APOBEC2 is found in the β2 strand. The unique β2-bulge-β2' secondary structure of A3G-2K3A was not predicted by prior APOBEC3G structural modeling based on the APOBEC2 structure itself. For instance, as discussed above, the coordinates of the APOBEC2 crystal structure main chain atoms were used to generate an APOBEC3G catalytic domain model. Thus, apart from insertions and deletions, the APOBEC3G-ctd model was virtually identical to APOBEC2. However, the A3G-2K3A structure now enables specific comparisons to be made with APOBEC2. The r.m.s.d. of the Cα atoms of the A3G-2K3A NMR structure and the crystal APOBEC2 structure is 6.0 Å (calculated using data from A3G-2K3A residues Q217-N244 and E254-N381 and APOBEC2 residues R65-K224; the break in the A3G comparison region was due to the fact that this protein has a much larger loop between β2' and α1). For comparison, the r.m.s.d. of the Cα atoms of the A3G-2K3A NMR structure and the predicted A3Gctd structural model is 5.8 Å (calculated using data from residues R215-N384).

A bulge of six amino acids, K234, L235, N236, Q237, R238 and R239, interrupts the β2 region of A3G-2K3A, whereas the β2 strand of APOBEC2 is continuous. To eliminate any concern that K234 triggered the bulge, A3G-2K3A was reverse engineered to restore L234. The resulting variant, A3G-1K3A was used to obtain a $^{15}$N-$^{1}$H correlation spectrum and a $^{15}$N-edited 3D NOESY spectrum. A schematic diagram of β1, β2 and β2' of A3G-2K3A is shown in FIG. 13a. Red arrows indicate NOE interactions observed on proximal amide protons between β1 and β2 or β2'. NOE signals between these amide protons are shown in FIG. 13b (A3G-2K3A) and S5c (A3G-1K3A). These signals indicate that the interactions between β1 and β2 or β2' are identical for A3G-2K3A and A3G-1K3A. Furthermore, NOE signals between amide protons and Hα protons or between Hα and Hα protons (dashed lines in FIG. 13a) were also observed for A3G-1K3A as well as A3G-2K3A (raw data not shown). It should be noted that the A3G-2K3A sample used to take the FIG. 13b spectrum was highly deuterated (close to 100%) and, therefore, only amide proton signals were observed. The A3G-1K3A sample used to take the FIG. 13c spectrum was 90% deuterated, therefore, there were sequential NOE signals from aromatic protons including F241δ, W232δ and ε. These sequential NOEs were also observed in a $^{15}$N-edited 3D NOESY spectrum of a non-deuterated A3G-2K3A protein (data not shown). In conclusion, apart from L234 itself and a modest difference in deuteration level, A3G-2K3A and A3G-1K3A showed identical NMR spectra, and therefore these proteins have identical secondary, tertiary and quaternary structures. Thus, under the experimental conditions described herein, the β2-bulge-β2' of A3G is stable and not attributable to the L234K substitution. The current datasets cannot however discount the possibility that the presence of the N-terminal domain might trigger a dramatic restructuring of the C-terminal domain (although such a restructuring is highly restricted by the fact it must not compromise catalytic activity).

Example 9

A3G-2K3A/ssDNA Interaction Model

The NMR chemical shift perturbation experiments discussed in Example 7 and shown in FIGS. 14 and 15 used a 21 base ssDNA (5'-GCT-TCT-TCT-ACC-TTC-TCT-TGA-3', SEQ ID NO:252) because it had been characterized previously as an HIV-1 derived sequence that binds full-length APOBEC3G in vitro (P. Henry, A. Stephen and V. Pathak, NCI-Frederick, personal communication), it contained a predicted APOBEC3G deamination hotspot (5'-CC with the target cytosine underlined), and it was among the shortest sequences to trigger significant chemical shift perturbations. Shorter deoxy-oligonucleotides did not appear to bind A3G-2K3A in gel shift assays and/or cause strong chemical shift perturbations. For instance, at ssDNA to A3G-2K3A molar ratios of 8:1, significant chemical shifts were not detected for 5'-ACC-CA, 5'-AAA-CCC-AAA-A (SEQ ID NO:253) and 5'-GGG-AGA-CCC-AAA-GAG (SEQ ID NO:254) or for a transition state analogue 2'deoxy-tetra-hydroxy-uridine (dTHU).

However, at molar ratios of 4 ssDNA to 1 A3G-2K3A, a 20 base ssDNA 5'-AAA-GGG-AGA-CCC-AAA-GAG-GA (SEQ ID NO:255), a 21 base ssDNA (above) and longer deoxy-oligonucleotides could trigger significant chemical shift perturbations (FIGS. 14 and 15). The 21-mer triggered greater NMR chemical shift perturbations, and therefore these datasets were expanded upon for detailed presentation (FIGS. 14 and 15). It was further noted that the longer deoxyoligonucleotides (e.g., a 69mer) were not particularly useful for NMR experimentation because they also tended to cause line-broadening of A3G-2K3A NMR signals and more non-specific chemical shifts perturbations. Overall, these data favor a model in which the C-terminal catalytic domain of APOBEC3G binds ssDNA (>20 bases) weakly using the catalytic pocket but, the N-terminal pseudo-catalytic domain likely functions to promote stronger nucleic acid interactions. Indeed, in comparison to published dissociation constants for full-length APOBEC3G (76±21 nM for a 20 nucleotide ssDNA (Iwatani et al., supra) and 50±7 nM for a 69 nucleotide ssDNA (Chelico et al., supra)), data from NMR chemical shift perturbation experiments were used to estimate that the ssDNA dissociation constant of A3G-2K3A is minimally 450 uM. $^{15}$N-$^{1}$H HSQC NMR signals of R215, E254, R256, I314, Y315, D316 and H367 were used to estimate dissociation constants (these residues showed significant ssDNA-induced chemical shift perturbations and located near the catalytic site; FIGS. 9, 14 and 15).

Example 10

Human A3G Dimerization Domain Defined by Mutants

The C-terminal dimerization domain of human A3G was defined by amino acid substitution mutants that failed to interact with A3G$_{NTD}$ 1-196 in a yeast two-hybrid assay. Standard methods were used to show that the indicated A3G mutant-LexA DNA binding domain 'bait' construct failed to interact with a A3G$_{NTD}$ 1-196 activation domain 'prey' construct (i.e., Leu- & beta-galactosidase-negative phenotype as opposed to the positive interaction that occurs between wild-type A3G-LexA 'bait' and A3G A3G$_{NTD}$ 1-196 'prey'). See Table 7. The four regions defined by the mutations map to the same side of the structure. That is, the mutations define at least one self-interaction surface that can be disrupted to produce soluble and functional protein.

TABLE 7

| Cluster | Secondary Structure | Amino Acid Substitution(s) |
|---|---|---|
| 1 | alpha 0 (predicted) | F202I |
| | | N205K |
| | | N207K |
| | | N208S, N208K, |
| | | N208H |

TABLE 7-continued

| Cluster | Secondary Structure | Amino Acid Substitution(s) |
|---|---|---|
| 2 | beta 2' | C243G<br>C243A*<br>N244Y |
| 3 | beta 4 | F310S, F310S,<br>F310K* |
| 4 | alpha 4 | K344E<br>H345Q<br>T349P |

*These mutants made larger contribution to improved solubility and stability of A3G-2K3A.

Example 11

Additional A3G Truncations are Active

An A3G deletion construct lacking residues 1 to 190 (A3G191-384) and an A3G191-384 construct containing the 2K3A mutations (i.e., L234K, F310K, C243A, C321A, and C356A) (A3G191-384-2K3A) were produced using methods described above (e.g., Example 1). Proteins were expressed and purified as described in Example 1.

For immunoblots, proteins were produced by overnight expression at 37° C. in LB medium containing 100 μg/mL ampicillin. To induce expression, cells were diluted 1:10 in LB medium containing 100 μg/mL ampicillin and 1 mM IPTG and grown for 1 hour at 37° C. Cells were pelleted and resuspended in SDS gel loading buffer [50 mM Tris-Cl (pH 6.8), 100 mM β-mercaptoethanol, 2% SDS (w/v), 0.1% (w/v) bromophenol blue, 10% (v/v) glycerol]. Lysates were heated at 95° C. for 5 min and fractionated by SDSPAGE. Proteins were transferred to a PVDF membrane (Millipore) and probed with a rabbit anti-A 3G polyclonal serum. The primary antibody was detected by incubation with HRP-coupled anti-rabbit IgG (Bio-Rad) followed by chemiluminescent imaging (Roche).

Figure 17:
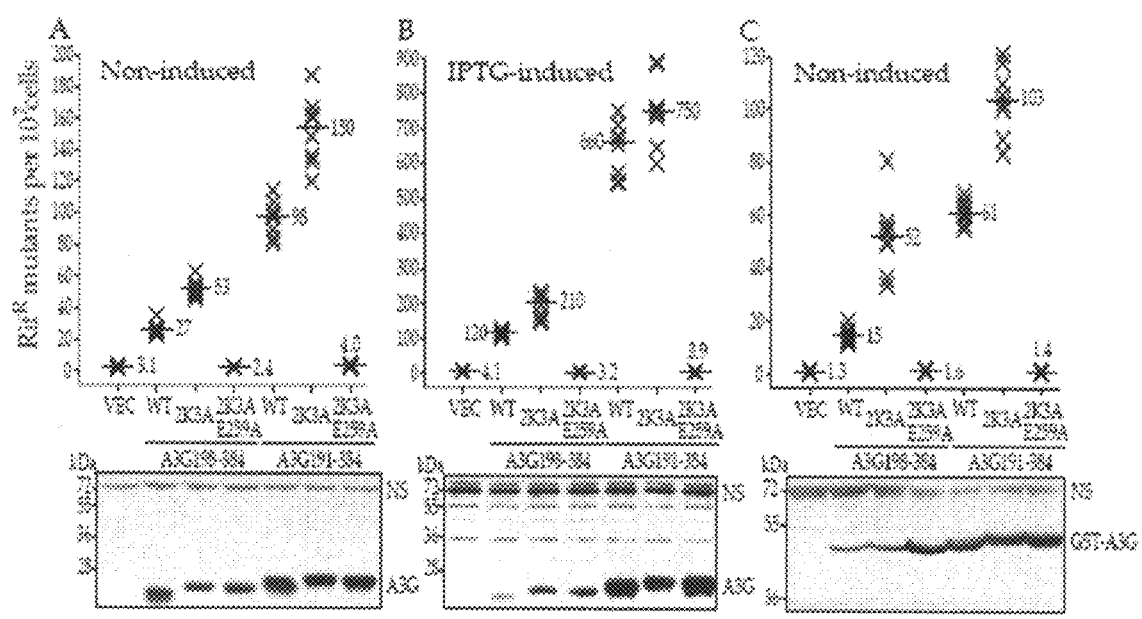

Cultures expressing A3G191-384 and A3G191-384-2K3A were tested for mutability in the E. coli-based RifR mutation assay (see Example 1) and compared with cultures expressing A3G198-384, A3G198-384-2K3A, wild-type full-length protein (A3G1-384), or full-length protein containing the 2K3A mutations (FIG. 17). Activity was dependent on the catalytic glutamate E259. Without the N-terminal GST tag, the A3G191-384 variant still elicited strong activity in this assay (which is improved with the 2K3A substitutions), whereas the activity of A3G198-384 was undetectable. Similar to A3G175-384, A3G191-384 was 3-fold more active than A3G198-384 under non-induced, basal expression conditions (FIG. 17A). 2K3A-derivatives of these constructs had even higher RifR mutation frequency increases, but A3G191-384-2K3A was still approximately 3-fold more active than A3G198-384-2K3A. Immunoblots showed that the A3G191-384 and A3G198-384 constructs are expressed similarly, indicating that the improved activity of the longer protein is not simply due to higher expression levels or improved solubility (FIG. 17A, lower panel). As expected, IPTG-induced expression of the A3G constructs resulted in the highest levels of RifR mutation, with the A3G191-384 and its 2K3A derivative easily triggering 100-fold increases over the vector control levels (FIG. 17B). Again, the A3G191-384 proteins were at least 3-fold more active than the A3G198-384 variants, but here activity appeared to correlate roughly with solubility (FIG. 17B, lower panel). Similar RifR mutation trends were observed for non-induced, GST-tagged versions of all of these A3G constructs. The GST tag was influential but not responsible for elevated catalytic activity as, for instance, it rendered the A3G198-384 construct almost as soluble as the A3G191-384 protein and it helped cause induced levels of catalytically active GST-tagged proteins to be toxic (FIG. 17C & data not shown). Overall, the E. coli activity and expression data combined to indicate that A3G191-384 is approximately 3-fold more active than the shorter A3G198-384 variant in E. coli.

Figure 18:
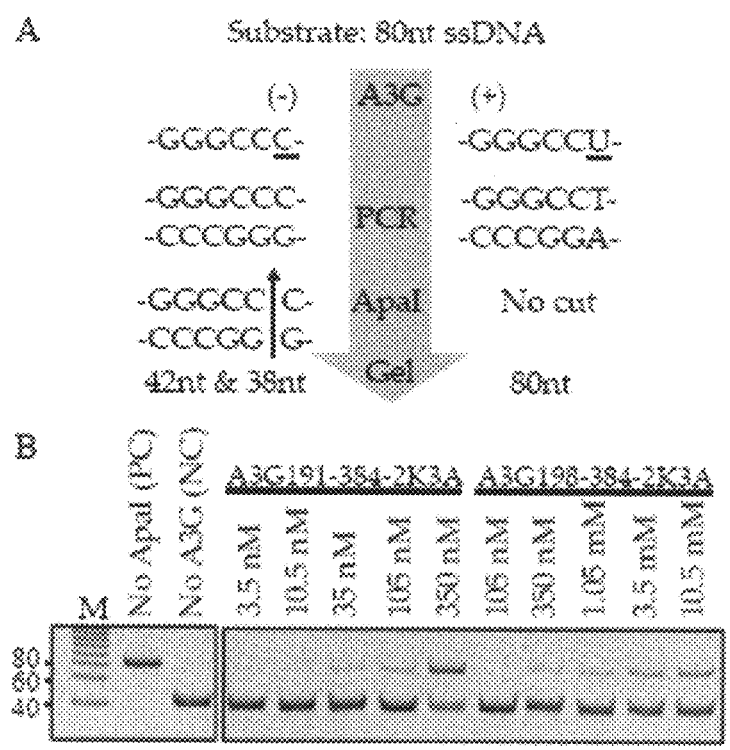

FIG. 18 shows the activity of A3G191-384-2K3A and A3G198-384-2K3A based on a quantitative in vitro single-strand DNA (ssDNA) deaminase assay. DNA cytidine deaminase activity is measured by i) incubating A3G with an 80 nucleotide ssDNA substrate containing a 5'-GGGCCCA3G target site (the strongly preferred A3G target cytidine is underlined), ii) subjecting the deamination products to PCR, which will amplify both substrate and the 5'-GGGCC Uproduct, and iii) digesting the products to completion with ApaI, which cleaves the deamination substrate but not the deamination product. The percentage of uncut PCR product thereby provides a quantitative measure of DNA cytidine deaminase activity. See, Nowarski et al., Nat. Struct. Mol. Biol. 15(10):1059-1066 (2008).

Typically, A3G deamination reactions were performed in a 10 μl reaction volume containing 25 mM Tris (pH 7.0), 0.1 mg/ml BSA and 10 fmol ssDNA substrate (5'-GGATTGGTTGGTTATTTGTTTAAGGAAGGTGGATTA-AGGGCCCAATAAGGTG A TGGAAGTTATGTTTGGTAGATTGATGG, SEQ ID NO:256). Reactions were incubated for 8 min at 37° C. and then terminated for 5 min at 95° C. One-tenth of the reaction mix was used as a PCR template for amplification by the target-flanking primers (underlined above) in 20 μl buffer S (Larova Inc.; 1 denaturation cycle at 95° C. for 3 min followed by 14 rounds of annealing at 61° C. for 30 sec and denaturation at 94° C. for 30 sec). One-fourth of each PCR reaction was incubated with 5 units ApaI (Fermentas) for 1 hr at 30° C. (the cleavage site is indicated above). The resulting restriction products were fractionated by 14% PAGE, stained with SYBR gold (Molecular Probes) diluted 1:10,000 in 1×Tris-Borate-EDTA buffer (pH 7.8), excited by UV light (302 nm), imaged by an Olympus C-5050 CCD camera and quantified using TINA2.0 densitometry software (Raytest). DNA cytosine to uracil deamination events were detected by PCR amplifying the oligo substrate, restricting the resulting PCR product with ApaI and subjecting the reaction to gel analysis. The top band represents deaminated ssDNA substrate that incurred a 5'-CCC to -CCT transition mutation that protected it from restriction endonuclease digestion, whereas the bottom band represents the restriction-susceptible input substrate (2 products of equal size). This activity assay shows that recombinant full-length A3G-myc-his is active at pico-molar concentrations, A3G191-384-2K3A is active at nano-molar concentrations and A3G198-384-2K3A activity is barely detectable. In particular, the in vitro DNA cytidine deaminase titration data showed that A3G191-384-2K3A was 10- to 100-fold more active than A3G198-384-2K3A (e.g., the 105 nM product band intensity is similar to that of the 1.05 μM reaction, respectively; FIG. 18B). These data were representative of multiple experiments, and the protein concentrations were selected specifically to show the linear activity ranges. Taken together with the E. coli activity data, it was concluded that A3G191-384-2K3A is significantly more active than A3G198-384-2K3A. The differential magnitudes of the effects in E. coli and in vitro are probably due to many factors, including the presence of a complex milieu and protein chaperones in *E. coli* (3-fold difference) versus a chemically defined buffer in vitro (10- to 100-fold difference).

To test whether the five amino acid substitutions that led to the A3 G191-384-2K3A variant had an impact on the function of the A3G holoenzyme, the HIV-1 restriction activities of wild-type A3G and a full-length 2K3A derivative were compared. HIV infectivity studies and immunoblots were performed as follows. HIV-GFP reporter viruses were produced by Fugene-mediated transfection (Roche) of 293T cells with a five plasmid cocktail (Liddament et al., *Curr. Biol.* 14(15): 1385-1391 (2004)). The HIV-GFP proviral plasmid CS-CG, the Gag-Pol expression plasmid, the Rev expression plasmid and the VSV-G envelope expression plasmid constituted 0.8 µg of the cocktail, and the vector control or the A3G expression plasmid another 0.08 µg. Virus-containing supernatants were harvested 48 hrs post-transfection and purified from cell debris by filtration (0.22 µm PVDF, Millipore). Viral supernatants (1 mL) were further purified by centrifugation through a 20% sucrose cushion (2 hr, 20,000 g). The resulting viral pellet was resuspended directly in SDS gel loading buffer (above), fractionated by SDS-PAGE, transferred to a PVDF membrane (Millipore) and probed with an anti-GFP antibody JL-8 (Invitrogen) to detect GFP, A3G-GFP or A3G-2K3AGFP. An anti-p24 monoclonal antibody (Simon et al., *J. Virol.* 71(7):5259-5267 (1997)) provided through the NIH AIDS Research and Reference Reagent Program was used as a loading control. Both monoclonal antibodies were detected using an HRP-conjugated goat anti-mouse IgG serum (Bio-Rad) followed by chemiluminescent imaging (Roche).

After harvesting viral supernatants, A3G levels in virus producing cells were monitored by extracting soluble proteins with RIPA buffer (1 hr, 4° C., gentle rotation), removing particulate by centrifugation (10 min, 20,000 g) and immunoblotting as described above. An anti-tubulin monoclonal antibody (Covance) was used for a cellular lysate loading control. Both proteins inhibited the infectivity of a Vif-deficient HIV-1 reporter virus similarly (FIG. 19A). In agreement with these infectivity data, the amount of each protein detected in cells and in viral particles was indistinguishable (FIG. 19B). Thus, these studies demonstrate that the five amino acid substitutions that were used here to render A3G191-384 amenable to solution studies do not have a significant impact on the HIV restriction activity, cellular expression level or encapsidation ability of the A3G holoenzyme. Thus, these five substitutions have not compromised the structure and function of the A3G catalytic domain, and lend additional support to the conclusion that the loop-like bulge in the β2 region is a bona fide feature of the protein.

Example 12

A3F and AID Mutants are Active

A3F deletion constructs were produced using methods similar to that described above for A3G. As indicated in FIG. 21, GST-A3Fctd(185-373) ("ctd" refers to carboxy-terminal domain (i.e., the catalytic zinc-coordinating domain) is active in an *E. coli*-based rifampicin-resistance C-to-U DNA deamination assay. The GST-A3Fctd(185-373) construct is analogous to GST-A3G-191-384, which shows a high level of DNA deaminase activity in this experimental system. Cutting the A3F protein roughly in half to isolate the minimal catalytic domain caused an approximate 5 fold increase in mutation frequency. The GST-A3Fctd(185-373) construct is more active than full-length A3F and shorter A3F C-terminal variants (192-373 or 193-373); its activity is similar to GST-A3F-186-373 and GST-A3F-170-373. The results depicted in FIG. 21 indicate that A3G and A3F can be truncated at a similar position within the overall protein sequence and yield a protein that is more active than the full-length protein. In addition, an A3F185-373 construct containing mutations at positions 302, 314, and 315 were produced using methods described above. Mutating A3F phenylalanine 302 to lysine (homologous to A3G-F310K) resulted in a further significant increase in activity. Finally, two additional substitutions, A3F-Y314A-Q315A, caused an additional increase in activity. See FIG. 22. It is noted that residues 314 and 215 are homologous to C321 and Q322 of A3G.

AID constructs containing mutations at positions 44 and/or 109 were produced using methods similar to that described above for A3G. As indicated in FIG. 24, mutating the phenylalanine at position 109 (homologous to F310 in A3G) to a lysine resulted in improved activity. Mutating the leucine at position 44 (homologous to L234 in A3G) to a lysine also helps improve AID activity.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide comprising a cytosine deaminase amino acid sequence having at least 95% sequence identity to the amino acid sequence set forth in SEQ ID NO: 2, wherein said cytosine deaminase amino acid sequence comprises an amino acid other than leucine at position 234 of SEQ ID NO: 2, wherein said cytosine deaminase amino acid sequence lacks the amino acid residues 1 to 190 of SEQ ID NO: 2.

2. The polypeptide of claim 1, wherein said cytosine deaminase amino acid sequence comprises an amino acid other than leucine at position 234 of said amino acid sequence and an amino acid other than phenylalanine at position 310 of said amino acid sequence of SEQ ID NO: 2.

3. The polypeptide of claim 1, wherein said cytosine deaminase polypeptide amino acid sequence comprises an alanine or a lysine at position 234 of said amino acid sequence.

4. The polypeptide of claim 1, wherein said cytosine deaminase polypeptide amino acid sequence further comprises an alanine, serine, or a lysine at position 310 of said amino acid sequence.

5. The polypeptide of claim 1, wherein said cytosine deaminase polypeptide amino acid sequence comprises an alanine or a lysine at position 234 of said amino acid sequence and an alanine, serine, or a lysine at position 310 of said amino acid sequence.

6. The polypeptide of claim 1, wherein said cytosine deaminase amino acid sequence further comprises an amino acid other than cysteine at position 243 of said amino acid sequence, an amino acid other than cysteine at position 321 of said amino acid sequence, or an amino acid other than cysteine at position 356 of said amino acid sequence.

7. The polypeptide of claim 6, wherein said cytosine deaminase amino acid sequence comprises an alanine or glycine at position 243 of said amino acid sequence, an alanine at position 321 of said amino acid sequence, and an alanine at position 356 of said amino acid sequence.

8. A purified mutant cytosine deaminase polypeptide, wherein said mutant cytosine deaminase polypeptide is catalytically active and has enhanced solubility relative to a corresponding cytosine deaminase, wherein said polypeptide has at least 95% sequence identity to the amino acid sequence set forth in SEQ ID NO: 2, wherein said cytosine deaminase amino acid sequence lacks the amino acid residues 1 to 190 of SEQ ID NO: 2.

9. The polypeptide of claim 8, wherein said corresponding cytosine deaminase has the amino acid sequence set forth in SEQ ID NO:2.

10. The polypeptide of claim 8, wherein said mutant cytosine deaminase polypeptide comprises an amino acid sequence set forth in SEQ ID NO :2, and wherein said mutant cytosine deaminase amino acid sequence comprises an amino acid other than leucine at position 234 of said amino acid sequence, an amino acid other than leucine at position 235 of said amino acid sequence, an amino acid other than phenylalanine at position 241 of said amino acid sequence, an amino acid other than leucine at position 253 of said amino acid sequence, an amino acid other than phenylalanine at position 310 of said amino acid sequence, or an amino acid other than leucine at position 371 of said amino acid sequence.

11. The polypeptide of claim 10, wherein said mutant cytosine deaminase amino acid sequence comprises an alanine or a lysine at position 234 of said amino acid sequence, an alanine at position 235 of said amino acid sequence, an alanine at position 241 of said amino acid sequence, an alanine or lysine at position 253 of said amino acid sequence, an alanine, serine, or lysine at position 310 of said amino acid sequence, or an alanine at the position 371 of said amino acid sequence.

12. A kit comprising a mutant cytosine deaminase polypeptide of claim 1, wherein said mutant cytosine deaminase polypeptide is catalytically active and has enhanced solubility relative to a cytosine deaminase having the amino acid sequence set forth in SEQ ID NO: 2.

13. The kit of claim 12, wherein said kit further comprises a reagent selected from the group consisting of an antibody, a buffer, a uracil DNA glycosylase, or a nucleic acid.

14. The polypeptide of claim 1, wherein said cytosine deaminase amino acid sequence has at least 98% sequence identity to the amino acid sequence set forth in SEQ ID NO:2.

15. The polypeptide of claim 1, wherein said polypeptide has the amino acid sequence set forth in SEQ ID NO: 2 wherein an amino acid other than leucine is at position 234 of SEQ ID NO: 2 and an amino acid other than phenylalanine is at position 310 of SEQ ID NO: 2.

* * * * *

SEQUENCE LISTING

```
<160> NUMBER OF SEQ ID NOS: 261

<210> SEQ ID NO 1
<211> LENGTH: 1717
<212> TYPE: DNA
<213> ORGANISM: Homo sapiens

<400> SEQUENCE: 1
ctgccagggg gagggcccca gagaaaacca gaaagagggt gagagactga ggaagataaa      60
gcgtcccagg gcctcctaca ccagcgcctg agcaggaagc gggaggggcc atgactacga     120
ggccctggga ggtcacttta gggagggctg tcctaaaacc agaagcttgg agcagaaagt     180
gaaaccctgg tgctccagac aaagatctta gtcgggacta gccggccaag gatgaagcct     240
```

```
cacttcagaa acacagtgga gcgaatgtat cgagacacat tctcctacaa cttttataat    300
agacccatcc tttctcgtcg gaataccgtc tggctgtgct acgaagtgaa aacaaagggt    360
ccctcaaggc cccctttgga cgcaaagatc tttcgaggcc aggtgtattc cgaacttaag    420
taccacccag agatgagatt cttccactgg ttcagcaagt ggaggaagct gcatcgtgac    480
caggagtatg aggtcacctg gtacatatcc tggagcccct gcacaaagtg tacaagggat    540
atggccacgt tcctggccga ggacccgaag gttaccctga ccatcttcgt tgcccgcctc    600
tactacttct gggacccaga ttaccaggag gcgcttcgca gcctgtgtca gaaaagagac    660
ggtccgcgtg ccaccatgaa gatcatgaat tatgacgaat tcagcactg ttggagcaag     720 ttcgtgtaca gccaaagaga gctatttgag ccttggaata atctgcctaa atattatata    780
ttactgcaca tcatgctggg ggagattctc agacactcga tggatccacc acattcact     840 ttcaacttta caatgaacc ttgggtcaga ggacggcatg agacttacct gtgttatgag      900
gtggagcgca tgcacaatga cacctgggtc ctgctgaacc agcgcagggg ctttctatgc    960
aaccaggctc acataaaca cggtttcctt gaaggccgcc atgcagagct gtgcttcctg     1020
gacgtgattc ccttttggaa gctggacctg gaccaggact cagggttac ctgcttcacc     1080 tcctggagcc cctgcttcag ctgtgcccag gaaatggcta aattcatttc aaaaaacaaa    1140
cacgtgagcc tgtgcatctt cactgcccgc atctatgatg atcaaggaag atgtcaggag    1200
gggctgcgca ccctggccga ggctggggcc aaaatttcaa taatgacata cagtgaattt    1260
aagcactgct gggacacctt tgtggaccac cagggatgtc ccttccagcc ctgggatgga    1320
ctagatgagc acagccaaga cctgagtggg aggctgcggg ccattctcca gaatcaggaa    1380
aactgaagga tgggcctcag tctctaagga aggcagagac ctgggttgag cctcagaata    1440
aaagatcttc ttccaagaaa tgcaaacagg ctgttcacca ccatctccag ctgatcacag    1500
acaccagcaa agcaatgcac tcctgaccaa gtagattctt ttaaaaatta gagtgcatta    1560
ctttgaatca aaaatttatt tatatttcaa gaataaagta ctaagattgt gctcaataca    1620
cagaaaagtt tcaaacctac taatccagcg acaatttgaa tcggttttgt aggtagagga    1680
ataaaatgaa atactaaatc tttctgtaaa aaaaaaa                             1717
```

<210> SEQ ID NO 2
<211> LENGTH: 384
<212> TYPE: PRT
<213> ORGANISM: Homo sapiens

<400> SEQUENCE: 2

```
Met Lys Pro His Phe Arg Asn Thr Val Glu Arg Met Tyr Arg Asp Thr
 1               5                  10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Glu Leu Lys Tyr
    50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
```

```
                    115                 120                 125
Pro Asp Tyr Gln Glu Ala Leu Arg Ser Leu Cys Gln Lys Arg Asp Gly
130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                    165                 170                 175

Asn Leu Pro Lys Tyr Tyr Ile Leu Leu His Ile Met Leu Gly Glu Ile
                180                 185                 190

Leu Arg His Ser Met Asp Pro Pro Thr Phe Thr Phe Asn Phe Asn Asn
            195                 200                 205

Glu Pro Trp Val Arg Gly Arg His Glu Thr Tyr Leu Cys Tyr Glu Val
210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                    245                 250                 255

His Ala Glu Leu Cys Phe Leu Asp Val Ile Pro Phe Trp Lys Leu Asp
                260                 265                 270

Leu Asp Gln Asp Tyr Arg Val Thr Cys Phe Thr Ser Trp Ser Pro Cys
            275                 280                 285

Phe Ser Cys Ala Gln Glu Met Ala Lys Phe Ile Ser Lys Asn Lys His
        290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                    325                 330                 335

Ile Met Thr Tyr Ser Glu Phe Lys His Cys Trp Asp Thr Phe Val Asp
                340                 345                 350

His Gln Gly Cys Pro Phe Gln Pro Trp Asp Gly Leu Asp Glu His Ser
            355                 360                 365

Gln Asp Leu Ser Gly Arg Leu Arg Ala Ile Leu Gln Asn Gln Glu Asn
        370                 375                 380

<210> SEQ ID NO 3
<211> LENGTH: 4706
<212> TYPE: DNA
<213> ORGANISM: Homo sapiens

<400> SEQUENCE: 3 ttcccttgc  aattgccttg  ggtcctgccg  cacagagcgg  cctgtcttta  tcagaggtcc    60
ctctgccagg  gggagggccc  cagagaaaac  cagaaagagg  gtgagagact  gaggaagata   120
aagcgtccca  gggcctccta  caccagcgcc  tgagcaggaa  ggggagggg   ccatgactac   180 gaggccctgg  gaggtcactt  tagggagggc  tgtcctgaaa  cctggagcct  ggagcagaaa   240
gtgaaaccct  ggtgctccag  acaaagatct  tagtcgggac  tagccggcca  aggatgaagc   300
ctcacttcag  aaacacagtg  gagcgaatgt  atcgagacac  attctcctac  aacttttata   360
atagacccat  cctttctcgt  cggaataccg  tctggctgtg  ctacgaagtg  aaaacaaagg   420
gtccctcaag  gccccgtttg  gacgcaaaga  tctttcgagg  ccaggtgtat  cccagcctg    480 agcaccacgc  agaaatgtgc  ttcctctctt  ggttctgtgg  caaccagctg  cctgcttaca   540
agtgtttcca  gatcacctgg  tttgtatcct  ggacccctg   cccggactgt  gtggcgaagc   600
tggccgaatt  cctggctgag  caccccaatg  tcaccctgac  catctccgcc  gcccgcctct   660
```

```
actactactg ggaaagagat taccgaaggg cgctctgcag gctgagtcag gcaggggccc    720
gcgtgaagat tatggacgat gaagaatttg catactgctg ggaaaacttt gtgtacagtg    780
aaggtcagcc attcatgcct tggtacaaat tcgatgacaa ttatgcattc ctgcaccgca    840
cgctaaagga gattctcaga aacccgatgg aggcaatgta tccacacata ttctacttcc    900
actttaaaaa cctacgcaaa gcctatggtc ggaacgaaag ctggctgtgc ttcaccatgg    960
aagttgtaaa gcaccactca cctgtctcct ggaagagggg cgtcttccga accaggtgg    1020 atcctgagac ccattgtcat gcagaaaggt gcttcctctc ttggttctgt gacgacatac   1080
tgtctcctaa cacaaactac gaggtcacct ggtacacatc ttggagccct tgcccagagt   1140
gtgcagggga ggtggccgag ttcctggcca ggcacagcaa cgtgaatctc accatcttca   1200
ccgcccgcct ctactacttc tgggatacag attaccagga ggggctccgc agcctgagtc   1260 aggaagggc ctccgtggag atcatgggct acaaagattt taaatattgt tgggaaaact    1320
ttgtgtacaa tgatgatgag ccattcaagc cttggaaagg actaaaatac aactttctat   1380
tcctggacag caagctgcag gagattctcg agtgaggggt ctccccgggc tcatggtct    1440 gtctcctcta gcctcctgct catgttgtgc aggcctcccc tccatcctgg accagctgtg   1500
cttttgcctg gtcatcctga gcccctcctg gcctcagggc cattccatag tgctcccctg   1560
cctcaccacc tcctctccgc tctcccaggc tcttcctgca gaggcctctt tctgcctcca   1620
tggctatcca tccacccacc aagaccctgt tccctgagcc tgcatgcccc taacctgcct   1680
tttcccatct ccccagcata acctaatatt tttttttttt ttttgagacg gaatttcgct   1740
ctgtcaccca gactggagtg caatggcttg atcttggctc actgcaaact ctgcctacca   1800
ggttcaagcg attctcctgc ctcgcctcc cgagtagctg gaattacaga cgcctgccac    1860
cacgcacagc taacttttt ttttttgta ttttagtag tgactgggtt tcaccatgtt     1920
ggccaggctg gtcttgaact cctgacctca ggtgatccgc ctatctcagc ctcccaaagt   1980
gctgggatta caggcgtgag ccactggccc ggcggcacaa ccaaatctta ttaaactcac   2040
cctaggctgg ccgcggtgac tcatgcctat aatcccccag caatttggga ggcagaggtg   2100
agagaatcgc ttgagcccag gaattcgaga ccagcctggg ccacatgaca aagccccatc   2160
tctacaaaaa aattacaaaa aaaaaaaaa caggtgtggt ggcatgcacc tgtagttgaa    2220
gctacttgga aggatgaagt gggaggattg cttgagccgg ggaggtggag gctgcagtga   2280
actgagatca cgtcactgaa ctccagtctg agcaacagat cgagaccctg cctgaaaata   2340
aatcaataaa taaactcaac cgaaatgggt atgaaagttg aaatgggtat gtaagttgaa   2400
aaccagaagt tttgagaaac atcctttgtt aactttcatc ctacaaattg ggtcattcat   2460
gtcctacgca gctaaaacag agcccaggag ccagggagga aaagcagtca ggccacacac   2520
cattgctccc aaaatggact tctctgcaag cctgactcct gaaactgtgc attgtaccct   2580
gaaaccagct ttatccatag cttctgcaat aaatggctgt aagtcttgga ctccttgcta   2640
taatcgcagc tattcagcaa tggaacctcc cagttcccaa cccttcctag tgcccatggg   2700
ctttcccata ggacaagaga acatttctcc ttttcttttt tttttctttt gaaatggagt   2760
ctcgccctgt cacccaggct ggagtgcaat ggtgcggtct cggctcactg caacctctgc   2820
ctcccttgtt caagtgattc tcctgtctca gcctcccgag tagctgggat tacaggcgtc   2880
caccaccaaa ccaggctaat ttttgtattt ttcataaaaa cgggtttcat catgtttccc   2940
aggctggtct tatttttatt ttatttttg agatggagtc ttgctctgtt gcccaggctg   3000
gggtgcagtg gtgcaatctg ggttcactgc agcctctgcc gcctgagttc aagctatttt   3060
```

-continued

```
cctacctaag cctcccaagt agctgggatt acatgcgcgt gccaccacgc ctagctaatt      3120
tttgtgtttt tagtagagac ggggtttcaa catcttgacc aggctggtct tgaactcctg      3180
acctcgtgat ccacccgtct cggcctccca aagtgctggg attacaggcg tgagccacct      3240
ggccaggctt aggctggtct taaactcctg acctcaagtg atccaacctc cttggcctcc      3300
caaattgctg ggattgctgg tgtgagccac agcgcctagc ccatttctcc ttttaatagg      3360
acctgttgct gtctctgttc tcccaacatg gtgaacacca cccggactgc gtgtatgtcc      3420
caaattacaa ttcttcttt gcaaatgaaa tgtgaaattt agaggccctt ctccacactt       3480
taaatttgac ttgacatttt ctaggcagat ataagttatt agagaatgag attctctata      3540
aaaatgatcc cttcatgctg tggcctccac agaagatgcc ctgggccagg tgcccacatg      3600
aataatgcgg ccacaggca ggcatttatt ttctcacaga tatggaggct acaagtccaa       3660
ggtggagggg tcggcggggt tgtttgctct gaggccgctc ctcctggatg cagggatcc       3720 cttctgctg tgtcctctgt ggcctttcct ctatgaacct gtactgtacc tctgggtct       3780 ctctgcttcc aaatatcttt tttttttttt tcagacagtt ttgctcttgt tttctaggct      3840
ggagtgcaat ggcacaatct cagctcactg caacctctgc cttccgagtt caagcgattc      3900
tcgtgcctca gcctcctgag tagctgggac tacaggcgtg tgccaccacg cctggctaat      3960
tttgtagttt tagtagagac ggggtttctc catgttgctc aggctggtct tgaactcatg      4020
agctcaggcg atccactctc ctcagcctcc caaagtgctg ggattacaga tataagccac      4080
catacacaac ttttttttt ttttgagatg gagtttcact ctgttgccca ggctggagtg      4140
ctaaatagca gaatcactgc tcactgcaac ctctgcctgc tgggttcaag caattctccc      4200
acctcagcct cctgagtagc tgggattaca gatgcccaga accaatctct gctaattttt      4260
ctatttttta gtagagatgg ggtttcactg aggaaggaga ccacctctct cattgtctcc      4320
tatttcagaa ggaagcaaaa agttagaaag atgcagaagt aagatcaatg gccagactgt      4380
ttggcgctgc tacctgggcc tggtagttaa agatcaactc ctgacctgac cgcttgtttt      4440
atctaaagat tccagacatt gtatgaggaa gcattgtgaa actttctggt ctgttctgct      4500
agcccccacc actgatgcat gtagccccc agtcacgtag cccacgcttg cacaatctat       4560 cacgacccctt tcacgtggac cccttagaat tgtaagccct taaaagggcc agggacttct     4620
tcagggagct ccaatcttca gatgcaagtc tgtcaacgct cccagctgat taagcctct       4680 tccttcctaa aaaaaaaaaa aaaaaa                                           4706
```

<210> SEQ ID NO 4
<211> LENGTH: 373
<212> TYPE: PRT
<213> ORGANISM: Homo sapiens

<400> SEQUENCE: 4

```
Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Arg
        35                  40                  45

Leu Asp Ala Lys Ile Phe Arg Gly Gln Val Tyr Ser Gln Pro Glu His
    50                  55                  60

His Ala Glu Met Cys Phe Leu Ser Trp Phe Cys Gly Asn Gln Leu Pro
65                  70                  75                  80

Ala Tyr Lys Cys Phe Gln Ile Thr Trp Phe Val Ser Trp Thr Pro Cys
```

```
                    85                  90                  95
Pro Asp Cys Val Ala Lys Leu Ala Glu Phe Leu Ala Glu His Pro Asn
            100                 105                 110
Val Thr Leu Thr Ile Ser Ala Ala Arg Leu Tyr Tyr Tyr Trp Glu Arg
            115                 120                 125
Asp Tyr Arg Arg Ala Leu Cys Arg Leu Ser Gln Ala Gly Ala Arg Val
            130                 135                 140
Lys Ile Met Asp Asp Glu Glu Phe Ala Tyr Cys Trp Glu Asn Phe Val
145                 150                 155                 160
Tyr Ser Glu Gly Gln Pro Phe Met Pro Trp Tyr Lys Phe Asp Asp Asn
                165                 170                 175
Tyr Ala Phe Leu His Arg Thr Leu Lys Glu Ile Leu Arg Asn Pro Met
            180                 185                 190
Glu Ala Met Tyr Pro His Ile Phe Tyr Phe His Phe Lys Asn Leu Arg
            195                 200                 205
Lys Ala Tyr Gly Arg Asn Glu Ser Trp Leu Cys Phe Thr Met Glu Val
            210                 215                 220
Val Lys His His Ser Pro Val Ser Trp Lys Arg Gly Val Phe Arg Asn
225                 230                 235                 240
Gln Val Asp Pro Glu Thr His Cys His Ala Glu Arg Cys Phe Leu Ser
                245                 250                 255
Trp Phe Cys Asp Asp Ile Leu Ser Pro Asn Thr Asn Tyr Glu Val Thr
            260                 265                 270
Trp Tyr Thr Ser Trp Ser Pro Cys Pro Glu Cys Ala Gly Glu Val Ala
            275                 280                 285
Glu Phe Leu Ala Arg His Ser Asn Val Asn Leu Thr Ile Phe Thr Ala
            290                 295                 300
Arg Leu Tyr Tyr Phe Trp Asp Thr Asp Tyr Gln Glu Gly Leu Arg Ser
305                 310                 315                 320
Leu Ser Gln Glu Gly Ala Ser Val Glu Ile Met Gly Tyr Lys Asp Phe
                325                 330                 335
Lys Tyr Cys Trp Glu Asn Phe Val Tyr Asn Asp Asp Glu Pro Phe Lys
            340                 345                 350
Pro Trp Lys Gly Leu Lys Tyr Asn Phe Leu Phe Leu Asp Ser Lys Leu
            355                 360                 365
Gln Glu Ile Leu Glu
            370

<210> SEQ ID NO 5
<211> LENGTH: 2790
<212> TYPE: DNA
<213> ORGANISM: Homo sapiens

<400> SEQUENCE: 5
gaaccatcat taattgaagt gagatttttc tggcctgaga cttgcaggga ggcaagaaga      60
cactctggac accactatgg acagcctctt gatgaaccgg aggaagtttc tttaccaatt     120
caaaaatgtc cgctgggcta agggtcggcg tgagacctac ctgtgctacg tagtgaagag     180
gcgtgacagt gctacatcct tttcactgga ctttggttat cttcgcaata agaacggctg     240
ccacgtggaa ttgctcttcc tccgctacat ctcggactgg gacctagacc ctggccgctg     300
ctaccgcgtc acctggttca cctcctggag ccctgctac gactgtgccc gacatgtggc     360
cgactttctg cgagggaacc caacctcag tctgaggatc ttcaccgcgc gcctctactt     420
ctgtgaggac cgcaaggctg agcccgaggg gctgcggcgg ctgcaccgcg ccggggtgca     480
```

```
aatagccatc atgaccttca aagattattt ttactgctgg aatactttg tagaaaacca      540
tgaaagaact ttcaaagcct gggaagggct gcatgaaaat tcagttcgtc tctccagaca     600
gcttcggcgc atccttttgc ccctgtatga ggttgatgac ttacgagacg catttcgtac     660
tttgggactt tgatagcaac ttccaggaat gtcacacacg atgaaatatc tctgctgaag    720
acagtggata aaaacagtc cttcaagtct tctctgtttt tattcttcaa ctctcactt      780
cttagagttt acagaaaaaa tatttatata cgactcttta aaaagatcta tgtcttgaaa    840
atagagaagg aacacaggtc tggccaggga cgtgctgcaa ttggtgcagt tttgaatgca    900
acattgtccc ctactgggaa taacagaact gcaggacctg ggagcatcct aaagtgtcaa    960
cgttttcta tgacttttag gtaggatgag agcagaaggt agatcctaaa aagcatggtg    1020
agaggatcaa atgtttttat atcaacatcc tttattatt gattcatttg agttaacagt    1080
ggtgttagtg atagatttt ctattctttt cccttgacgt ttactttcaa gtaacacaaa    1140
ctcttccatc aggccatgat ctataggacc tcctaatgag agtatctggg tgattgtgac   1200
cccaaaccat ctctccaaag cattaatatc caatcatgcg ctgtatgttt taatcagcag   1260
aagcatgttt ttatgtttgt acaaaagaag attgttatgg gtggggatgg aggtatagac   1320
catgcatggt caccttcaag ctactttaat aaaggatctt aaaatgggca ggaggactgt    1380
gaacaagaca ccctaataat gggttgatgt ctgaagtagc aaatcttctg gaaacgcaaa    1440
ctcttttaag gaagtcccta atttagaaac acccacaaac ttcacatatc ataattagca   1500
aacaattgga aggaagttgc ttgaatgttg gggagaggaa aatctattgg ctctcgtggg   1560
tctcttcatc tcagaaatgc caatcaggtc aaggtttgct acattttgta tgtgtgtgat    1620
gcttctccca aaggtatatt aactatataa gagagttgtg acaaaacaga atgataaagc    1680
tgcgaaccgt ggcacacgct catagttcta gctgcttggg aggttgagga gggaggatgg    1740
cttgaacaca ggtgttcaag gccagcctgg gcaacataac aagatcctgt ctctcaaaaa    1800
aaaaaaaaaa aaaagaaag agagagggcc gggcgtggtg gctcacgcct gtaatcccag    1860
cactttggga ggccgagccg ggcggatcac ctgtggtcag gagtttgaga ccagcctggc   1920
caacatggca aaacccccgtc tgtactcaaa atgcaaaaat tagccaggcg tggtagcagg   1980
caccttgtaat cccagctact ggaggctg aggcaggaga atcgcttgaa cccaggaggt    2040
ggaggttgca gtaagctgag atcgtgccgt gcactccag cctgggcgac aagagcaaga    2100
ctctgtctca gaaaaaaaa aaaaaaagag agagagagag aaagagaaca atatttggga    2160
gagaaggatg gggaagcatt gcaaggaaat tgtgctttat ccaacaaaat gtaaggagcc    2220
aataagggat ccctatttgt ctcttttggt gtctatttgt ccctaacaac tgtctttgac   2280
agtgagaaaa atattcagaa taaccatatc cctgtgccgt tattacctag caacccttgc   2340
aatgaagatg agcagatcca caggaaaact tgaatgcaca actgtcttat tttaatctta    2400
ttgtacataa gtttgtaaaa gagttaaaaa ttgttacttc atgtattcat ttatatttta   2460
tattattttg cgtctaatga ttttttatta acatgatttc cttttctgat atattgaaat   2520
ggagtctcaa agcttcataa atttataact ttagaaatga ttctaataac aacgtatgta    2580
attgtaacat tgcagtaatg gtgctacgaa gccatttctc ttgattttta gtaaactttt   2640
atgacagcaa atttgcttct ggctcacttt caatcagtta aataaatgat aaataatttt   2700
ggaagctgtg aagataaaat accaaataaa ataatataaa agtgatttat atgaagttaa    2760
aataaaaaat cagtatgatg gaataaactt                                     2790
```

<210> SEQ ID NO 6

```
<211> LENGTH: 198
<212> TYPE: PRT
<213> ORGANISM: Homo sapiens

<400> SEQUENCE: 6

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 7
<211> LENGTH: 182
<212> TYPE: PRT
<213> ORGANISM: Homo sapiens

<400> SEQUENCE: 7

Asp Pro Pro Thr Phe Thr Phe Asn Phe Asn Asn Glu Pro Trp Val Arg
1               5                   10                  15

Gly Arg His Glu Thr Tyr Leu Cys Tyr Glu Val Glu Arg Met His Asn
            20                  25                  30

Asp Thr Trp Val Leu Leu Asn Gln Arg Arg Gly Phe Leu Cys Asn Gln
        35                  40                  45

Ala Pro His Lys His Gly Phe Leu Glu Gly Arg His Ala Glu Leu Cys
    50                  55                  60

Phe Leu Asp Val Ile Pro Phe Trp Lys Leu Asp Leu Asp Gln Asp Tyr
65                  70                  75                  80

Arg Val Thr Cys Phe Thr Ser Trp Ser Pro Cys Phe Ser Cys Ala Gln
                85                  90                  95

Glu Met Ala Lys Phe Ile Ser Lys Asn Lys His Val Ser Leu Cys Ile
            100                 105                 110

Phe Thr Ala Arg Ile Tyr Asp Asp Gln Gly Arg Cys Gln Glu Gly Leu
        115                 120                 125

Arg Thr Leu Ala Glu Ala Gly Ala Lys Ile Ser Ile Met Thr Tyr Ser
    130                 135                 140
```

```
Glu Phe Lys His Cys Trp Asp Thr Phe Val Asp His Gln Gly Cys Pro
145                 150                 155                 160

Phe Gln Pro Trp Asp Gly Leu Asp Glu His Ser Gln Asp Leu Ser Gly
            165                 170                 175

Arg Leu Arg Ala Ile Leu
            180

<210> SEQ ID NO 8
<211> LENGTH: 176
<212> TYPE: PRT
<213> ORGANISM: Homo sapiens

<400> SEQUENCE: 8

Pro Ala Asn Phe Phe Lys Phe Gln Phe Arg Asn Val Glu Tyr Ser Ser
1               5                   10                  15

Gly Arg Asn Lys Thr Phe Leu Cys Tyr Val Val Glu Ala Gln Gly Lys
            20                  25                  30

Gly Gly Gln Val Gln Ala Ser Arg Gly Tyr Leu Glu Asp Glu His Ala
        35                  40                  45

Ala Ala His Ala Glu Glu Ala Phe Phe Asn Thr Ile Leu Pro Ala Phe
50                  55                  60

Asp Pro Ala Leu Arg Tyr Asn Val Thr Trp Tyr Val Ser Ser Ser Pro
65                  70                  75                  80

Cys Ala Ala Cys Ala Asp Arg Ile Ile Lys Thr Leu Ser Lys Thr Lys
                85                  90                  95

Asn Leu Arg Leu Leu Ile Leu Val Gly Arg Leu Phe Met Trp Glu Glu
            100                 105                 110

Pro Glu Ile Gln Ala Ala Leu Lys Lys Leu Lys Glu Ala Gly Cys Lys
        115                 120                 125

Leu Arg Ile Met Lys Pro Gln Asp Phe Glu Tyr Val Trp Gln Asn Phe
130                 135                 140

Val Glu Gly Glu Glu Gly Glu Ser Lys Ala Phe Gln Pro Trp Glu Asp
145                 150                 155                 160

Ile Gln Glu Asn Phe Leu Tyr Tyr Glu Glu Lys Leu Ala Asp Ile Leu
                165                 170                 175

<210> SEQ ID NO 9
<211> LENGTH: 187
<212> TYPE: PRT
<213> ORGANISM: Homo sapiens

<400> SEQUENCE: 9

Asp Pro Pro Thr Phe Thr Phe Asn Phe Asn Asn Glu Pro Trp Val Arg
1               5                   10                  15

Gly Arg His Glu Thr Tyr Leu Cys Tyr Glu Val Glu Arg Met His Asn
            20                  25                  30

Asp Thr Trp Val Leu Leu Asn Gln Arg Arg Gly Phe Leu Cys Asn Gln
        35                  40                  45

Ala Pro His Lys His Gly Phe Leu Glu Gly Arg His Ala Glu Leu Cys
50                  55                  60

Phe Leu Asp Val Ile Pro Phe Trp Lys Leu Asp Leu Asp Gln Asp Tyr
65                  70                  75                  80

Arg Val Thr Cys Phe Thr Ser Trp Ser Pro Cys Phe Ser Cys Ala Gln
                85                  90                  95

Glu Met Ala Lys Phe Ile Ser Lys Asn Lys His Val Ser Leu Cys Ile
            100                 105                 110

Phe Thr Ala Arg Ile Tyr Asp Asp Gln Gly Arg Cys Gln Glu Gly Leu
```

```
            115                 120                 125
Arg Thr Leu Ala Glu Ala Gly Ala Lys Ile Ser Ile Met Thr Tyr Ser
    130                 135                 140

Glu Phe Lys His Cys Trp Asp Thr Phe Val Asp His Gln Gly Cys Pro
145                 150                 155                 160

Phe Gln Pro Trp Asp Gly Leu Asp Glu His Ser Gln Asp Leu Ser Gly
                165                 170                 175

Arg Leu Arg Ala Ile Leu Gln Asn Gln Glu Asn
        180                 185

<210> SEQ ID NO 10
<211> LENGTH: 186
<212> TYPE: PRT
<213> ORGANISM: Homo sapiens

<400> SEQUENCE: 10

Asp Pro His Ile Phe Thr Ser Asn Phe Asn Asn Gly Ile Gly Arg His
1               5                   10                  15

Lys Thr Tyr Leu Cys Tyr Glu Val Glu Arg Leu Asp Asn Gly Thr Ser
            20                  25                  30

Val Lys Met Asp Gln His Arg Gly Phe Leu His Asn Gln Ala Lys Asn
        35                  40                  45

Leu Leu Cys Gly Phe Tyr Gly Arg His Ala Glu Leu Arg Phe Leu Asp
    50                  55                  60

Leu Val Pro Ser Leu Gln Leu Asp Pro Ala Gln Ile Tyr Arg Val Thr
65                  70                  75                  80

Trp Phe Ile Ser Trp Ser Pro Cys Phe Ser Trp Gly Cys Ala Gly Glu
                85                  90                  95

Val Arg Ala Phe Leu Gln Glu Asn Thr His Val Arg Leu Arg Ile Phe
            100                 105                 110

Ala Ala Arg Ile Tyr Asp Tyr Asp Pro Leu Tyr Lys Glu Ala Leu Gln
        115                 120                 125

Met Leu Arg Asp Ala Gly Ala Gln Val Ser Ile Met Thr Tyr Asp Glu
    130                 135                 140

Phe Lys His Cys Trp Asp Thr Phe Val Asp His Gln Gly Cys Pro Phe
145                 150                 155                 160

Gln Pro Trp Asp Gly Leu Asp Glu His Ser Gln Ala Leu Ser Gly Arg
                165                 170                 175

Leu Arg Ala Ile Leu Gln Asn Gln Gly Asn
        180                 185

<210> SEQ ID NO 11
<211> LENGTH: 189
<212> TYPE: PRT
<213> ORGANISM: Homo sapiens

<400> SEQUENCE: 11

Asp Pro Asp Thr Phe Thr Phe Asn Phe Asn Asn Asp Pro Leu Val Leu
1               5                   10                  15

Arg Arg Arg Gln Thr Tyr Leu Cys Tyr Glu Val Glu Arg Leu Asp Asn
            20                  25                  30

Gly Thr Trp Val Leu Met Asp Gln His Met Gly Phe Leu Cys Asn Glu
        35                  40                  45

Ala Lys Asn Leu Leu Cys Gly Phe Tyr Gly Arg His Ala Glu Leu Arg
    50                  55                  60

Phe Leu Asp Leu Val Pro Ser Leu Gln Leu Asp Pro Ala Gln Ile Tyr
65                  70                  75                  80
```

Arg Val Thr Trp Phe Ile Ser Trp Ser Pro Cys Phe Ser Trp Gly Cys
                85                  90                  95

Ala Gly Glu Val Arg Ala Phe Leu Gln Glu Asn Thr His Val Arg Leu
            100                 105                 110

Arg Ile Phe Ala Ala Arg Ile Tyr Asp Tyr Asp Pro Leu Tyr Lys Glu
        115                 120                 125

Ala Leu Gln Met Leu Arg Asp Ala Gly Ala Gln Val Ser Ile Met Thr
130                 135                 140

Tyr Asp Glu Phe Glu Tyr Cys Trp Asp Thr Phe Val Tyr Arg Gln Gly
145                 150                 155                 160

Cys Pro Phe Gln Pro Trp Asp Gly Leu Glu Glu His Ser Gln Ala Leu
                165                 170                 175

Ser Gly Arg Leu Arg Ala Ile Leu Gln Asn Gln Gly Asn
            180                 185

<210> SEQ ID NO 12
<211> LENGTH: 190
<212> TYPE: PRT
<213> ORGANISM: Homo sapiens

<400> SEQUENCE: 12

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg
            180                 185                 190

<210> SEQ ID NO 13
<211> LENGTH: 178
<212> TYPE: PRT
<213> ORGANISM: Homo sapiens

<400> SEQUENCE: 13

Tyr Pro Gly Thr Phe Tyr Phe Gln Phe Lys Asn Leu Trp Glu Ala Asn
1               5                   10                  15

Asp Arg Asp Glu Thr Trp Leu Cys Phe Thr Val Glu Gly Ile Lys Arg
            20                  25                  30

```
Arg Ser Val Val Ser Trp Lys Thr Gly Val Phe Arg Asn Gln Val Asp
            35                  40                  45

Ser Glu Thr His Cys His Ala Glu Arg Cys Phe Leu Ser Trp Phe Cys
 50                  55                  60

Asp Asp Ile Leu Ser Pro Asn Thr Lys Tyr Gln Val Thr Trp Tyr Thr
 65                  70                  75                  80

Ser Trp Ser Pro Cys Pro Asp Cys Ala Gly Glu Val Ala Glu Phe Leu
                 85                  90                  95

Ala Arg His Ser Asn Val Asn Leu Thr Ile Phe Thr Ala Arg Leu Tyr
                100                 105                 110

Tyr Phe Gln Tyr Pro Cys Tyr Gln Glu Gly Leu Arg Ser Leu Ser Gln
            115                 120                 125

Glu Gly Val Ala Val Glu Ile Met Asp Tyr Gly Asp Phe Lys Tyr Cys
130                 135                 140

Trp Glu Asn Phe Val Tyr Asn Asp Asn Glu Pro Phe Lys Pro Trp Lys
145                 150                 155                 160

Gly Leu Lys Thr Asn Phe Arg Leu Leu Lys Arg Arg Leu Arg Glu Ser
                165                 170                 175

Leu Gln

<210> SEQ ID NO 14
<211> LENGTH: 178
<212> TYPE: PRT
<213> ORGANISM: Homo sapiens

<400> SEQUENCE: 14

Tyr Pro His Ile Phe Tyr Phe His Phe Lys Asn Leu Arg Lys Ala Tyr
 1               5                  10                  15

Gly Arg Asn Glu Ser Trp Leu Cys Phe Thr Met Glu Val Val Lys His
            20                  25                  30

His Ser Pro Val Ser Trp Lys Arg Gly Val Phe Arg Asn Gln Val Asp
            35                  40                  45

Pro Glu Thr His Cys His Ala Glu Arg Cys Phe Leu Ser Trp Phe Cys
 50                  55                  60

Asp Asp Ile Leu Ser Pro Asn Thr Asn Tyr Glu Val Thr Trp Tyr Thr
 65                  70                  75                  80

Ser Trp Ser Pro Cys Pro Glu Cys Ala Gly Glu Val Ala Glu Phe Leu
                 85                  90                  95

Ala Arg His Ser Asn Val Asn Leu Thr Ile Phe Thr Ala Arg Leu Tyr
                100                 105                 110

Tyr Phe Trp Asp Thr Asp Tyr Gln Glu Gly Leu Arg Ser Leu Ser Gln
            115                 120                 125

Glu Gly Ala Ser Val Glu Ile Met Gly Tyr Lys Asp Phe Lys Tyr Cys
130                 135                 140

Trp Glu Asn Phe Val Tyr Asn Asp Asp Glu Pro Phe Lys Pro Trp Lys
145                 150                 155                 160

Gly Leu Lys Tyr Asn Phe Leu Phe Leu Asp Ser Lys Leu Gln Glu Ile
                165                 170                 175

Leu Glu

<210> SEQ ID NO 15
<211> LENGTH: 180
<212> TYPE: PRT
<213> ORGANISM: Bos taurus

<400> SEQUENCE: 15
```

```
Asp Pro Glu Thr Phe Tyr Phe Gln Phe Cys Asn Leu Leu Tyr Ala Asn
1               5                   10                  15

Arg Arg Asn Cys Ser Tyr Ile Cys Tyr Lys Val Glu Arg Lys Tyr
            20                  25                  30

His Ser Arg Ala Ser Phe Asp Trp Gly Val Phe His Asn Gln Val Tyr
            35                  40                  45

Gly Gly Thr Arg Cys His Thr Glu Leu Arg Phe Leu Ser Trp Phe His
50                  55                      60

Ala Glu Lys Leu Arg Pro Asn Glu Arg Tyr His Ile Thr Trp Phe Met
65                  70                  75                  80

Ser Trp Ser Pro Cys Met Lys Cys Ala Lys Glu Val Ala Asp Phe Leu
                85                  90                  95

Gly Arg His Gln Asn Val Thr Leu Ser Ile Phe Thr Ser Arg Leu Tyr
                100                 105                 110

Lys Phe Gln Glu Glu Gly Ser Arg Gln Gly Leu Leu Arg Leu Ser Asp
            115                 120                 125

Gln Gly Ala His Val Asp Ile Met Ser Tyr Gln Glu Phe Lys Tyr Cys
130                 135                 140

Trp Lys Lys Phe Val Tyr Ser Gln Arg Arg Pro Phe Arg Pro Trp Lys
145                 150                 155                 160

Lys Leu Asp Arg Asn Tyr Gln Arg Leu Val Glu Glu Leu Glu Asp Ile
                165                 170                 175

Leu Gly Asn Thr
            180

<210> SEQ ID NO 16
<211> LENGTH: 180
<212> TYPE: PRT
<213> ORGANISM: Ovis aries

<400> SEQUENCE: 16

Asp Pro Glu Thr Phe Tyr Phe Gln Phe His Asn Leu Leu Tyr Ala Tyr
1               5                   10                  15

Gly Arg Asn Cys Ser Tyr Ile Cys Tyr Arg Val Lys Thr Trp Lys His
            20                  25                  30

Arg Ser Pro Val Ser Phe Asp Trp Gly Val Phe His Asn Gln Val Tyr
            35                  40                  45

Ala Gly Thr His Cys His Ser Glu Arg Arg Phe Leu Ser Trp Phe Cys
50                  55                      60

Ala Lys Lys Leu Arg Pro Asp Glu Cys Tyr His Ile Thr Trp Phe Met
65                  70                  75                  80

Ser Trp Ser Pro Cys Met Lys Cys Ala Glu Leu Val Ala Gly Phe Leu
                85                  90                  95

Gly Met Tyr Gln Asn Val Thr Leu Ser Ile Phe Thr Ala Arg Leu Tyr
                100                 105                 110

Tyr Phe Gln Lys Pro Gln Tyr Arg Lys Gly Leu Leu Arg Leu Ser Asp
            115                 120                 125

Gln Gly Ala Cys Val Asp Ile Met Ser Tyr Gln Glu Phe Lys Tyr Cys
130                 135                 140

Trp Lys Lys Phe Val Tyr Ser Gln Arg Arg Pro Phe Arg Pro Trp Lys
145                 150                 155                 160

Lys Leu Lys Arg Asn Tyr Gln Leu Leu Ala Ala Glu Leu Glu Asp Ile
                165                 170                 175

Leu Gly Asn Thr
            180
```

<210> SEQ ID NO 17
<211> LENGTH: 175
<212> TYPE: PRT
<213> ORGANISM: Sus scrofa

<400> SEQUENCE: 17

```
Ser Pro Arg Thr Phe Ser Phe His Phe Arg Asn Leu Arg Phe Ala Ser
1               5                   10                  15

Gly Arg Asn Arg Ser Tyr Ile Cys Cys Gln Val Glu Gly Lys Asn Cys
            20                  25                  30

Phe Phe Gln Gly Ile Phe Gln Asn Gln Val Pro Pro Asp Pro Pro Cys
        35                  40                  45

His Ala Glu Leu Cys Phe Leu Ser Trp Phe Gln Ser Trp Gly Leu Ser
    50                  55                  60

Pro Asp Glu His Tyr Tyr Val Thr Trp Phe Ile Ser Trp Ser Pro Cys
65                  70                  75                  80

Cys Glu Cys Ala Ala Lys Val Ala Gln Phe Leu Glu Glu Asn Arg Asn
                85                  90                  95

Val Ser Leu Ser Leu Ser Ala Ala Arg Leu Tyr Tyr Phe Trp Lys Ser
            100                 105                 110

Glu Ser Arg Glu Gly Leu Arg Arg Leu Ser Asp Leu Gly Ala Gln Val
        115                 120                 125

Gly Ile Met Ser Phe Gln Asp Phe Gln His Cys Trp Asn Asn Phe Val
    130                 135                 140

His Asn Leu Gly Met Pro Phe Gln Pro Trp Lys Lys Leu His Lys Asn
145                 150                 155                 160

Tyr Gln Arg Leu Val Thr Glu Leu Lys Gln Ile Leu Arg Asn Thr
                165                 170                 175
```

<210> SEQ ID NO 18
<211> LENGTH: 179
<212> TYPE: PRT
<213> ORGANISM: Mus musculus

<400> SEQUENCE: 18

```
Ser Gln Glu Thr Phe Lys Phe His Phe Lys Asn Leu Arg Tyr Ala Ile
1               5                   10                  15

Asp Arg Lys Asp Thr Phe Leu Cys Tyr Glu Val Thr Arg Lys Asp Cys
            20                  25                  30

Asp Ser Pro Val Ser Leu His His Gly Val Phe Lys Asn Lys Asp Asn
        35                  40                  45

Ile His Ala Glu Ile Cys Phe Leu Tyr Trp Phe His Asp Lys Val Leu
    50                  55                  60

Lys Val Leu Ser Pro Arg Glu Glu Phe Lys Ile Thr Trp Tyr Met Ser
65                  70                  75                  80

Trp Ser Pro Cys Phe Glu Cys Ala Glu Gln Val Leu Arg Phe Leu Ala
                85                  90                  95

Thr His His Asn Leu Ser Leu Asp Ile Phe Ser Ser Arg Leu Tyr Asn
            100                 105                 110

Ile Arg Asp Pro Glu Asn Gln Gln Asn Leu Cys Arg Leu Val Gln Glu
        115                 120                 125

Gly Ala Gln Val Ala Ala Met Asp Leu Tyr Glu Phe Lys Lys Cys Trp
    130                 135                 140

Lys Lys Phe Val Asp Asn Gly Gly Arg Arg Phe Arg Pro Trp Lys Lys
145                 150                 155                 160

Leu Leu Thr Asn Phe Arg Tyr Gln Asp Ser Lys Leu Gln Glu Ile Leu
```

Arg Pro Cys

<210> SEQ ID NO 19
<211> LENGTH: 224
<212> TYPE: PRT
<213> ORGANISM: Homo sapiens

<400> SEQUENCE: 19

Met Ala Gln Lys Glu Glu Ala Val Ala Thr Glu Ala Ala Ser Gln
1               5                   10                  15

Asn Gly Glu Asp Leu Glu Asn Leu Asp Asp Pro Glu Lys Leu Lys Glu
            20                  25                  30

Leu Ile Glu Leu Pro Pro Phe Glu Ile Val Thr Gly Glu Arg Leu Pro
        35                  40                  45

Ala Asn Phe Phe Lys Phe Gln Phe Arg Asn Val Glu Tyr Ser Ser Gly
    50                  55                  60

Arg Asn Lys Thr Phe Leu Cys Tyr Val Val Glu Ala Gln Gly Lys Gly
65                  70                  75                  80

Gly Gln Val Gln Ala Ser Arg Gly Tyr Leu Glu Asp Glu His Ala Ala
                85                  90                  95

Ala His Ala Glu Glu Ala Phe Phe Asn Thr Ile Leu Pro Ala Phe Asp
            100                 105                 110

Pro Ala Leu Arg Tyr Asn Val Thr Trp Tyr Val Ser Ser Pro Cys
        115                 120                 125

Ala Ala Cys Ala Asp Arg Ile Ile Lys Thr Leu Ser Lys Thr Lys Asn
    130                 135                 140

Leu Arg Leu Leu Ile Leu Val Gly Arg Leu Phe Met Trp Glu Glu Pro
145                 150                 155                 160

Glu Ile Gln Ala Ala Leu Lys Lys Leu Lys Glu Ala Gly Cys Lys Leu
                165                 170                 175

Arg Ile Met Lys Pro Gln Asp Phe Glu Tyr Val Trp Gln Asn Phe Val
            180                 185                 190

Glu Gln Glu Gly Glu Ser Lys Ala Phe Gln Pro Trp Glu Asp Ile
        195                 200                 205

Gln Glu Asn Phe Leu Tyr Tyr Glu Glu Lys Leu Ala Asp Ile Leu Lys
    210                 215                 220

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 20
ncccgggtgg aataatctgc ctaaatat                                        28

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (1)..(1)
<223> OTHER INFORMATION: a, c, g, t, unknown or other

<400> SEQUENCE: 21
ngtcgactca cttaaattca ctgtatgtca t                              31

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 22
ncccggggat ccacccacat tcactttc                                  28

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 23
ngtcgactca cttaaattca ctgtatgtca t                              31

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 24
ncccgggcgg catgagactt acctgtgt                                  28

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 25
ngtcgactca cttaaattca ctgtatgtca t                              31

<210> SEQ ID NO 26
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 26
ncccgggtgg aataatctgc ctaaatat                                            28

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 27
ngtcgactca atcccagggc tggaagggac a                                        31

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 28
ncccggggat ccacccacat tcactttc                                            28

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 29
ngtcgactca atcccagggc tggaagggac a                                        31

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 30
ncccgggcgg catgagactt acctgtgt                                            28
```

```
<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 31
ngtcgactca atcccagggc tggaagggac a                                          31

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 32
ncccgggtgg aataatctgc ctaaatat                                              28

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 33
ngtcgacccc atccttcagt tttcctg                                               27

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 34
ncccggggat ccacccacat tcactttc                                              28

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

<223> OTHER INFORMATION: a, c, g, t, unknown or other

<400> SEQUENCE: 35
ngtcgacccc atccttcagt tttcctg                                            27

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 36
ncccgggcgg catgagactt acctgtgt                                           28

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other

<400> SEQUENCE: 37
ngtcgacccc atccttcagt tttcctg                                            27

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgatccaccc acagccactt tcaactttaa caatg                                   35

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cattgttaaa gttgaaagtg gctgtgggtg gatcg                                   35

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ccacccacat tcactgccaa ctttaacaat gaacc                                   35

```
<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggttcattgt taaagttggc agtgaatgtg ggtgg                         35

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccacattcac tttcaacgct aacaatgaac cttgg                         35

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ccaaggttca ttgttagcgt tgaaagtgaa tgtgg                         35

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cactttcaac tttaacaatg caccttgggt cag                           33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctgacccaag gtgcattgtt aaagttgaaa gtg                           33

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctttaacaat gaacctgcgg tcagaggacg gc                            32

<210> SEQ ID NO 47
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gccgtcctct gaccgcaggt tcattgttaa ag                                    32

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
caatgaacct tgggccagag gacggcatg                                        29

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
catgccgtcc tctggcccaa ggttcattg                                        29

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caatgaacct tgggtcgcag gacggcatga gac                                   33

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gtctcatgcc gtcctgcgac ccaaggttca ttg                                   33

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggacggcatg agactgctct gtgttatgag gtg                                   33

<210> SEQ ID NO 53
<211> LENGTH: 33
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 53
cacctcataa cacagagcag tctcatgccg tcc                                33

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cggcatgaga cttacgcgtg ttatgaggtg gagc                               34

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gctccacctc ataacacgcg taagtctcat gccg                               34

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggcatgagac ttacctggct tatgaggtgg agcgc                              35

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gcgctccacc tcataagcca ggtaagtctc atgcc                              35

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gagacttacc tgtgtgctga ggtggagcgc atg                                33

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic

```
oligonucleotide

<400> SEQUENCE: 59
catgcgctcc acctcagcac acaggtaagt ctc                             33

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cctgtgttat gaggcggagc gcatgcac                                   28

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gtgcatgcgc tccgcctcat aacacagg                                   28

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gaggtggagc gcgcgcacaa tgacacctg                                  29

<210> SEQ ID NO 63
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
caggtgtcat tgtgcgcgcg ctccacctc                                  29

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggagcgcatg cacgctgaca cctgggtc                                   28

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 65
gacccaggtg tcagcgtgca tgcgctcc                                              28

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gcacaatgac accgcggtcc tgctgaacc                                             29

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggttcagcag gaccgcggtg tcattgtgc                                             29

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
caatgacacc tgggccctgc tgaaccag                                              28

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ctggttcagc agggcccagg tgtcattg                                              28

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gacacctggg tcgcgctgaa ccagcgc                                               27

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
```
gcgctggttc agcgcgaccc aggtgtc                                               27

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cacctgggtc ctggcgaacc agcgcag                                               27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctgcgctggt tcgccaggac ccaggtg                                               27

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gcgcaggggc gctctatgca accagg                                                26

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cctggttgca tagagcgccc ctgcgc                                                26

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gcgcaggggc tttgcatgca accaggc                                               27

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcctggttgc atgcaaagcc cctgcgc                                               27

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cgcaggggct ttctagccaa ccaggctcca c                                  31

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gtggagcctg gttggctaga aagcccctgc g                                  31

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ccacataaac acggtgccct tgaaggccgc c                                  31

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggcggccttc aagggcaccg tgtttatgtg g                                  31

<210> SEQ ID NO 82
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cataaacacg gtttcgctga aggccgccat gc                                 32

<210> SEQ ID NO 83
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gcatggcggc cttcagcgaa accgtgttta tg                                 32

<210> SEQ ID NO 84

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cggtttcctt gaaggcgccc atgcagagct gtg                                 33

<210> SEQ ID NO 85
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cacagctctg catgggcgcc ttcaaggaaa ccg                                 33

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gaaggccgcc atgcagcgct gtgcttcctg gacg                                34

<210> SEQ ID NO 87
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cgtccaggaa gcacagcgct gcatggcggc cttc                                34

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cgccatgcag aggcgtgctt cctggac                                        27

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gtccaggaag cacgcctctg catggcg                                        27

<210> SEQ ID NO 90
<211> LENGTH: 34
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 90
gccatgcaga gctggccttc ctggacgtga ttcc                                   34

<210> SEQ ID NO 91
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggaatcacgt ccaggaaggc cagctctgca tggc                                   34

<210> SEQ ID NO 92
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gcagagctgt gcgccctgga cgtgattc                                          28

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gaatcacgtc cagggcgcac agctctgc                                          28

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cagagctgtg cttcgcggac gtgattccc                                         29

<210> SEQ ID NO 95
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gggaatcacg tccgcgaagc acagctctg                                         29

<210> SEQ ID NO 96
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 96
gtgcttcctg gacgcgattc ccttttgg                                            28

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ccaaaaggga atcgcgtcca ggaagcac                                            28

<210> SEQ ID NO 98
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cttcctggac gtggctccct tttggaagc                                           29

<210> SEQ ID NO 99
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcttccaaaa gggagccacg tccaggaag                                           29

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggacgtgatt cccgcttgga agctggacc                                           29

<210> SEQ ID NO 101
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggtccagctt ccaagcggga atcacgtcc                                           29

<210> SEQ ID NO 102
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 102
gacgtgattc cctttgcgaa gctggacctg g                            31

<210> SEQ ID NO 103
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccaggtccag cttcgcaaag ggaatcacgt c                            31

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gattcccttt tggaaggcgg acctggacca gga                          33

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tcctggtcca ggtccgcctt ccaaaaggga atc                          33

<210> SEQ ID NO 106
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cttttggaag ctggacgcgg accaggacta cag                          33

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ctgtagtcct ggtccgcgtc cagcttccaa aag                          33

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

```
ctggaccagg acgccagggt tacctgc                                              27
```

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 109

```
gcaggtaacc ctggcgtcct ggtccag                                              27
```

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 110

```
caggactaca gggctacctg cttcacc                                              27
```

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 111

```
ggtgaagcag gtagccctgt agtcctg                                              27
```

<210> SEQ ID NO 112
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 112

```
ggactacagg gttaccgcct tcacctcctg gagc                                      34
```

<210> SEQ ID NO 113
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 113

```
gctccaggag gtgaaggcgg taaccctgta gtcc                                      34
```

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 114

```
cagggttacc tgcgccacct cctggagc                                             28
```

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gctccaggag gtggcgcagg taaccctg                                      28

<210> SEQ ID NO 116
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cctgcttcac ctccgcgagc ccctgcttc                                     29

<210> SEQ ID NO 117
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gaagcagggg ctcgcggagg tgaagcagg                                     29

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ctcctggagc cccgccttca gctgtgccca g                                  31

<210> SEQ ID NO 119
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctgggcacag ctgaaggcgg ggctccagga g                                  31

<210> SEQ ID NO 120
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ctggagcccc tgcgccagct gtgcccagg                                     29

```
<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cctgggcaca gctggcgcag gggctccag                                        29

<210> SEQ ID NO 122
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gcccctgctt cagcgctgcc caggaaatgg c                                     31

<210> SEQ ID NO 123
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gccatttcct gggcagcgct gaagcagggg c                                     31

<210> SEQ ID NO 124
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cagctgtgcc caggaagcgg ctaaattcat ttcaaaaaac aaac                       44

<210> SEQ ID NO 125
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gtttgttttt tgaaatgaat ttagccgctt cctgggcaca gctg                       44

<210> SEQ ID NO 126
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gtgcccagga aatggctaaa gccatttcaa aaaacaaaca cgtgagcc                   48

<210> SEQ ID NO 127
<211> LENGTH: 48
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ggctcacgtg tttgtttttt gaaatggctt tagccatttc ctgggcac                    48

<210> SEQ ID NO 128
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ccaggaaatg gctaaattcg cttcaaaaaa caaacacgtg agc                         43

<210> SEQ ID NO 129
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gctcacgtgt ttgttttttg aagcgaattt agccatttcc tgg                         43

<210> SEQ ID NO 130
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gctaaattca tttcaaaaaa caaagccgtg agcctgtgc                              39

<210> SEQ ID NO 131
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gcacaggctc acggctttgt ttttgaaat gaatttagc                               39

<210> SEQ ID NO 132
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
catttcaaaa aacaaacacg cgagcctgtg catcttc                                37

<210> SEQ ID NO 133
<211> LENGTH: 37
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 133
gaagatgcac aggctcgcgt gtttgttttt tgaaatg                           37

<210> SEQ ID NO 134
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
caaaaaacaa acacgtgagc gcgtgcatct tcactgcc                         38

<210> SEQ ID NO 135
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ggcagtgaag atgcacgcgc tcacgtgttt gttttttg                         38

<210> SEQ ID NO 136
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
caaacacgtg agcctggcca tcttcactgc ccg                              33

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
cgggcagtga agatggccag gctcacgtgt ttg                              33

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cgtgagcctg tgcgccttca ctgcccgc                                    28

<210> SEQ ID NO 139
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
gcgggcagtg aaggcgcaca ggctcacg                                    28

<210> SEQ ID NO 140
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gagcctgtgc atcgccactg cccgcatc                                    28

<210> SEQ ID NO 141
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gatgcgggca gtggcgatgc acaggctc                                    28

<210> SEQ ID NO 142
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
catcttcact gcccgcgcct atgatgatca agg                              33

<210> SEQ ID NO 143
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ccttgatcat cataggcgcg ggcagtgaag atgc                             34

<210> SEQ ID NO 144
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cactgcccgc atcgctgatg atcaaggaag atgtc                            35

<210> SEQ ID NO 145
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 145
gacatcttcc ttgatcatca gcgatgcggg cagtg                              35

<210> SEQ ID NO 146
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gcatctatga tgatcaagga agagctcagg aggggctgc                          39

<210> SEQ ID NO 147
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gcagcccctc ctgagctctt ccttgatcat catagatgc                          39

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gatgtcagga gggggcgcgc accctggc                                     28

<210> SEQ ID NO 149
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gccagggtgc gcgcccctc ctgacatc                                      28

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
caggaggggc tggccaccct ggccg                                        25

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
```

```
cggccagggt ggccagcccc tcctg                                           25
```

<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152

```
gggctgcgca ccgcggccga ggctgg                                          26
```

<210> SEQ ID NO 153
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153

```
ccagcctcgg ccgcggtgcg cagccc                                          26
```

<210> SEQ ID NO 154
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154

```
ggctggggcc aaagcttcaa taatgacata cagtgaattt aag                       43
```

<210> SEQ ID NO 155
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155

```
cttaaattca ctgtatgtca ttattgaagc tttggcccca gcc                       43
```

<210> SEQ ID NO 156
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156

```
ctggggccaa aatttcagca atgacataca gtgaatttaa gcac                      44
```

<210> SEQ ID NO 157
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157

```
gtgcttaaat tcactgtatg tcattgctga aattttggcc ccag                      44
```

<210> SEQ ID NO 158
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ctggggccaa aatttcaata gcgacataca gtgaatttaa gcac                    44

<210> SEQ ID NO 159
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gtgcttaaat tcactgtatg tcgctattga aattttggcc ccag                    44

<210> SEQ ID NO 160
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gggccaaaat tcaataatg acagccagtg aatttaagca ctgc                     44

<210> SEQ ID NO 161
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gcagtgctta aattcactgg ctgtcattat tgaaattttg gccc                    44

<210> SEQ ID NO 162
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
caataatgac atacagtgca tttaagcact gctgg                              35

<210> SEQ ID NO 163
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ccagcagtgc ttaaatgcac tgtatgtcat tattg                              35

<210> SEQ ID NO 164

```
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
caataatgac atacagtgaa gctaagcact gctgggac                          38

<210> SEQ ID NO 165
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gtcccagcag tgcttagctt cactgtatgt cattattg                          38

<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gacatacagt gaatttaagc acgcctggga cacctttgtg                        40

<210> SEQ ID NO 167
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cacaaaggtg tcccaggcgt gcttaaattc actgtatgtc                        40

<210> SEQ ID NO 168
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
cagtgaattt aagcactgcg cggacacctt tgtgg                             35

<210> SEQ ID NO 169
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ccacaaaggt gtccgcgcag tgcttaaatt cactg                             35

<210> SEQ ID NO 170
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 170
ctgctgggac accgctgtgg accaccagg                                           29

<210> SEQ ID NO 171
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cctggtggtc cacagcggtg tcccagcag                                           29

<210> SEQ ID NO 172
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ctgggacacc tttgcggacc accaggg                                             27

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ccctggtggt ccgcaaaggt gtcccag                                             27

<210> SEQ ID NO 174
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gtggaccacc agggagctcc cttccagccc                                          30

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gggctggaag ggagctccct ggtggtccac                                          30

<210> SEQ ID NO 176
<211> LENGTH: 31
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 176
caccagggat gtcccgccca gccctgggat g                                              31

<210> SEQ ID NO 177
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
catcccaggg ctgggcggga catccctggt g                                              31

<210> SEQ ID NO 178
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cccttccagc ccgcggatgg actagatgag c                                              31

<210> SEQ ID NO 179
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gctcatctag tccatccgcg ggctggaagg g                                              31

<210> SEQ ID NO 180
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gccctgggat ggagcagatg agcacagcca ag                                             32

<210> SEQ ID NO 181
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
cttggctgtg ctcatctgct ccatcccagg gc                                             32

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 182
gagcacagcc aagacgcgag tgggaggctg                                              30

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
cagcctccca ctcgcgtctt ggctgtgctc                                              30

<210> SEQ ID NO 184
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gacctgagtg ggagggcgcg ggccattctc c                                            31

<210> SEQ ID NO 185
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggagaatggc ccgcgccctc ccactcaggt c                                            31

<210> SEQ ID NO 186
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ggctgcgggc cgctctccag aatcaggaaa ac                                           32

<210> SEQ ID NO 187
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gttttcctga ttctggagag cggcccgcag cc                                           32

<210> SEQ ID NO 188
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188

```
gctgcgggcc attgcccaga atcaggaaaa ctg                                33
```

<210> SEQ ID NO 189
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189

```
cagttttcct gattctgggc aatggcccgc agc                                33
```

<210> SEQ ID NO 190
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190

```
gatccaccca cattcactaa aaactttaac aatgaacctt gg                      42
```

<210> SEQ ID NO 191
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191

```
ccaaggttca ttgttaaagt ttttagtgaa tgtgggtgga tc                      42
```

<210> SEQ ID NO 192
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192

```
caactttaac aatgaaccta aagtcagagg acggc                              35
```

<210> SEQ ID NO 193
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193

```
gccgtcctct gactttaggt tcattgttaa agttg                              35
```

<210> SEQ ID NO 194
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194

```
caactttaac aatgaacctt ggaaaagagg acggcatgag                         40
```

<210> SEQ ID NO 195
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ctcatgccgt cctctttcc aaggttcatt gttaaagttg                              40

<210> SEQ ID NO 196
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ggacggcatg agactaaact gtgttatgag gtggag                                 36

<210> SEQ ID NO 197
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ctccacctca taacacagtt tagtctcatg ccgtcc                                 36

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gagacttacc tgtgttatga gaaagagcgc atgcacaatg                             40

<210> SEQ ID NO 199
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
cattgtgcat gcgctctttc tcataacaca ggtaagtctc                             40

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gaggtggagc gcaaacacaa tgacacctgg                                        30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ccaggtgtca ttgtgtttgc gctccacctc                                        30

<210> SEQ ID NO 202
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gcatgcacaa tgacaccaaa gtcctgctga accag                                  35

<210> SEQ ID NO 203
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ctggttcagc aggactttgg tgtcattgtg catgc                                  35

<210> SEQ ID NO 204
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gcacaatgac acctggaaac tgctgaacca gcg                                    33

<210> SEQ ID NO 205
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
cgctggttca gcagtttcca ggtgtcattg tgc                                    33

<210> SEQ ID NO 206
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
caatgacacc tgggtcaaac tgaaccagcg cag                                    33

<210> SEQ ID NO 207
<211> LENGTH: 33

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ctgcgctggt tcagtttgac ccaggtgtca ttg                              33

<210> SEQ ID NO 208
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gacacctggg tcctgaaaaa ccagcgcagg g                                31

<210> SEQ ID NO 209
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ccctgcgctg gtttttcagg acccaggtgt c                                31

<210> SEQ ID NO 210
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cagcgcaggg gcaaactatg caaccaggct c                                31

<210> SEQ ID NO 211
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gagcctggtt gcatagtttg ccctgcgct g                                 31

<210> SEQ ID NO 212
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gcgcaggggc tttaaatgca accaggctc                                   29

<210> SEQ ID NO 213
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 213
gagcctggtt gcatttaaag ccccctgcgc                                      29

<210> SEQ ID NO 214
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tccacataaa cacggtaaac ttgaaggccg cc                                   32

<210> SEQ ID NO 215
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ggcggccttc aagtttaccg tgtttatgtg ga                                   32

<210> SEQ ID NO 216
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
ccacataaac acggtttcaa agaaggccgc catgc                                35

<210> SEQ ID NO 217
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gcatggcggc cttctttgaa accgtgttta tgtgg                                35

<210> SEQ ID NO 218
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ccgccatgca gagaaatgct tcctggacgt g                                    31

<210> SEQ ID NO 219
<211> LENGTH: 31
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 219
cacgtccagg aagcatttct ctgcatggcg g                                31

<210> SEQ ID NO 220
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
catgcagagc tgtgcaaact ggacgtgatt ccc                              33

<210> SEQ ID NO 221
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gggaatcacg tccagtttgc acagctctgc atg                              33

<210> SEQ ID NO 222
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gctgtgcttc ctggacaaaa ttcccttttg gaagc                            35

<210> SEQ ID NO 223
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gcttccaaaa gggaattttg tccaggaagc acagc                            35

<210> SEQ ID NO 224
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gcttcctgga cgtgaaaccc ttttggaagc tgg                              33

<210> SEQ ID NO 225
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ccagcttcca aaagggtttc acgtccagga agc                33

<210> SEQ ID NO 226
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tcctggacgt gattcccaaa tggaagctgg acctgg             36

<210> SEQ ID NO 227
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ccaggtccag cttccatttg ggaatcacgt ccagga             36

<210> SEQ ID NO 228
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gacgtgattc cctttaaaaa gctggacctg g                  31

<210> SEQ ID NO 229
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ccaggtccag ctttttaaag ggaatcacgt c                  31

<210> SEQ ID NO 230
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230 cctttggaa gctggacaaa gaccaggact acagg               35

<210> SEQ ID NO 231
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
cctgtagtcc tggtctttgt ccagcttcca aaagg                    35

<210> SEQ ID NO 232
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
cctggaccag gacaaaaggg ttacctgctt c                        31

<210> SEQ ID NO 233
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gaagcaggta acccttttgt cctggtccag g                        31

<210> SEQ ID NO 234
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ccaggactac aggaaaacct gcttcacctc                          30

<210> SEQ ID NO 235
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gaggtgaagc aggttttcct gtagtcctgg                          30

<210> SEQ ID NO 236
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ctggagcccc tgcaaaagct gtgcccagg                           29

<210> SEQ ID NO 237
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
cctgggcaca gcttttgcag gggctccag                           29

<210> SEQ ID NO 238
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ccaggaaatg gctaaattca aatcaaaaaa caaacacgtg agc                          43

<210> SEQ ID NO 239
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
gctcacgtgt ttgttttttg atttgaattt agccatttcc tgg                          43

<210> SEQ ID NO 240
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
cgtgagcctg tgcatcaaaa ctgcccgcat ctatgatg                                38

<210> SEQ ID NO 241
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
catcatagat gcgggcagtt ttgatgcaca ggctcacg                                38

<210> SEQ ID NO 242
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ctggggccaa aatttcaaaa atgacataca gtgaatttaa gc                           42

<210> SEQ ID NO 243
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gcttaaattc actgtatgtc attttttgaaa ttttggcccc ag                          42

<210> SEQ ID NO 244

-continued

```
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gggccaaaat tcaataatg acaaaaagtg aatttaagca ctgctg            46

<210> SEQ ID NO 245
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cagcagtgct taaattcact ttttgtcatt attgaaattt tggccc            46

<210> SEQ ID NO 246
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ctgctgggac acctttaaag accaccaggg atg                          33

<210> SEQ ID NO 247
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
catccctggt ggtctttaaa ggtgtcccag cag                          33

<210> SEQ ID NO 248
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gagcacagcc aagacaaaag tgggaggctg c                            31

<210> SEQ ID NO 249
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gcagcctccc actttttgtct tggctgtgct c                           31

<210> SEQ ID NO 250
<211> LENGTH: 34
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 250
ggctgcgggc caaactccag aatcaggaaa actg                                 34

<210> SEQ ID NO 251
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
cagttttcct gattctggag tttggcccgc agcc                                 34

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gcttcttcta ccttctcttg a                                               21

<210> SEQ ID NO 253
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
aaacccaaaa                                                            10

<210> SEQ ID NO 254
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gggagaccca aagag                                                      15

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
aaagggagac ccaaagagga                                                 20

<210> SEQ ID NO 256
<211> LENGTH: 80
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 256
ggattggttg gttatttgtt taaggaaggt ggattaaggg cccaataagg tgatggaagt    60
tatgtttggt agattgatgg                                                80

<210> SEQ ID NO 257
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(31)
<223> OTHER INFORMATION: Any amino acid and this region may encompass
      23 to 28 residues
<220> FEATURE:
<221> NAME/KEY: MOD_RES
<222> LOCATION: (33)..(36)
<223> OTHER INFORMATION: Any amino acid and this region may encompass
      2 to 4 residues

<400> SEQUENCE: 257

His Xaa Glu Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Cys
            20                  25                  30

Xaa Xaa Xaa Xaa Cys
        35

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Ile or Leu
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Leu or Ile

<400> SEQUENCE: 258

Leu Xaa Xaa Phe Xaa Xaa Arg Xaa Tyr
1               5

<210> SEQ ID NO 259
<211> LENGTH: 60
<212> TYPE: PRT
<213> ORGANISM: Homo sapiens

<400> SEQUENCE: 259

```
Thr Phe Thr Phe Asn Phe Asn Asn Glu Pro Trp Val Arg Gly Arg His
1               5                   10                  15

Glu Thr Tyr Leu Cys Tyr Glu Val Glu Arg Met His Asn Asp Thr Trp
                20              25                  30

Val Leu Leu Asn Gln Arg Arg Gly Phe Leu Cys Asn Gln Ala Pro His
            35              40                  45

Lys His Gly Phe Leu Glu Gly Arg His Ala Glu Leu
    50              55                  60

<210> SEQ ID NO 260
<211> LENGTH: 60
<212> TYPE: PRT
<213> ORGANISM: Homo sapiens

<400> SEQUENCE: 260

Cys Phe Leu Asp Val Ile Pro Phe Trp Lys Leu Asp Leu Asp Gln Asp
1               5                   10                  15

Tyr Arg Val Thr Cys Phe Thr Ser Trp Ser Pro Cys Phe Ser Cys Ala
                20              25                  30

Gln Glu Met Ala Lys Phe Ile Ser Lys Asn Lys His Val Ser Leu Cys
            35              40                  45

Ile Phe Thr Ala Arg Ile Tyr Asp Asp Gln Gly Arg
    50              55                  60

<210> SEQ ID NO 261
<211> LENGTH: 60
<212> TYPE: PRT
<213> ORGANISM: Homo sapiens

<400> SEQUENCE: 261

Cys Gln Glu Gly Leu Arg Thr Leu Ala Glu Ala Gly Ala Lys Ile Ser
1               5                   10                  15

Ile Met Thr Tyr Ser Glu Phe Lys His Cys Trp Asp Thr Phe Val Asp
                20              25                  30

His Gln Gly Cys Pro Phe Gln Pro Trp Asp Gly Leu Asp Glu His Ser
            35              40                  45

Gln Asp Leu Ser Gly Arg Leu Arg Ala Ile Leu Gln
    50              55                  60
```